(12) United States Patent
Kris et al.

(10) Patent No.: US 7,659,063 B2
(45) Date of Patent: Feb. 9, 2010

(54) HIGH THROUGHPUT ASSAY SYSTEM

(75) Inventors: Richard Kris, Tucson, AZ (US); Stephen Felder, Tucson, AZ (US)

(73) Assignee: High Throughput Genomics, Inc., Tucson, AZ (US)

( * ) Notice: Subject to any disclaimer, the term of this patent is extended or adjusted under 35 U.S.C. 154(b) by 0 days.

(21) Appl. No.: 10/865,853

(22) Filed: Jun. 14, 2004

(65) Prior Publication Data

US 2005/0026193 A1 Feb. 3, 2005

Related U.S. Application Data

(63) Continuation of application No. 09/888,413, filed on Jun. 26, 2001.

(51) Int. Cl.
*C12Q 1/68* (2006.01)
*C12N 1/06* (2006.01)

(52) U.S. Cl. .......................... 435/6; 435/259

(58) Field of Classification Search .................. 435/6, 435/91.1, 91.2; 536/24.3
See application file for complete search history.

(56) References Cited

U.S. PATENT DOCUMENTS

| | | | |
|---|---|---|---|
| 4,228,237 A | 10/1980 | Hevey et al. |
| 4,563,419 A | 1/1986 | Ranki et al. |
| 4,716,106 A | 12/1987 | Chiswell |
| 4,751,177 A | 6/1988 | Stabinsky |
| 4,868,105 A | 9/1989 | Urdea et al. |
| 4,883,760 A | 11/1989 | Heelies |
| 4,925,785 A | 5/1990 | Wang et al. |
| 4,994,373 A | 2/1991 | Stavrianopoulos et al. |
| 5,063,081 A | 11/1991 | Cozzette et al. |
| 5,143,854 A | 9/1992 | Pirrung et al. |
| 5,175,270 A | 12/1992 | Nilsen et al. |
| 5,212,295 A | 5/1993 | Cook |
| 5,241,060 A | 8/1993 | Engelhardt et al. |
| 5,252,743 A | 10/1993 | Barrett et al. |
| 5,288,609 A | 2/1994 | Engelhardt et al. |
| 5,310,469 A | 5/1994 | Cunningham et al. |
| 5,324,633 A | 6/1994 | Fodor et al. |
| 5,358,691 A | 10/1994 | Clark et al. |
| 5,374,524 A | 12/1994 | Miller |
| 5,378,638 A | 1/1995 | Deeg et al. |
| 5,422,241 A | 6/1995 | Goldrick et al. |
| 5,445,934 A | 8/1995 | Fodor et al. |
| 5,449,754 A | 9/1995 | Nishioka |
| 5,451,500 A | 9/1995 | Stapleton |
| 5,470,705 A | 11/1995 | Grossman et al. |
| 5,472,672 A | 12/1995 | Brennan |
| 5,474,796 A | 12/1995 | Brennan |
| 5,482,867 A | 1/1996 | Barrett et al. |
| 5,486,452 A | 1/1996 | Gordon et al. |
| 5,498,539 A * | 3/1996 | Harrison et al. ............ 435/365 |
| 5,510,270 A | 4/1996 | Fodor et al. |
| 5,545,531 A | 8/1996 | Rava et al. |
| 5,547,839 A | 8/1996 | Dower et al. |
| 5,556,748 A | 9/1996 | Douglas |
| 5,556,752 A | 9/1996 | Lockhart et al. |
| 5,556,762 A | 9/1996 | Pinilla et al. |
| 5,561,043 A | 10/1996 | Cantor et al. |
| 5,565,322 A | 10/1996 | Heller |
| 5,599,695 A | 2/1997 | Pease et al. |
| 5,605,798 A | 2/1997 | Koster |
| 5,629,153 A * | 5/1997 | Urdea ........................... 435/6 |
| 5,643,730 A | 7/1997 | Banker et al. |
| 5,650,274 A | 7/1997 | Kambara et al. |
| 5,653,939 A | 8/1997 | Hollis et al. |
| 5,661,028 A | 8/1997 | Foote |
| 5,677,195 A | 10/1997 | Winkler et al. |
| 5,683,872 A | 11/1997 | Rudert et al. |
| 5,686,279 A | 11/1997 | Finer et al. |
| 5,700,637 A | 12/1997 | Southern et al. |
| 5,744,305 A | 4/1998 | Fodor et al. |
| 5,753,439 A | 5/1998 | Smith et al. |
| 5,763,263 A | 6/1998 | Dehlinger |
| 5,770,370 A * | 6/1998 | Kumar ........................... 435/6 |
| 5,770,456 A | 6/1998 | Holmes |
| 5,770,722 A | 6/1998 | Lockhart et al. |
| 5,789,165 A | 8/1998 | Oku et al. |
| 5,807,522 A | 9/1998 | Brown et al. |
| 5,831,070 A | 11/1998 | Pease et al. |
| 5,843,655 A | 12/1998 | McGall |
| 5,945,334 A | 8/1999 | Besemer et al. |
| 6,027,889 A | 2/2000 | Barany et al. |
| 6,051,377 A | 4/2000 | Mandecki |

(Continued)

FOREIGN PATENT DOCUMENTS

DE 19518217 11/1995

(Continued)

OTHER PUBLICATIONS

Li et al., "IL-1B alters the expression of the receptor tyrosine kinase gene r-EphA3 in neonatal rat cardiomyocytes," AJP—Heart and Circulatory Phyiology, Jan. 1998, vol. 274, No. 1, pp. H331-H341.*

(Continued)

*Primary Examiner*—Young J Kim
(74) *Attorney, Agent, or Firm*—Millen, White, Zelano & Branigan, P.C.

(57) ABSTRACT

The present invention relates to compositions, apparatus and methods useful for concurrently performing multiple, high throughput, biological or chemical assays, using repeated arrays of probes. A combination of the invention comprises a surface, which comprises a plurality of test regions, at least two of which, and in a preferred embodiment, at least twenty of which, are substantially identical, wherein each of the test regions comprises an array of generic anchor molecules. The anchors are associated with bifunctional linker molecules, each containing a portion which is specific for at least one of the anchors and a portion which is a probe specific for a target of interest. The resulting array of probes is used to analyze the presence or test the activity of one or more target molecules which specifically interact with the probes. In a preferred embodiment, a sample to be tested is subjected to a nuclease protection procedure before it is contacted with a combination of the invention.

81 Claims, 39 Drawing Sheets

U.S. PATENT DOCUMENTS

| | | | |
|---|---|---|---|
| 6,051,380 | A | 4/2000 | Sosnowski et al. |
| 6,054,270 | A | 4/2000 | Southern |
| 6,083,763 | A | 7/2000 | Balch |
| 6,121,048 | A | 9/2000 | Zaffaroni et al. |
| 6,156,501 | A | 12/2000 | McGall et al. |
| 6,200,781 | B1 | 3/2001 | Tal et al. |
| 6,232,066 | B1 | 5/2001 | Felder et al. |
| 6,238,869 | B1 | 5/2001 | Kris et al. |
| 6,423,492 | B1 | 7/2002 | Harbron |
| 6,780,617 | B2 * | 8/2004 | Chen .................. 435/91.2 |

FOREIGN PATENT DOCUMENTS

| | | |
|---|---|---|
| EP | 0063810 | 11/1982 |
| EP | 0698792 | 2/1996 |
| EP | 0 721 016 | 7/1996 |
| EP | 0742286 | 11/1996 |
| EP | 0 846 776 A | 6/1998 |
| WO | WO 86/00991 | 2/1986 |
| WO | WO 87/06621 A1 | 11/1987 |
| WO | WO 89/11548 | 11/1989 |
| WO | WO 91/08307 | 6/1991 |
| WO | WO 91/15600 | 10/1991 |
| WO | WO 93 25563 | 12/1993 |
| WO | WO 94/11530 | 5/1994 |
| WO | WO 94/12670 | 6/1994 |
| WO | WO 95/35505 | 9/1995 |
| WO | WO 96/29431 | 9/1996 |
| WO | WO 97/05277 | 2/1997 |
| WO | WO 97/07245 | 2/1997 |
| WO | WO 97/10365 | 3/1997 |
| WO | WO 97/19749 | 6/1997 |
| WO | WO 97/26324 A1 | 7/1997 |
| WO | WO 9727317 | 7/1997 |
| WO | WO 9731256 | 8/1997 |
| WO | WO 97/33000 | 9/1997 |
| WO | WO 97/47640 | 12/1997 |
| WO | WO 98/29736 | 7/1998 |
| WO | WO 98/46790 A1 | 10/1998 |
| WO | WO 99 28494 A | 6/1999 |
| WO | WO 99/32663 | 7/1999 |
| WO | WO 00/37683 | 6/2000 |
| WO | WO 00/37684 | 6/2000 |
| WO | WO 00/79008 | 12/2000 |
| WO | WO 03/002750 | 1/2003 |
| WO | WO 03018630 A1 * | 3/2003 |

OTHER PUBLICATIONS

Furlong et al., "Induction of Limited DNA Damage by the Antitumor Agent Cain's Acridine," Cancer Research, May 1978, vol. 38, pp. 1329-1335.*

Uccini et al., "High Requency of Epstein-Barr Virus Genome Detection in Hodgkin's Disease of HIV-Positive Patients," Int. J. Cancer: 46, 581-585 (1990).

Blomqvist et al., "Strong evolutionary conservation of neuropeptide Y: Sequences of chicken, goldfish, and Torpedo marmorata DNA clones," Neurobiology, vol. 89, pp. 2350-2354, Mar. 1992.

Burnett et al., "Cloning and Sequencing of Flavin-containing Monooxygenases FMO3 and FMO4 from Rabbit and Characterization of FMO3," J.Biological Chemistry, vol. 269, No. 19, May 13, 1994, pp. 14314-14322.

Bauman et al., "Flow Cytometric Detection of Ribosomal RNA in Suspended Cells by Fluorescent In Situ Hybridization[1,2]," Cytometry, 9:517-524, (1988).

D.P. Little et al., Anal. Chem., vol. 69, No. 22, pp. 4540-4546 (1997): "MALDI on a Chip: Analysis of Arrays of Low-Femtole to Subfemtomole Quantities of . . . ".

A.C. Pease et al., Proc. Natl. Acad. Sci. USA, vol. 91, pp. 5022-5026 (1994): "Light-generated oligonucleotide arrays for rapid DNA sequence analysis".

D. Sarracino et al., Bioorganic & Medicinal Chemistry Letters, vol. 6, No. 21, pp. 2543-2548 (1996): "Quantitative Maldi-tof MS of Oligonucleotides and a Nuclease Assay".

K. Tang et al., Rapid Comm. in Mass Spectrometry, vol. 8, pp. 183-186 (1994): "Matrix-assisted laser desorption/ionization of restriction enzyme-digested DNA".

International Search Report for PCT/US98/27191, 1999.

International Search Report for PCT/US99/30515, 1999.

Scholler et al., Fine-mapping of shotgun template libraries; an efficient strategy for the systematic sequencing of genomic DNA, Nucleic Acid Research, GB Oxford University Press, Surry, vol. 23, No. 19, 1995, pp. 3842-3849.

Lehrach, H., et al., "Hybridization fingerprinting in genome mapping and sequencing", Genome Analysis vol. 1: Genetic and Physical Mapping, US, Cold Spring Harbor Lab. Press, 1990, pp. 39-81.

Labat I., et al., "Simulations of ordering and sequence reconstruction of random DNA clones hybridized with a small number of oligomeric probes", International Conference on Bioinformatics, XX, XX, 1993, pp. 555-565.

Maier et al., Drug Discovery Today, vol. 2 (8), pp. 315-324, 1997.

Alper, "Weighting DNA for Fast Genetic Diagnosis", Science, vol. 279, Mar. 27, 1998, pp. 2044-2045.

Anderson et al., "Polynucleotide Arrays for Genetic Sequence Analysis", Topics in Current Chemistry, vol. 194, 1998, pp. 118-129.

Beattie et al., "Advances in Genosensor Research", Clinical Chemistry, vol. 41, No. 5, 1995, pp. 700-706.

Niemeyer et al., "Hybirdization characteristics of biomolecular adaptors, covalent DNA-Streptavidin conjugates," Bioconjugate Chem., 1998, pp. 168-175, vol. 9.

Brown, D., "DNA-Encoded Chips Appear to Speed," The Washington Post. Science Biotechnology, Nov. 24, 1997.

Hacia et al., To affinity . . . and beyond! Nature Genetics, Dec. 14, 1996, pp. 367-369, vol. 14, No. 4.

Blanchard et al., "Sequence to array: Probing the genome's secrets," Analysis Research News, Dec. 14, 1996, pp. 1649-1684, vol. 14.

Chee et al., "Accessing Genetic information with High-Density DNA Arrays", Science, vol. 274, Oct. 25, 1996, pp. 610-614.

Chetverin et al., "Oligonucleotide Arrays: New Concepts and Possibilites", Bio/Technology, vol. 12, Nov. 12, 1994, pp. 1093-1099.

DeRisi et al., "Use of a cDNA Microarray to Analyse Gene Expression Patterns in Human Cancer", Nature Genetics, vol. 14, Dec. 1996, pp. 457-460.

Eggers et al., "A Microchip for Quantitative Detection . . . ", BioTechniques, vol. 17, No. 3 (1994), pp. 516-524.

Eggers et al., "A Review of Microfabricated Devices for Gene-Based Diagnostics", Hematologic Pathology 9(1), 1-15 (1995).

Gautheret et al., "Alternate Polyadenylation in Human mRNAs . . . ", Genome Research, 8:524-530 (1998).

Maskos et al., "A Novel Method for the Parallel Analysis of Multiple Mutations in Multiple Samples", Nucleic Acids Research, 1993, vol. 21, No. 9, pp. 2269-2270.

Hoheisel, "Oligomer-chip Technology", BioTechnology TIBTECH, Nov. 1997, vol. 15, No. 1 (166), pp. 465-469.

Lipshutz et al., "Using Oligonucleotide Probe Arrays to Access Genetic Diversity", BioTechniques, vol. 19, No. 3, (1995), pp. 442-447.

Lockhart et al., "Expression Monitoring by Hybridization to High-Density Oligonucleotide Arrays", Nature Biotechnology, vol. 14, Dec. 1996, pp. 1675-1680.

Marshall et al., "DNA chips: An array of possibilities", Nature Biotechnology, vol. 16, Jan. 1998, pp. 27-31.

Niemeyer et al., "Oligonucleotide-directed self-assembly of proteins . . . ", Nucleic Acids Research, 1994, vol. 22, No. 25, pp. 5530-5539.

O'Donnell-Maloney et al., "The Development of Microfabricated Arrays of DNA Sequencing and Analysis", TIBTECH, vol. 14, Oct. 1996.

Sapolsky et al., "Mapping Genomic Library Clones Using Oligonucleotide Arrays", Genomics, 33, 445-456 (1996).

Shulleck et al., "A High-Density Screening Format for Encoded Combinatorial Libraries . . . ", Analytical Biochemistry, 246, 20-29 (1997).

Shoemaker et al., "Quantitative Phenotypic Analysis of Yeast Deletion . . . ", Nature Genetics, vol. 14, Dec. 1996, pp. 450-456.

Shuber et al., "High Throughput Parallel Analysis of Hundreds of Patient Samples . . . ", *Human Molecular Genetics* 1997, vol. 6, No. 3, pp. 337-347.

Southern, "DNA chips: analysing sequence by hybridization . . . ", *Trends in GENETICS*, vol. 12, 1996.

Southern, "High-density gridding: techniques and applications", *Current Opinion in Biotechnology*, vol. 7, No. 1, Feb. 1996, pp. 85-88.

Kowalak, J., et al. "Posttranscriptional Modification of the Central Loop of Domain V in *Escherichia coli* 23 S Ribosomal RNA", *The Journal of Biological Chemistry*, vol. 270, No. 30, Jul. 28, 1995, pp. 17758-17764.

Fodor, S., et al., "Multiplexed biochemical assays with biological chips," Nature, Aug. 5, 1993, pp. 555-556, vol. 364.

Litia, A., et al., "Simultaneous detection of two cystic fibrosis alleles using dual-label time-resolved fluorometry," Molecular and Cellular Probes, Sep. 10, 1992, pp. 505-512, vol. 6.

Fodor et al., "Light directed spatially addressable parallel chemical synthesis," Science, Feb. 15, 1991, pp. 767-773, vol. 251.

Giorda et al., "Non-radioisotopic typing of human leukocyte antigen class II genes on microplates," Bio Techniques, 1993, pp. 918-20, 922-5, vol. 15, No. 5.

Ebersole et al., "Spontaneously formed functionally active avidin monolayers on metal surfaces: a strategy for immobilizing biological reagents and design of piezoelectric biosensors," J. Am. Chem. Soc., 1990, pp. 3239-3241, vol. 112, No. 8.

Landsgraf et al., "Direct analysis of polymerase chain reaction products using enzyme-linked immunosorbent assay techniques," Analytical Biochemistry, 1991, pp. 86-91, vol. 198.

Schena et al., "Quantitative monitoring og gene expression patterns with a complementary DNA microarray," Science, 1995, pp. 467-470, vol. 270.

Blanchard et al., "High-density oligonucleotide arrays," Biosens and Bioelectron, 1996, pp. 687-690, vol. 11, No. 6/7.

Arnheim et al., "PCR analysis of DNA sequences in single cells: single sperm gene mapping and genetic disease diagnosis," Genomics, 1990, pp. 415-419, vol. 4.

Ferguson et al., "A fiber-optic DNA biosensor microarray for the analysis of gene expression," Nature Biotech, 1996, pp. 1681-1684, vol. 14.

Graham et al., "Gene probe assay on a fiber-optic evanescent wave biosendor," Biosens. Bioelectron., 1992, pp. 487-493, No. 7.

Stimpson et al., "Real-time detection of DNA hybirdization and melting on oligonucleotide arrays by using optical wave guides," PNAS USA, pp. 6379-6383, vol. 92, 1995.

Hacia et al., "Detection of hetrozygous mutations in BRCA1 using high density oligonucleotide arrays and two-colour fluorescence analysis," Nature genetics, Dec. 1996, pp. 441-447, vol. 14.

Blomqvist, A.G., et al., "Strong Evolutionary Conservation of Neuropeptide Y: Sequences of Chicken, Goldfish, and *Torpedo Marmorata* DNA Clones", Proc. Natl. Acad. Sci. USA, vol. 89, pp. 2350-2354, Mar. 1992—Neurobiology.

Cohen, E., et al., "Morphological effects and metabolism of the molting hormone in *Aedes aegypti* cultured cells," Insect Biochemistry, vol. 6, No. 4, Jan. 1, 1976, pp. 433-439.

Li, W., et al., "Porcine endometrial epithelial cells immortalized by transfection with origin-defective, temperature-sensitive simian virus 40 DNA," Life Sciences, vol. 51, No. 25, Jan. 1, 1992, pp. 1969-1979.

Li, X., et al., Paxillin is tyrosine-phosphorylated by and preferentially associates with the calcium-dependent tyrosine kinase in rat liver epithelial cells, the Jrnl of Biol. Chem., vol. 272, No. 22, May 30, 1997, pp. 14341-14348.

Wallner, G., et al., "Optimizing Fluorescent in Situ Hybridization with rRNA-targeted Oligonucleotide Probes for Flow Cytometric Identification of Microorganisms," Cytometry, vol. 14, No. 2, Jan. 1, 1993, pp. 136-143.

Shain, D.H., et al., "Sodium dodecyl sulfate (SDS)-based wholemount in situ hybridization of *Xenopus laevis* embryos, Jrnl of Biochem. & Biophy. Methods," vol. 31, No. 3-4, Feb. 5, 1996, pp. 185-188.

Ebling, P.M., et al., "DNA hybridization assay for detection of nucleopolyhedrovirus in whitemarked tussock moth (*Orgyia leucostigma*) larvae," Pest Mgmt Science, vol. 57, No. 1, Jan. 2001, pp. 66-71.

Krajewski, S., et al., "Detection of Multiple Antigens on Western Blots," Analytical Biochem., vol. 236, 1996, pp. 221-228.

\* cited by examiner

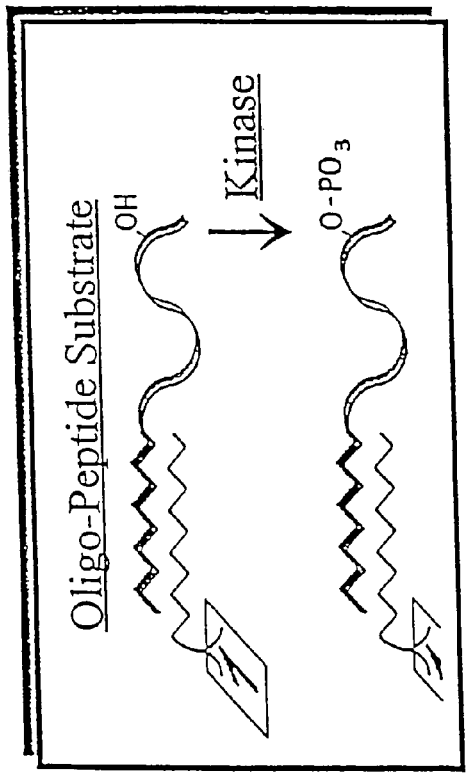
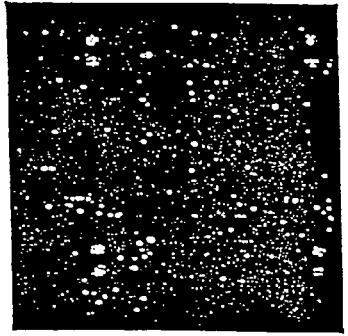
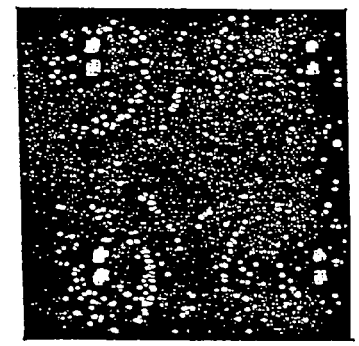
Fig 17

Control THP-1 Cells | Activated THP-1 monocytes

↘ Turned Off
↖ Turned On

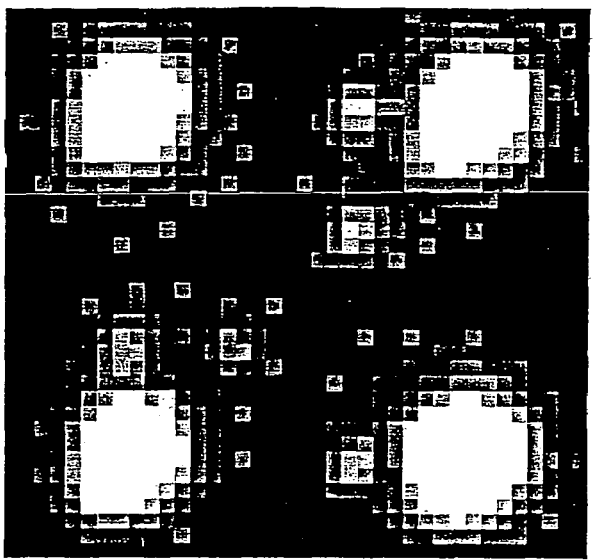
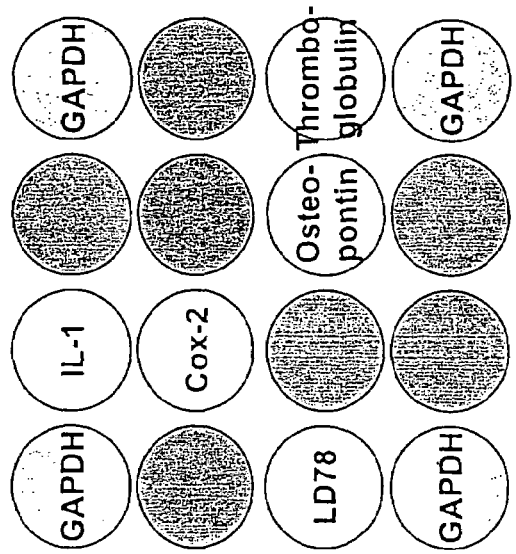
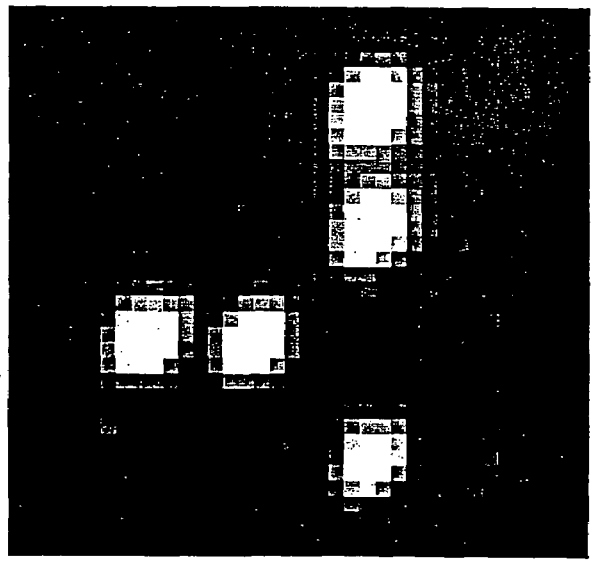
Fig 29

SEQUENCE LISTING

<160> NUMBER OF SEQ ID NOS: 165

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 1
tccacgtgag gaccggacgg cgtcc                                           25

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 2
gtcgtttcca tctttgcagt cataggatac tgagtggacg ccgtccggtc ctcacgtgga    60

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Synthetic
      RNA mimic oligonucleotide
<220> FEATURE:
<223> OTHER INFORMATION: mouse C-jun

<400> SEQUENCE: 3
ctatgactgc aaagatggaa acgacgatac tgagttggac ctaacattcg atctcattca    60

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      detector oligonucleotide

<400> SEQUENCE: 4
tgaatgagat cgaatgttag gtcca                                           25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 5
cactacggct gagcacgtgc gctgc                                           25

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 6
ctaggctgaa gtgtggctgg agtctgcagc gcacgtgctc agccgtagtg          50

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      RNA mimic oligonucleotide
<220> FEATURE:
<223> OTHER INFORMATION: mouse MIP-2

<400> SEQUENCE: 7
agactccagc cacacttcag cctaggatac tgagtctgaa caaaggcaag gctaactgac    60

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      detector oligonucleotide

<400> SEQUENCE: 8
gtcagttagc cttgcctttg ttcag                                       25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 9
gtcagttagc cttgcctttg ttcag                                       25

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 10
accatgtagt tgaggtcaat gaagggcgct cccacaacgc tcgaccggcg             50

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: Synthetic
      RNA mimic oligonucleotide
<220> FEATURE:
<223> OTHER INFORMATION: mouse GAPDH

<400> SEQUENCE: 11
ccttcattga cctcaactac atggtgatac tgagtggaga aacctgccaa gtatgatgac    60

<210> SEQ ID NO 12
<211> LENGTH: 25
<212> TYPE: DNA
<213> ORGANISM: Artificial Sequence

```
<220> FEATURE:
<223> OTHER INFORMATION: Description of Artificial Sequence: Synthetic
      detector oligonucleotide

<400> SEQUENCE: 12
gtcatcatac ttggcaggtt tctcc                                            25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 13
gaaccgctcg cgtgttctac agcca                                            25

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 14
ctaccgagca aactggaaat gaaattggct gtagaacacg cgagcggttc                 50

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence: Synthetic
      RNA mimic oligonucleotide
<220> FEATURE:
<223> OTHER INFORMATION: mouse L32 protein

<400> SEQUENCE: 15
atttcatttc cagtttgctc ggtaggatac tgagtgagtc accaatccca acgccaggct      60

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      detector oligonucleotide

<400> SEQUENCE: 16
agcctggcgt tgggattggt gactc                                            25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 17
ctcgttccgc gtccgtggct gccag                                            25

<210> SEQ ID NO 18
<211> LENGTH: 25
<212> TYPE: DNA
```

<213> ORGANISM: Artificial Sequence
<220> FEATURE:
<223> OTHER INFORMATION: Description of Artificial Sequence: Synthetic
      linker oligonucleotide

<400> SEQUENCE: 18
ctggcagcca cggacgcgga acgag                                          25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 19
cggtcggcat ggtaccacag tccgc                                          25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 20
gcggactgtg gtaccatgcc gaccg                                          25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 21
gcgcgccgcg ttatgcatct cttcg                                          25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 22
cgaagagatg cataacgcgg cgccg                                          25

<210> SEQ ID NO 23
<211> LENGTH: 70
<212> TYPE: DNA
<213> ORGANISM: Artificial Sequence
<220> FEATURE:
<223> OTHER INFORMATION: Description of Artificial Sequence: Synthetic
      full length protection fragment oligonucleotide

<400> SEQUENCE: 23
cgagaaatat gacaactcac tcaagattgt cagcaatgca tcctgcacca ccaactgctt    60
gcttgtctaa                                                           70

<210> SEQ ID NO 24
<211> LENGTH: 60

```
<212> TYPE: DNA
<213> ORGANISM: Artificial Sequence
<220> FEATURE:
<223> OTHER INFORMATION: Description of Artificial Sequence: Synthetic
      short protection oligonucleotide

<400> SEQUENCE: 24
cgagaaatat gacaactcac tcaagattgt cagcaatgca tcctgcacca ccaactgctt    60

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 25
cgccggtcga gcgttgtggg agcgc                                          25

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 26
cttgagtgag ttgtcatatt tctcggatac tgagtgcgct cccacaacgc tcgaccggcg    60

<210> SEQ ID NO 27
<211> LENGTH: 70
<212> TYPE: DNA
<213> ORGANISM: Artificial Sequence
<220> FEATURE:
<223> OTHER INFORMATION: Description of Artificial Sequence: Synthetic
      protection fragment oligonucleotide
<220> FEATURE:
<223> OTHER INFORMATION: complementary to mouse antisense mRNA for GAPDH

<400> SEQUENCE: 27
cgagaaatat gacaactcac tcaagattgt cagcaatgca tcctgcacca ccaactgctt    60
gcttgtctaa                                                           70

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      detector oligonucleotide
<220> FEATURE:
<221> NAME/KEY: modified_base
<222> LOCATION: (1)
<223> OTHER INFORMATION: biotin-labeled adenine

<400> SEQUENCE: 28
nagcagttgg tggtgcagga tgcat                                          25

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide
```

-continued

```
<400> SEQUENCE: 29
atgcatcctg caccaccaac tgcttgatac tgagtgcgct cccacaacgc tcgaccggcg    60

<210> SEQ ID NO 30
<211> LENGTH: 70
<212> TYPE: DNA
<213> ORGANISM: Artificial Sequence
<220> FEATURE:
<223> OTHER INFORMATION: Description of Artificial Sequence: Synthetic
      protection fragment oligonucleotide
<220> FEATURE:
<223> OTHER INFORMATION: complementery to mouse mRNA for GAPDH

<400> SEQUENCE: 30
aagcagttgg tggtgcagga tgcattgctg acaatcttga gtgagttgtc atatttctcg    60
gcttgtctaa                                                           70

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      detector oligonucleotide

<400> SEQUENCE: 31
cgagaaatat gacaactcac tcaag                                          25

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: phosphotyrosine

<400> SEQUENCE: 32

Thr Ser Glu Pro Gln Xaa Gln Pro Gly Glu Asn Leu
 1               5                  10

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      probe oligonucleotide
<220> FEATURE:
<223> OTHER INFORMATION: conjugated to HRP

<400> SEQUENCE: 33
cacctccaaa cagtgaagga gagca                                          25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 34
cgccggtcga gcgttgtggg agcgc                                          25
```

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence: Synthetic
target oligonucleotide

<400> SEQUENCE: 35
tgagaagtat gacaacagcc tcaagatcat cagcaatgcc tcctgcacca ccaactgctt    60

<210> SEQ ID NO 36
<211> LENGTH: 60
<212> TYPE: DNA
<213> ORGANISM: Artificial Sequence
<220> FEATURE:
<223> OTHER INFORMATION: Description of Artificial Sequence: Synthetic
linker oligonucleotide

<400> SEQUENCE: 36
atgcctcctg caccaccaac tgcttgatac tgagtgcgct cccacaacgc tcgaccggcg    60

<210> SEQ ID NO 37
<211> LENGTH: 75
<212> TYPE: DNA
<213> ORGANISM: Artificial Sequence
<220> FEATURE:
<223> OTHER INFORMATION: Description of Artificial Sequence: Synthetic
protection fragment oligonucleotide

<400> SEQUENCE: 37
aagcagttgg tggtgcagga ggcattgctg atgatcttga ggctgttgtc atacttctca    60
gcttgtctaa gtctg                                                    75

<210> SEQ ID NO 38
<211> LENGTH: 60
<212> TYPE: DNA
<213> ORGANISM: Artificial Sequence
<220> FEATURE:
<223> OTHER INFORMATION: Description of Artificial Sequence: Synthetic
detection-linker oligonucleotide

<400> SEQUENCE: 38
tgctctcctt cactgtttgg aggtggatac tgagttgaga agtatgacaa cagcctcaag    60

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
attenuation factor oligonucleotide

<400> SEQUENCE: 39
tgagaagtat gacaacagcc tcaag                                         25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
anchor oligonucleotide

<400> SEQUENCE: 40

```
tccacgtgag gaccggacgg cgtcc                                           25
```

<210> SEQ ID NO 41
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 41

```
cgacacatgg gataacgagg cttatgtgca cgatgcacct gtacgatcac tgaactgcac     60
```

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 42

```
cacctgtacg atcactgaac tgcacgatac tgagtggacg ccgtccggtc ctcacgtgga     60
```

<210> SEQ ID NO 43
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 43

```
gtgcagttca gtgatcgtac aggtgcatcg tgcacataag cctcgttatc ccatgtgtcg     60
gcttgtctaa gtctg                                                      75
```

<210> SEQ ID NO 44
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 44

```
tgctctcctt cactgtttgg aggtggatac tgagtcgaca catgggataa cgaggcttat     60
```

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 45

```
cgacacatgg gataacgagg cttat                                           25
```

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 46

```
cactacggct gagcacgtgc gctgc                                              25
```

<210> SEQ ID NO 47
<211> LENGTH: 60
<212> TYPE: DNA
<213> ORGANISM: Artificial Sequence
<220> FEATURE:
<223> OTHER INFORMATION: Description of Artificial Sequence: Synthetic
    target oligonucleotide

<400> SEQUENCE: 47

```
cggaacccaa gcttagaact ttaagcaaca agaccaccac ttcgaaacct gggattcagg        60
```

<210> SEQ ID NO 48
<211> LENGTH: 60
<212> TYPE: DNA
<213> ORGANISM: Artificial Sequence
<220> FEATURE:
<223> OTHER INFORMATION: Description of Artificial Sequence: Synthetic
    linker oligonucleotide

<400> SEQUENCE: 48

```
accacttcga aacctgggat tcagggatac tgagtgcagc gcacgtgctc agccgtagtg        60
```

<210> SEQ ID NO 49
<211> LENGTH: 75
<212> TYPE: DNA
<213> ORGANISM: Artificial Sequence
<220> FEATURE:
<223> OTHER INFORMATION: Description of Artificial Sequence: Synthetic
    protection fragment oligonucleotide

<400> SEQUENCE: 49

```
cctgaatccc aggtttcgaa gtggtggtct tgttgcttaa agttctaagc ttgggttccg        60
gcttgtctaa gtctg                                                         75
```

<210> SEQ ID NO 50
<211> LENGTH: 60
<212> TYPE: DNA
<213> ORGANISM: Artificial Sequence
<220> FEATURE:
<223> OTHER INFORMATION: Description of Artificial Sequence: Synthetic
    detection-linker oligonucleotide

<400> SEQUENCE: 50

```
tgctctcctt cactgtttgg aggtggatac tgagtcggaa cccaagctta gaactttaag        60
```

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
    attenuation factor oligonucleotide

<400> SEQUENCE: 51

```
cggaacccaa gcttagaact ttaag                                              25
```

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
    anchor oligonucleotide -continued

```
<400> SEQUENCE: 52
gaaccgctcg cgtgttctac agcca                                         25

<210> SEQ ID NO 53
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 53
gcggaccatc cagaatgaca tcatgttatt gcagctgagc agaagagtca gacggaatcg   60

<210> SEQ ID NO 54
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 54
tgagcagaag agtcagacgg aatcggatac tgagttggct gtagaacacg cgagcggttc   60

<210> SEQ ID NO 55
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 55
cgattccgtc tgactcttct gctcagctgc aataacatga tgtcattctg gatggtccgc   60
gcttgtctaa gtctg                                                    75

<210> SEQ ID NO 56
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 56
tgctctcctt cactgtttgg aggtggatac tgagtgcgga ccatccagaa tgacatcatg   60

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 57
gcggaccatc cagaatgaca tcatg                                         25

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide
```

<400> SEQUENCE: 58
ctcgttccgc gtccgtggct gccag 25

<210> SEQ ID NO 59
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 59
ccgaggtgta tgtatgagtg tgggatttga ccagtataag tgcgattgta cccggacagg 60

<210> SEQ ID NO 60
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 60
ataagtgcga ttgtacccgg acagggatac tgagtctggc agccacggac gcggaacgag 60

<210> SEQ ID NO 61
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 61
cctgtccggg tacaatcgca cttatactgg tcaaatccca cactcataca tacacctcgg 60
gcttgtctaa gtctg 75

<210> SEQ ID NO 62
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 62
tgctctcctt cactgtttgg aggtggatac tgagtccgag gtgtatgtat gagtgtggga 60

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 63
ccgaggtgta tgtatgagtg tggga 25

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic

```
                anchor oligonucleotide

<400> SEQUENCE: 64
cggtcggcat ggtaccacag tccgc                                               25

<210> SEQ ID NO 65
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 65
cacctccaaa cagtgaagga gagcagggtc caaatggaag tcagaactct agctacagcc         60

<210> SEQ ID NO 66
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 66
ggaagtcaga actctagcta cagccgatac tgagtgcgga ctgtggtacc atgccgaccg         60

<210> SEQ ID NO 67
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 67
ggctgtagct agagttctga cttccatttg gaccctgctc tccttcactg tttggaggtg         60
gcttgtctaa gtctg                                                          75

<210> SEQ ID NO 68
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 68
tgctctcctt cactgtttgg aggtggatac tgagtcacct ccaaacagtg aaggagagca         60

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 69
cacctccaaa cagtgaagga gagca                                               25

<210> SEQ ID NO 70
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      anchor oligonucleotide

<400> SEQUENCE: 70
gcgcgccgcg ttatgcatct cttcg                                          25

<210> SEQ ID NO 71
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 71
gtggatgccc ttaaaggaac caatgagtcc ctggaacgcc agatgcgtga atggaagag    60

<210> SEQ ID NO 72
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 72
acgccagatg cgtgaaatgg aagaggatac tgagtcgaag agatgcataa cgcggcgcgc    60

<210> SEQ ID NO 73
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 73
ctcttccatt tcacgcatct ggcgttccag ggactcattg gttcctttaa gggcatccac    60
gcttgtctaa gtctg                                                     75

<210> SEQ ID NO 74
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 74
tgctctcctt cactgtttgg aggtggatac tgagtgtgga tgcccttaaa ggaaccaatg    60

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 75
gtggatgccc ttaaaggaac caatg                                          25

<210> SEQ ID NO 76
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      anchor oligonucleotide

<400> SEQUENCE: 76
gttagcatac gtgtcaccac accgg                                            25

<210> SEQ ID NO 77
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 77 caccteccga cagattccac agaatttcat agctgactac tttgagacga gcagccagtg      60

<210> SEQ ID NO 78
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 78
actactttga gacgagcagc cagtggatac tgagtccggt gtggtgacac gtatgctaac      60

<210> SEQ ID NO 79
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 79
cactggctgc tcgtctcaaa gtagtcagct atgaaattct gtggaatctg tcgggaggtg      60
gcttgtctaa gtctg                                                       75

<210> SEQ ID NO 80
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 80
tgctctcctt cactgtttgg aggtggatac tgagtcacct cccgacagat tccacagaat      60

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 81 caccteccga cagattccac agaat                                            25

<210> SEQ ID NO 82
<211> LENGTH: 25
<212> TYPE: DNA
```

<213> ORGANISM: Artificial Sequence
<220> FEATURE:
<223> OTHER INFORMATION: Description of Artificial Sequence: Synthetic
      anchor oligonucleotide

<400> SEQUENCE: 82
cgtcagtccg tcggccagct cttcc                                          25

<210> SEQ ID NO 83
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 83
caaaggtgaa ggacgaacca cagagaagat ccgcgaggtt gtctgctaaa cctgctcctc    60

<210> SEQ ID NO 84
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 84
aggttgtctg ctaaacctgc tcctcgatac tgagtggaag agctggccga cggactgacg    60

<210> SEQ ID NO 85
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 85
gaggagcagg tttagcagac aacctcgcgg atcttctctg tggttcgtcc ttcacctttg    60
gcttgtctaa gtctg                                                     75

<210> SEQ ID NO 86
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 86
tgctctcctt cactgtttgg aggtggatac tgagtcaaag gtgaaggacg aaccacagag    60

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 87
caaaggtgaa ggacgaacca cagag                                          25

<210> SEQ ID NO 88
<211> LENGTH: 25

```
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 88
atccagttaa ccacatgcta gtacc                                                25

<210> SEQ ID NO 89
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 89
ccgtgggaag gacagttatg aaacgagtca gctggatgac cagagtgctg aaacccacag          60

<210> SEQ ID NO 90
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 90
atgaccagag tgctgaaacc cacaggatac tgagtggtac tagcatgtgg ttaactggat          60

<210> SEQ ID NO 91
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 91
ctgtgggttt cagcactctg gtcatccagc tgactcgttt cataactgtc cttcccacgg          60
gcttgtctaa gtctg                                                           75

<210> SEQ ID NO 92
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 92
tgctctcctt cactgtttgg aggtggatac tgagtccgtg ggaaggacag ttatgaaacg          60

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 93
ccgtgggaag gacagttatg aaacg                                                25

<210> SEQ ID NO 94
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 94
ttagcgttgg ccgaggttca tagcc                                          25

<210> SEQ ID NO 95
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 95
gtgtaaacat gacttccaag ctggccgtgg ctctcttggc agccttcctg atttctgcag    60

<210> SEQ ID NO 96
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 96
ttggcagcct tcctgatttc tgcaggatac tgagtggcta tgaacctcgg ccaacgctaa    60

<210> SEQ ID NO 97
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 97
ctgcagaaat caggaaggct gccaagagag ccacggccag cttggaagtc atgtttacac    60
gcttgtctaa gtctg                                                     75

<210> SEQ ID NO 98
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 98
tgctctcctt cactgtttgg aggtggatac tgagtgtgta acatgactt ccaagctggc    60

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 99
gtgtaaacat gacttccaag ctggc                                          25
```

<210> SEQ ID NO 100
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 100
cattacgagt gcattcgcat caagg                                           25

<210> SEQ ID NO 101
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 101
cacgctctct ggacttcaca gaactggatg ttgctgctga gaagattgac aggttcatgc     60

<210> SEQ ID NO 102
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 102
gctgagaaga ttgacaggtt catgcgatac tgagtccttg atgcgaatgc actcgtaatg     60

<210> SEQ ID NO 103
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 103
gcatgaacct gtcaatcttc tcagcagcaa catccagttc tgtgaagtcc agagagcgtg     60
gcttgtctaa gtctg                                                     75

<210> SEQ ID NO 104
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 104
tgctctcctt cactgtttgg aggtggatac tgagtcacgc tctctggact tcacagaact     60

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 105
cacgctctct ggacttcaca gaact                                           25

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 106
atcatgtaag tcttcggtcg gtggc                                              25

<210> SEQ ID NO 107
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 107
gagtcctgtg gcatccacga aactaccttc aactccatca tgaagtgtga cgtggacatc        60

<210> SEQ ID NO 108
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 108
catcatgaag tgtgacgtgg acatcgatac tgagtgccac cgaccgaaga cttacatgat        60

<210> SEQ ID NO 109
<211> LENGTH: 74
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 109
gatgtccacg tcacacttca tgatggattg aaggtagttt cgtggatgcc acaggactcg        60
cttgtctaag tctg                                                          74

<210> SEQ ID NO 110
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 110
tgctctcctt cactgtttgg aggtggatac tgagtgagtc ctgtggcatc cacgaaacta        60

<210> SEQ ID NO 111
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 111
gagtcctgtg gcatccacga aacta                                              25

<210> SEQ ID NO 112
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 112
gagtcctgtg gcatccacga aacta                                            25

<210> SEQ ID NO 113
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 113
gacgtggttc ccaaagatgt caatgctgcc attgccacca tcaagaccaa gcgtaccatc      60

<210> SEQ ID NO 114
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 114
caccatcaag accaagcgta ccatcgatac tgagtccacg tcccttccta gagacgctta     60

<210> SEQ ID NO 115
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 115
gatggtacgc ttggtcttga tggtggcaat ggcagcattg acatctttgg gaaccacgtc      60
gcttgtctaa gtctg                                                       75

<210> SEQ ID NO 116
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 116
tgctctcctt cactgtttgg aggtggatac tgagtgacgt ggttcccaaa gatgtcaatg     60

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 117

-continued

```
gacgtggttc ccaaagatgt caatg                                        25
```

<210> SEQ ID NO 118
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 118

```
cggtcggcat ggtaccacag tccgc                                        25
```

<210> SEQ ID NO 119
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 119

```
gagggagcag acaggaggaa tcatgtcagg cctgtgtgtg aaaggaagct ccactgtcac    60
```

<210> SEQ ID NO 120
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 120

```
gtgtgaaagg aagctccact gtcacgatac tgagtgcgga ctgtggtacc atgccgaccg    60
```

<210> SEQ ID NO 121
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 121

```
gtgacagtgg agcttccttt cacacacagg cctgacatga ttcctcctgt ctgctccctc    60
gcttgtctaa gtctg                                                   75
```

<210> SEQ ID NO 122
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 122

```
tgctctcctt cactgtttgg aggtggatac tgagtgaggg agcagacagg aggaatcatg    60
```

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 123
gagggagcag acaggaggaa tcatg                                                25

<210> SEQ ID NO 124
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 124
gcgcgccgcg ttatgcatct cttcg                                                25

<210> SEQ ID NO 125
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 125
cactacaagc agcactgccc tccaaccccg gaaacttcct gtgcaaccca gattatcacc          60

<210> SEQ ID NO 126
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 126
ttcctgtgca acccagatta tcaccgatac tgagtcgaag agatgcataa cgcggcgcgc          60

<210> SEQ ID NO 127
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 127
ggtgataatc tgggttgcac aggaagtttc cggggttgga gggcagtgct gcttgtagtg          60
gcttgtctaa gtctg                                                           75

<210> SEQ ID NO 128
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 128
tgctctcctt cactgtttgg aggtggatac tgagtcacta caagcagcac tgccctccaa          60

<210> SEQ ID NO 129
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

```
<400> SEQUENCE: 129
ctccaacact acaagcagca ctgcc                                             25

<210> SEQ ID NO 130
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 130
gttagcatac gtgtcaccac accgg                                             25

<210> SEQ ID NO 131
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 131
cagggaggca agaccttcat tgtgggagac cagatctcct tcgctgacta caacctgctg       60

<210> SEQ ID NO 132
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 132
ctccttcgct gactacaacc tgctggatac tgagtccggt gtggtgacac gtatgctaac       60

<210> SEQ ID NO 133
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 133
cagcaggttg tagtcagcga aggagatctg gtctcccaca atgaaggtct tgcctccctg       60
gcttgtctaa gtctg                                                        75

<210> SEQ ID NO 134
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 134
tgctctcctt cactgtttgg aggtggatac tgagtcaggg aggcaagacc ttcattgtgg       60

<210> SEQ ID NO 135
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide
```

<400> SEQUENCE: 135
cagggaggca agaccttcat tgtgg                                            25

<210> SEQ ID NO 136
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 136
atccagttaa ccacatgcta gtacc                                            25

<210> SEQ ID NO 137
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 137
gggtttatgt gtcagggtgg tgacttcaca cgccataatg gcactggtgg caagtccatc     60

<210> SEQ ID NO 138
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 138
taatggcact ggtggcaagt ccatcgatac tgagtggtac tagcatgtgg ttaactggat     60

<210> SEQ ID NO 139
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 139
gatggacttg ccaccagtgc cattatggcg tgtgaagtca ccaccctgac acataaaccc     60
gcttgtctaa gtctg                                                       75

<210> SEQ ID NO 140
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 140
tgctctcctt cactgtttgg aggtggatac tgagtgggtt tatgtgtcag ggtggtgact     60

<210> SEQ ID NO 141
<211> LENGTH: 25
<212> TYPE: DNA
<213> ORGANISM: Artificial Sequence
<220> FEATURE:
<223> OTHER INFORMATION: Description of Artificial Sequence: Synthetic attenuation factor oligonucleotide

<400> SEQUENCE: 141
gggtttatgt gtcagggtgg tgact 25

<210> SEQ ID NO 142
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 142
tctcggtctg gaacgcccgg caact 25

<210> SEQ ID NO 143
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 143
ggtggttgag agtgcttatg aggtgatcaa actcaaaggc tacacatcct gggctattgg 60

<210> SEQ ID NO 144
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 144
aaggctacac atcctgggct attgggatac tgagtagttg ccgggcgttc cagaccgaga 60

<210> SEQ ID NO 145
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 145
ccaatagccc aggatgtgta gcctttgagt ttgatcacct cataagcact ctcaaccacc 60
gcttgtctaa gtctg 75

<210> SEQ ID NO 146
<211> LENGTH: 75
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 146
ccaatagccc aggatgtgta gcctttgagt ttgatcacct cataagcact ctcaaccacc 60
gcttgtctaa gtctg 75

<210> SEQ ID NO 147
<211> LENGTH: 25
<212> TYPE: DNA

<213> ORGANISM: Artificial Sequence
<220> FEATURE:
<223> OTHER INFORMATION: Description of Artificial Sequence: Synthetic
      attenuation factor oligonucleotide

<400> SEQUENCE: 147
ggtggttgag agtgcttatg aggtg                                       25

<210> SEQ ID NO 148
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 148
cattacgagt gcattcgcat caagg                                       25

<210> SEQ ID NO 149
<211> LENGTH: 25
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 149
cattacgagt gcattcgcat caagg                                       25

<210> SEQ ID NO 150
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 150
cagtgtttcc ctgtttatcc atcccgatac tgagtccttg atgcgaatgc actcgtaatg    60

<210> SEQ ID NO 151
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 151
gggatggata aacagggaaa cactgtgcat tcctcacagc caacagtgta ggtcttggtg    60
gcttgtctaa gtctg                                                  75

<210> SEQ ID NO 152
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 152
tgctctcctt cactgtttgg aggtggatac tgagtcacca agacctacac tgttggctgt    60

<210> SEQ ID NO 153
<211> LENGTH: 25

```
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 153
caccaagacc tacactgttg gctgt                                         25

<210> SEQ ID NO 154
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 154
atcatgtaag tcttcggtcg gtggc                                         25

<210> SEQ ID NO 155
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 155
gcaacgtgaa catcttcgac gccatcgcgg agattgggaa ccagctgtat ttgttcaagg   60

<210> SEQ ID NO 156
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 156
gggaaccagc tgtatttgtt caagggatac tgagtgccac cgaccgaaga cttacatgat   60

<210> SEQ ID NO 157
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 157
ccttgaacaa atacagctgg ttcccaatct ccgcgatggc gtcgaagatg ttcacgttgc   60
gcttgtctaa gtctg                                                   75

<210> SEQ ID NO 158
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 158
tgctctcctt cactgtttgg aggtggatac tgagtgcaac gtgaacatct tcgacgccat   60

<210> SEQ ID NO 159
```

<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 159
gcaacgtgaa catcttcgac gccat                                          25

<210> SEQ ID NO 160
<211> LENGTH: 25
<212> TYPE: DNA
<213> ORGANISM: Artificial Sequence
<220> FEATURE:
<223> OTHER INFORMATION: Description of Artificial Sequence: Synthetic
      anchor oligonucleotide

<400> SEQUENCE: 160
ctgagtcctc cggtgcctac gtggc                                          25

<210> SEQ ID NO 161
<211> LENGTH: 60
<212> TYPE: DNA
<213> ORGANISM: Artificial Sequence
<220> FEATURE:
<223> OTHER INFORMATION: Description of Artificial Sequence: Synthetic
      target oligonucleotide

<400> SEQUENCE: 161
gagtcctgtg gcatccacga aactaccttc aactccatca tgaagtgtga cgtggacatc    60

<210> SEQ ID NO 162
<211> LENGTH: 60
<212> TYPE: DNA
<213> ORGANISM: Artificial Sequence
<220> FEATURE:
<223> OTHER INFORMATION: Description of Artificial Sequence: Synthetic
      linker oligonucleotide

<400> SEQUENCE: 162
catcatgaag tgtgacgtgg acatcgatac tgagtgccac gtaggcaccg gaggactcag    60

<210> SEQ ID NO 163
<211> LENGTH: 75
<212> TYPE: DNA
<213> ORGANISM: Artificial Sequence
<220> FEATURE:
<223> OTHER INFORMATION: Description of Artificial Sequence: Synthetic
      protection fragment oligonucleotide

<400> SEQUENCE: 163
gatgtccacg tcacacttca tgatggagtt gaaggtagtt tcgtggatgc cacaggactc    60
gcttgtctaa gtctg                                                     75

<210> SEQ ID NO 164
<211> LENGTH: 60
<212> TYPE: DNA
<213> ORGANISM: Artificial Sequence
<220> FEATURE:
<223> OTHER INFORMATION: Description of Artificial Sequence: Synthetic
      detection-linker oligonucleotide

<400> SEQUENCE: 164
tgctctcctt cactgtttgg aggtggatac tgagtgagtc ctgtggcatc cacgaaacta    60

```
<210> SEQ ID NO 165
<211> LENGTH: 25
<212> TYPE: DNA
<213> ORGANISM: Artificial Sequence
<220> FEATURE:
<223> OTHER INFORMATION: Description of Artificial Sequence: Synthetic
      attenuation factor oligonucleotide

<400> SEQUENCE: 165
gagtcctgtg gcatccacga aacta                                             25
```

HIGH THROUGHPUT ASSAY SYSTEM

This application is a continuation of U.S. patent application Ser. No. 09/888,413, filed on Jun. 26, 2001.

FIELD OF THE INVENTION

This invention relates, e.g., to compositions, apparatus and methods useful for concurrently performing multiple biological or chemical assays, using repeated arrays of probes. A plurality of regions each contains an array of generic anchor molecules. The anchors are associated with bifunctional linker molecules, each containing a portion which is specific for at least one of the anchors and a portion which is a probe specific for a target of interest. The resulting array of probes is used to analyze the presence of one or more target molecules which interact specifically with the probes. The invention relates to diverse fields distinguished by the nature of the molecular interaction, including but not limited to pharmaceutical drug discovery, molecular biology, biochemistry, pharmacology and medical diagnostic technology.

BACKGROUND OF THE INVENTION

Pluralities of molecular probes arranged on surfaces or "chips" have been used in a variety of biological and chemical assays. Assays are performed to determine if target molecules of interest interact with any of the probes. After exposing the probes to target molecules under selected test conditions, detection devices determine whether a target molecule has interacted with a given probe.

These systems are useful in a variety of screening procedures for obtaining information about either the probes or the target molecules. For example, they have been used to screen for peptides or potential drugs which bind to a receptor of interest, among others; to screen samples for the presence of, for example, genetic mutations, allelic variants in a population, or a particular pathogen or strain of pathogen, among many others; to study gene expression, for example to identify the mRNAs whose expression is correlated with a particular physiological condition, developmental stage, or disease state, etc.

DESCRIPTION OF THE INVENTION

This invention provides compositions, apparatus and methods for concurrently performing multiple biological or chemical assays, and allows for high throughput analysis of multiple samples—for example, multiple patient samples to be screened in a diagnostic assay, or multiple potential drugs or therapeutic agents to be tested in a method of drug discovery. A combination is provided which is useful for the detection of one or more targets in a sample. This combination comprises a surface comprising a plurality of spatially discrete regions, which can be termed test regions and which can be wells, at least two of which are substantially identical. Each surface comprises at least two, preferably at least twenty or more, e.g., at least about 25, 50, 96, 864, or 1536, etc., of such substantially identical regions. Each test region defines a space for the introduction of a sample containing (or potentially containing) one or more targets and contains a biological or chemical array. (Phrases such as "sample containing a target" or "detecting a target in a sample" are not meant to exclude samples or determinations (detection attempts) where no target is contained or detected. In a general sense, this invention involves arrays to determine whether a target is contained in a sample irrespective of whether it is or is not detected.) This array comprises generic "anchors," each in association with a bifunctional linker molecule which has a first portion that is specific for the anchor and a second portion that comprises a probe which is specific for at least one of the target(s). The combination of this invention is placed in contact with a sample containing one or more targets, which optionally react with a detector molecule(s), and is then interrogated by a detection device which detects reactions between target molecules and probes in the test regions, thereby generating results of the assay.

The invention provides methods and compositions particularly useful for high throughput biological assays. In especially preferred embodiments, the invention can be used for high throughput screening for drug discovery. For example, a high throughput assay can be run in many (100 for example) 96-well microplates at one time. Each well of a plate can have, e.g., 36 different tests performed in it by using an array of about 36 anchor and linker pairs. That is, 100 plates, with 96 wells per plate, and each with 36 tests per well, can allow for a total of 345,000 tests; for example, each of 9,600 different drug candidates can be tested simultaneously for 36 different parameters or assays. High throughput assays provide much more information for each drug candidate than do assays which test only one parameter at a time. For example, it is possible in a single initial high throughput screening assay to determine whether a drug candidate is selective, specific and/or nontoxic. Non-high throughput methods necessitate extensive follow-up assays to test such parameters for each drug candidate of interest. Several types of high throughput screening assays are described, e.g., in Examples 15-17. The ability to perform simultaneously a wide variety of biological assays and to do very many assays at once (i.e., in very high throughput) are two important advantages of the invention.

In one embodiment, for example, using 96-well DNA Bind plates (Corning Costar) made of polystyrene with a derivatized surface for the attachment of primary amines, such as amino acids or modified oligonucleotides, a collection of 36 different oligonucleotides can be spotted onto the surface of every well of every plate to serve as anchors. The anchors can be covalently attached to the derivatized polystyrene, and the same 36 anchors can be used for all screening assays. For any particular assay, a given set of linkers can be used to program the surface of each well to be specific for as many as 36 different targets or assay types of interest, and different test samples can be applied to each of the 96 wells in each plate. The same set of anchors can be used multiple times to re-program the surface of the wells for other targets and assays of interest, or it can be re-used multiple times with the same set of linkers. This flexibility and reusability represent further advantages of the invention.

One embodiment of the invention is a combination useful for the detection of one or more target(s) in a sample, which comprises, before the addition of said sample, a) a surface, comprising multiple spatially discrete regions, at least two of which are substantially identical, each region comprising b) at least eight different oligonucleotide anchors, each in association with c) a bifunctional linker which has a first portion that is specific for the oligonucleotide anchor, and a second portion that comprises a probe which is specific for said target(s).

Another embodiment of the invention is a combination useful for the detection of one or more target(s) in a sample, which comprises, before the addition of said sample, a) a surface, comprising multiple spatially discrete regions, at least two of which are substantially identical, each region comprising b) at least eight different anchors, each in association with c) a bifunctional linker which has a first portion that is specific for the anchor, and a second portion that comprises a probe which is specific for said target(s).

Another embodiment of the invention is a method for detecting at least one target, which comprises contacting a sample which may comprise the target(s) with a combination as described above, under conditions effective for said target(s) to bind to said combination. Another embodiment is a method for determining an RNA expression pattern, which comprises incubating a sample which comprises as target(s) at least two RNA molecules with a combination as described above, wherein at least one probe of the combination is a nucleic acid (e.g., oligonucleotide) which is specific (i.e. selective) for at least one of the RNA targets, under conditions which are effective for specific hybridization of the RNA target(s) to the probe(s). Another embodiment is a method for identifying an agent (or condition(s)) that modulates an RNA expression pattern, which is the method described above for determining an RNA expression pattern, further comprising comparing the RNA expression pattern produced in the presence of said agent (or condition(s)) to the RNA expression pattern produced under a different set of conditions.

By way of example, FIGS. 1 and 2 illustrate a combination of the invention and a method of using it to detect an mRNA target. The surface of the invention, shown in FIG. 2, contains 15 identical test regions; in an especially preferred embodiment of the invention, each of these test regions is a well in a microtiter plate. Each of the test regions contains six different anchors, here indicated as numbers 1-6. FIG. 1 schematically illustrates one of those anchors, anchor 1, which, in a most preferred embodiment of the invention, is an oligonucleotide. To anchor 1 is attached a linker molecule, linker 1, which comprises two portions. The first portion, which is specific for the anchor, is in this illustration an oligonucleotide which can hybridize specifically to the anchor. The second portion, which is a probe specific for the target of interest—here, target mRNA 1—is in this illustration an oligonucleotide which can hybridize to that target. Although not illustrated in this figure, each of the remaining five anchors can hybridize to its own linker via the anchor-specific portion; each linker can contain a probe portion specific for, e.g., an mRNA different from (or the same as) mRNA 1. This illustrated combination can be used to assay as many as 15 different samples at the same time for the presence of mRNA 1 (or, simultaneously, for mRNA targets which are-specified (programmed) by the other five probes in the array). To perform the assay, each sample, which in this example can be an RNA extract from, say, one of 15 independent cell lines, is added in a small volume to one of the regions, or wells, and incubated under conditions effective for hybridization of the probe and the target. In order to determine if mRNA 1 is present in a sample, a detection device which can recognize patterns, and/or can interrogate specific locations within each region for the presence of a signal, is employed. If the cell lines are incubated under conditions in which their mRNAs are labeled in vivo with a tag, and if mRNA 1 is present in a sample, the detector will detect a signal emanating from the tagged mRNA at the location defined by anchor/probe complex 1. Alternatively, the mRNA can be directly labeled in vitro, before or after being added to the regions (wells). Alternatively, as is illustrated in FIG. 1, mRNA can be tagged indirectly, before or after it has hybridized to the probe, e.g., by incubating the RNA with a tagged "detector" oligonucleotide (target-specific reporter oligonucleotide) which is complementary to a sequence other than that recognized by the probe. In the illustrated example, 15 samples can be analyzed simultaneously. Because at least 20 or more, e.g. as many as 1536 or more, samples can be analyzed simultaneously with this invention, it is a very high throughput assay system.

As used herein, "target" refers to a substance whose presence, activity and/or amount is desired to be determined and which has an affinity for a given probe. Targets can be man-made or naturally-occurring substances. Also, they can be employed in their unaltered state or as aggregates with other species. Targets can be attached, covalently or noncovalently, to a binding member, either directly or via a specific binding substance. Examples of targets which can be employed in this invention include, but are not limited to, receptors (on vesicles, lipids, cell membranes or a variety of other receptors); ligands, agonists or antagonists which bind to specific receptors; polyclonal antibodies, monoclonal antibodies and antisera reactive with specific antigenic determinants (such as on viruses, cells or other materials); drugs; nucleic acids or polynucleotides (including mRNA, tRNA, rRNA, oligonucleotides, DNA, viral RNA or DNA, ESTs, cDNA, PCR-amplified products derived from RNA or DNA, and mutations, variants or modifications thereof); proteins (including enzymes, such as those responsible for cleaving neurotransmitters, proteases, kinases and the like); substrates for enzymes; peptides; cofactors; lectins; sugars; polysaccharides; cells (which can include cell surface antigens); cellular membranes; organelles; etc., as well as other such molecules or other substances which can exist in complexed, covalently bonded crosslinked, etc. form. As used herein, the terms nucleic acid, polynucleotide, polynucleic acid and oligonucleotide are interchangeable. Targets can also be referred to as anti-probes.

As used herein, a "probe" is a substance, e.g., a molecule, that can be specifically recognized by a particular target. The types of potential probe/target or target/probe binding partners include receptor/ligand; ligand/antiligand; nucleic acid (polynucleotide) interactions, including DNA/DNA, DNA/RNA, PNA (peptide nucleic acid)/nucleic acid; enzymes, other catalysts, or other substances, with substrates, small molecules or effector molecules; etc. Examples of probes that are contemplated by this invention include, but are not limited to, organic and inorganic materials or polymers, including metals, chelating agents or other compounds which interact specifically with metals, plastics, agonists and antagonists for cell membrane receptors, toxins and venoms, viral epitopes, hormones (e.g., opioid peptides, steroids, etc.), hormone receptors, lipids (including phospholipids), peptides, enzymes (such as proteases or kinases), enzyme substrates, cofactors, drugs, lectins, sugars, nucleic acids (including oligonucleotides, DNA, RNA, PNA or modified or substituted nucleic acids), oligosaccharides, proteins, enzymes, polyclonal and monoclonal antibodies, single chain antibodies, or fragments thereof. Probe polymers can be linear or cyclic. Probes can distinguish between phosphorylated and non-phosphorylated proteins, either by virtue of differential activity or differential binding. Probes such as lectins can distinguish among glycosylated proteins. As used herein, the terms nucleic acid, polynucleotide, polynucleic acid and oligonucleotide are interchangeable. Any of the substances described above as "probes" can also serve as "targets," and vice-versa.

Any compatible surface can be used in conjunction with this invention. The surface (usually a solid) can be any of a variety of organic or inorganic materials or combinations thereof, including, merely by way of example, plastics such as polypropylene or polystyrene; ceramic; silicon; (fused) silica, quartz or glass, which can have the thickness of, for example, a glass microscope slide or a glass cover slip; paper, such as filter paper; diazotized cellulose; nitrocellulose filters; nylon membrane; or polyacrylamide or other type of gel pad, e.g., an aeropad or aerobead, made of an aerogel, which is, e.g., a highly porous solid, including a film, which is prepared by drying of a wet gel by any of a variety of routine, conventional methods. Substrates that are transparent to light are useful when the method of performing an assay involves optical detection. The surface can be of any thickness or opacity which is compatible with, e.g., conventional methods of detection. For example, the surface can be a thick bottom, clearplate, or an opaque plate. In a preferred embodiment, the surface is the plastic surface of a multiwell, e.g., tissue culture dish, for example a 24-, 96-, 256-, 384-, 864- or 1536-well plate (e.g., a modified plate such as a Corning Costar DNA Bind plate). Anchors can be associated, e.g., bound, directly with a surface, or can be associated with one type of surface, e.g., glass, which in turn is placed in contact with a second surface, e.g., within a plastic "well" in a microtiter dish. The shape of the surface is not critical. It can, for example, be a flat surface such as a square, rectangle, or circle; a curved surface; or a three dimensional surface such as a bead, particle, strand, precipitate, tube, sphere; etc.

The surface comprises regions which are spatially discrete and addressable or identifiable. Each region comprises a set of anchors. How the regions are separated, their physical characteristics, and their relative orientation to one another are not critical. In one embodiment, the regions can be separated from one another by any physical barrier which is resistant to the passage of liquids. For example, in a preferred embodiment, the regions can be wells of a multiwell (e.g., tissue culture) dish, for example a 24-, 96-, 256-, 384-, 864- or 1536-well plate. Alternatively, a surface such as a glass surface can be etched out to have, for example, 864 or 1536 discrete, shallow wells. Alternatively, a surface can comprise regions with no separations or wells, for example a flat surface, e.g., piece of plastic, glass or paper, and individual regions can further be defined by overlaying a structure (e.g,. a piece of plastic or glass) which delineates the separate regions. Optionally, a surface can already comprise one or more arrays of anchors, or anchors associated with linkers, before the individual regions are delineated. In another embodiment, arrays of anchors within each region can be separated from one another by blank spaces on the surface in which there are no anchors, or by chemical boundaries, such as wax or silicones, to prevent spreading of droplets.

In yet another embodiment, the regions can be defined as tubes or fluid control channels, e.g., designed for flow-through assays, as disclosed, for example, in Beattie et al (1995). *Clin. Chem.* 4, 700-706. Tubes can be of any size, e.g., capillaries or wider bore tubes; can allow the flow of liquids; or can be partially or completely filled with a gel, e.g., agarose or polyacrylamide, through which compounds can be transported (passed through, flowed through, pumped through), e.g., by electrophoresis; or with a space filling matrix of channels, e.g., of linear channels, as described, e.g., in Albota et al. (1998). *Science* 281, 1653-1656; Cumpston et al. (1998). *Mat. Res. Soc. Symp. Proc.* 488, 217-225; and/or Cumpston et al. (1999). *Nature* 398, 51-54. In such a space-filling matrix, liquid and/or molecules therein can not only follow in direction perpendicular to the wall of the tube, but can also diffuse laterally. In a preferred embodiment, a tube is filled with a gel or space-filling matrix; the gel or space-filling matrix is activated for the binding of anchors, and different anchors are passed through sequentially, allowing the formation of a an array (e.g., a linear array) of anchors within the gel; and linkers, targets, etc. are passed through in succession. The array may be linear, 2- or 3-dimensional.

A plurality of assays can be performed in a single tube. For example, a single array of anchors, or of anchors in association with linkers, in a tube can be re-used (e.g., stripped and re-used, or reprogrammed) in sequential assays with the same or different samples. In another embodiment, a plurality of tubes is used in a single assay, e.g., a sample of interest is analyzed in a plurality of tubes containing different arrays. The anchors and anchor/linker associations in the tubes can be any of the types described elsewhere herein.

Regions within or on, etc. a surface can also be defined by modification of the surface itself. For example, a plastic surface can comprise portions made of modified or derivatized plastic, which can serve, e.g., as sites for the addition of specific types of polymers (e.g., PEG can be attached to a polystyrene surface and then derivatized with carboxyl or amino groups, double bonds, aldehydes, and the like). Alternatively, a plastic surface can comprise molded structures such as protrusions or bumps, which can serve as platforms for the addition of anchors. In another embodiment, regions can be gel pads, e.g., polyacrylamide gel pads or aeropads, which are arrayed in a desired pattern on a surface such as, e.g., glass, or are sandwiched between two surfaces, such as, e.g., glass and a quartz plate. Anchors, linkers, etc. can be immobilized on the surface of such pads, or can be imbedded within them. A variety of other arrangements of gel pads on surfaces will be evident to one of skill in the art, and can be produced by routine, conventional methods. The relative orientation of the test regions can take any of a variety of forms including, but not limited to, parallel or perpendicular arrays within a square or rectangular or other surface, radially extending arrays within a circular or other surface, or linear arrays, etc.

The spatially discrete regions of the invention are present in multiple copies. That is, there are at least two, preferably at least twenty, or at least about 24, 50, 96, 256, 384, 864, 1536, 2025, or more, etc., substantially identical, spatially discrete (separated) regions. Increasing numbers of repeated regions can allow for assays of increasingly higher throughput. Substantially identical regions, as used herein, refers to regions which contain identical or substantially identical arrays of anchors and/or anchor/linker complexes. Substantially identical, as used herein, means that an array or region is intended to serve essentially the same function as another array or region in the context of analyzing a target in accordance with this invention. Differences not essentially affecting function, i.e., detectability of targets, are along the line of small nucleotide imperfections (omissions/inserts/substitutions) or oligo imperfections (poor surface binding), etc., which do not within assay accuracy significantly affect target determination results.

Of course, one of skill in the art will recognize that not all of the regions on a surface need to be substantially identical to one another. For example, if two different sets of arrays are to be tested in parallel, it might be advantageous to include both sets of arrays on a single surface. For example, the two different sets of arrays can be arranged in alternating striped patterns, to facilitate comparison between them. In another embodiment, the practitioner may wish to include regions which can be detected in a distinguishable manner from the other regions on the surface and can thereby be used as a "registration region(s)." For example, a registration region can comprise oligonucleotides or peptides which display a distinctive pattern of fluorescent molecules that can be recognized by a scanning detection device as a "starting point" for aligning the locations of the regions on a surface.

The size and physical spacing of the test regions are not limiting. Typical regions are of an area of about 1 to about 700 mm², preferably 1 to about 40 mm², and are spaced about 0.5 to about 5 mm apart, and are routinely selected depending on the areas involved. In a preferred embodiment, the regions are spaced approximately 5 mm apart. For example, each region could comprise a rectangular grid, with, for example, 8 rows and 6 columns, of roughly circular spots of anchors which are about 100 micrometers in diameter and 500 micrometers apart; such a region would cover about a 20 millimeter square area. Larger and smaller region areas and spacings are included.

The regions can also be further subdivided such that some or all anchors within a region are physically separated from neighboring anchors by means, e.g., of an indentation or dimple. For example, the number of subdivisions (subregions) in a region can range from about 10 to about 100 or more or less. In one embodiment, a region which is a well of a 1536-well dish can be further subdivided into smaller wells, e.g., about 4 to about 900, preferably about 16 to about 36 wells, thereby forming an array of wells-within-wells. See FIG. 4. Such a dimpled surface reduces the tolerance required for physically placing a single anchor (or group of anchors) into each designated space (locus), and the size of the areas containing anchors is more uniform, thereby facilitating the detection of targets which bind to the probe.

The term "anchor" as used herein refers to any entity or substance, e.g., molecule, which is associated with (e.g., immobilized on, or attached either covalently or non-covalently to) the surface, or which is a portion of such surface (e.g., derivatized portion of a plastic surface), and which can undergo specific interaction or association with a linker or other substance as described herein. The portion of an anchor which associates with, e.g., a linker molecule, can be associated with the surface directly, or the anchor can comprise an intermediate "spacer" moiety. Such a spacer can be of any material, e.g., any of a variety of materials which are conventional in the art. In one embodiment, the spacer is a linear carbon molecule having, e.g., about 5-20 Cs, preferably about 12 Cs. In another embodiment, the spacer is a nucleic acid (of any of the types describes elsewhere herein) which does not undergo specific interaction or association with, e.g., a linker molecule.

The term "anchor" as used herein can also refer to a group of substantially identical anchors. See, e.g., FIG. 7, which schematically represents a test region comprising 3 anchors (A, B and C), each of which is present in multiple copies (a "group"). The location of each group of anchors is termed herein a "locus." As is well known in the art, the number of individual anchor molecules present at a locus is limited only by physical constraints introduced by, e.g., the size of the anchors. For example, a locus which is, e.g., about 25-200 µm in diameter, can comprise millions of anchors.

As used herein, an "anchor/linker complex" exists when an anchor and a linker have combined through molecular association in a specific manner. The interaction with the linker can be either irreversible, such as via certain covalent bonds, or reversible, such as via nucleic acid hybridization.

In a preferred embodiment, the anchor is a nucleic acid, which can be of any length (e.g., an oligonucleotide) or type (e.g., DNA, RNA, PNA, or a PCR product of an RNA or DNA molecule). The nucleic acid can be modified or substituted (e.g., comprising non naturally occurring nucleotides such as, e.g., inosine; joined via various known linkages such as sulfamate, sulfamide, phosphorothionate, methylphosphonate, carbamate, etc.; or a semisynthetic molecule such as a DNA-streptavidin conjugate, etc.). Single stranded nucleic acids are preferred.

A nucleic acid anchor can be of any length which is compatible with the invention. For example, the anchor can be an oligonucleotide, ranging from about 8 to about 50 nucleotides in length, preferably about 10, 15, 20, 25 or 30 nucleotides. In another embodiment, the anchor can be as long as about 50 to about 300 nucleotides in length, or longer or shorter, preferably about 200 to about 250 nucleotides. For example, an anchor can comprise about 150 to about 200 nucleotides of "spacer" nucleic acid, as described above, and, adjacent to the spacer, a shorter sequence of, e.g., about 10, 15, 20, 25 or 30 nucleotides which is designed to interact with a linker molecule ("linker-specific sequence"). Such spacers can be of any length or type of nucleic acid, and can have any base composition which is functional in the invention. In a preferred embodiment, the spacers of each of the anchors at a locus, and/or of the anchors in different loci within a region, are substantially identical; the anchors thus differ from one another primarily with regard to their linker-specific sequences.

Spacers can impart advantages to anchors, allowing for improved performance. For example, the linker-specific portions of such an anchor lie further away from the surface, and therefore are less physically constrained and subject to less steric hindrance, than if they were closer to the surface. This facilitates, for example, the association of a plurality of different linkers (e.g., about 2 to about 100), having different target specificities, with the anchors at a given locus. As is discussed in more detail below, an individual anchor can comprises (in addition to a spacer) a plurality of linker-specific sequences which are arranged, e.g., in a tandem linear fashion; this allows for the association of a plurality of different types of linkers with at least one such anchor at a given locus. Also discussed in more detail below is another way in which a plurality of different types of linkers can be associated with the anchors at a given locus: at a "mixed locus," two or more anchors are each associated with a different linker, having a different target specificity. Because of the physical flexibility of anchors comprising spacers, the anchors at a given locus can readily bind to a plurality of different linker molecules without being physically constrained by adjacent anchor molecules. An advantage of binding a plurality of linker molecules to the anchors at a given locus is that it allows for the detection of an increased number of targets at a particular locus. In one embodiment, the plurality of linkers bound at a given locus have probes which are specific for different portions of the same target nucleic acid of interest (e.g., to different oligonucleotide sequences within the nucleic acid). This allows for amplified detection of the target compared to detection with a single probe. In another embodiment, the plurality of linkers have probes which are specific for different, e.g. unrelated, targets. This allows for the detection of a plurality of different targets within a particular locus. A further advantage of anchors comprising spacers is that they can more readily accommodate linkers which are associated with relatively large molecules such as, e.g., proteins, and/or which bind to relatively large targets such as, e.g., proteins, membranes or cells.

The base composition of a nucleic acid anchor is not necessarily constrained. Any base composition of the anchors is acceptable, provided that the anchors are functional for the purpose of the invention. For example, single stranded nucleic acid anchors at a locus, or at different loci in a region, can comprise partially or completely random sequences (e.g., randomly generated sequences, for example with no restrictions on the relative amounts of A, G, T and/or C). In one embodiment, the anchors are not "sequence isomers" (e.g., "random sequence isomers"), i.e., oligonucleotides having identical amounts of G, C, A and T, but arranged in different relative orders. That is, the anchors in, for example, the different loci of a region do not conform to the equation $G_n C_n A_m T_m$, where n and m are integers. See, e.g., the anchors shown in Example 1, which are not random sequence isomers. In the anchors of the invention, the amounts of G and C do not need to be approximately the same, nor do the relative amounts of A and T. Furthermore, the net relative amounts of G, C, A and T are not necessarily constrained. For example, the base composition of the anchors in a region can range from being relatively GC rich (i.e., greater than 50% G+C), to having equal amounts of G, C, A and T, to being relatively AT rich (i.e., greater than 50% A+T). In one embodiment, the anchors are randomly generated, e.g., in a manner such that no constraints are placed on the relative amounts of G, C, A and T.

Anchors comprising a nucleic acid spacer and one or more linker-specific portions are unlikely to conform to any particular constraints on base compostion. For example, if the anchors located at different loci in a region have spacers which are substantially identical, e.g., a substantially identical 25-mer or a 200-mer, but each anchor has a different linker-specific moiety (e.g., a 25-mer), even if the linker-specific moieties meet more specific requirements (e.g., the number of As and Gs are approximately equal; the number of Ts and Cs are approximately equal; the oligo conforms to the equation $G_n C_n A_m T_m$; and/or that the G+C content meets a particular requirement), the anchors as a whole will not meet those particular requirements. Similarly, even if the linker-specific moieties of anchors at different loci in a region are substantially different from one another (e.g., each linker-specific moiety has a sequence which differs by at least about 20%, or 50%, or 80% from each other linker-specific moiety in the region), the net sequence identities of the anchors, considering the entire length of the nucleic acid, may be far less. For example, if each of the anchors comprises a substantially identical 250-mer spacer, and a 25-mer linker-specific moiety which is 100% different from every other linker-specific moiety in the region, the anchors will still differ from one another by only 10%.

An anchor can also be a peptide or a protein. For example, it can be a polyclonal or monoclonal antibody molecule or fragment thereof, or single chain antibody or fragment thereof, which binds specifically to the portion of a linker that is an antigen or an anti-antibody molecule; in the obverse, the anchor can be a peptide, and the portion of the linker which binds to it can be an antibody or the like. In another embodiment, the anchor can be a lectin (such as concanavalin A or agglutinins from organisms such as Limulus, peanut, mung bean, Phaseolus, wheat germ, etc.) which is specific for a particular carbohydrate. In another embodiment, the anchor can comprise an organic molecule, such as a modified or derivatized plastic polymer which can serve, e.g., as the stage for specific solid phase chemical synthesis of an oligonucleotide. In this case, the derivatized plastic can be distributed as an array of discrete, derivatized, loci which are formed integrally into the plastic surface of a combination during the manufacturing process. In another embodiment, the anchor can take advantage of specific or preferential binding between metal ions, e.g., Ni, Zn, Ca, Mg, etc. and particular proteins or chelating agents. For example, the anchor can be polyhistidine, and the anchor-specific portion of the linker can be nickel, which is attached via a nickel chelating agent to a target-specific probe. Alternatively, the chelating agent can be the anchor and the polyhistidine the probe-related portion. Alternatively, the anchor can comprise an inorganic substance. For example, it can comprise a metal such as calcium or magnesium, and the anchor-specific portion of the linker can be a preferential chelating agent, such as EDTA or EGTA, respectively, which is attached to a target-specific probe. One of skill in the art will recognize that a wide range of other types of molecules can also serve as anchors, such as those general types also discussed in conjunction with probes and targets.

An anchor can also be a hybrid structure, such as a DNA duplex, or a duplex comprising, e.g., DNA and protein which interact specifically in any of the ways described elsewhere herein. For example, the "base moiety" of a duplex anchor (the portion which is in direct contact with the surface) can comprise an optionally modified single stranded nucleic acid; preferably, the base moiety also comprises a spacer, e.g., a linear carbon spacer as described above. In one embodiment, a second single stranded nucleic acid is associated with (e.g., hybridized to) this base moiety, to form an anchor which comprises at least a partially double stranded (duplex) nucleic acid. For example, the base moiety can comprise a linear carbon spacer which is attached to the surface at one end, and at the other end is attached to a single stranded DNA oligonucleotide of about 10-100 nucleotides, preferably about 25 nucleotides; and the second moiety of the duplex can comprise a sequence which is complementary to at least a portion of the base moiety, (e.g., to the terminal about 40 nucleotides), followed by an optional spacer (e.g., about 5-15, preferably about 10 nucleotides), followed by a linker-specific sequence (e.g., a sequence of about 8 to about 50 nucleotides, preferably about 15, 20, 25 or 30 nucleotides, most preferably about 25 nucleotides in length).

The relative lengths and base compositions of the complementary portions of an anchor duplex and of its linker-specific sequence(s) can be varied to suit the needs of an assay, using optimization procedures which are conventional in the art. For example, sequences can be selected such that linkers can be dissociated from (e.g., melted apart from) duplex anchor molecules under conditions in which the duplex anchors, themselves, remain intact. The remaining arrays of duplex anchors can then be re-used, if desired, to hybridize to the same or different linker molecules. Alternatively, sequences can be selected such that both the anchor/linker hybrids and the two complementary portions of the duplex anchors are dissociated under the same conditions, leaving behind only the base moieties in contact with the surface. In one embodiment, all or substantially all of the base moieties in a particular locus or in all the loci of a region are identical, or substantially identical. The arrays of base moieties remaining after such a dissociation can be re-used (e.g., for hybridization to linker molecules) only if the complementary portions of the duplex anchors are first added back, a process which requires knowledge of the sequence of the base moiety that is involved in duplex formation. The ability to manufacture arrays of anchors which either can or cannot be re-used by a user unfamiliar with the sequence of the base moieties, represents an advantage of employing such hybrid anchors. For example, a manufacturer can prevent unauthorized re-use of its arrays. The prevention of such re-use can also, e.g., forestall problems of degraded performance or unreliability occasioned by excessive use.

In one embodiment, the group of anchors at a given locus within a region are substantially identical (e.g., are specific for the "anchor-specific" portion of one type of linker, or for one target, only). See, e.g., FIG. 7. In another embodiment, a plurality of different anchors, having specificities for a plurality of different linkers and/or for a plurality of different targets, can be present at a given locus, called a "mixed locus," e.g., a plurality of about 2 to about 100, for example at least about 2, at least about 4 or at least about 10. An advantage of mixed loci is that they allow for the detection of an increased number of different targets at a particular locus. In one embodiment, each mixed locus contains one anchor which is the same in every, or at least several, loci. For instance, an anchor which is the same in more than one locus can be used for quality assurance and/or control or for signal normalization.

Of course, "mixed loci" are also advantageous for surfaces having only a single (non-repeated) region. The anchors in each of the loci of such a single region can interact with linkers, or directly with targets of interest.

The number of anchors (i.e., groups of anchors at individual loci) in a test region can be at least two, preferably between about 8 and about 900 (more or less being included), more preferably between about 8 and about 300, and most preferably between about 30 and about 100 (e.g., about 64). In some preferred embodiments, there are about 16, 36, 45 or 100 anchors/test region for a surface with 96 test regions (e.g., wells), or about 9, 16 or 25 anchors/test region for a surface with 384 test regions (e.g., wells). In a most preferred embodiment, each anchor in a test region has a different specificity from every other anchor in the array. However, two or more of the anchors can share the same specificity and all of the anchors can be identical. In one embodiment, in which a combination of the invention comprises a very large number of test regions (e.g., about 864, 1536, or more), so that a large number of test samples can be processed at one time, it might of interest to test those samples for only a limited number (e.g., about 2, 4, 6 or 9) of parameters. In other words, for combinations comprising a very large number of regions, it might be advantageous to have only about 2 to 9 anchors per region.

The physical spacing and relative orientation of the anchors (i.e., groups of anchors at individual loci) in or on a test region are not limiting. Typically, the distance between the anchors is about 0.003 to about 5 mm or less, preferably between about 0.03 and about 1. Larger and smaller anchor spacings (and areas) are included. The anchors can be arranged in any orientation relative to one another and to the boundaries of the region. For example, they can be arranged in a two-dimensional orientation, such as a square, rectangular, hexagonal or other array, or a circular array with anchors emanating from the center in radial lines or concentric rings. The anchors can also be arranged in a one-dimensional, linear array. For example, oligonucleotides can be hybridized to specific positions along a DNA or RNA sequence to form a supramolecular array, or in a linear arrangement in a flow through gel, or on the surface of a flow through device or structures within a flow through device Alternatively, the anchors can be laid down in a "bar-code"-like formation. (See FIG. 6). For example, anchors can be laid down as long lines parallel to one another. The spacing between or the width of each long line can be varied in a regular way to yield a simple, recognizable pattern much like a bar-code, e.g., the first and third lines can be twice as large as the rest, lines can be omitted, etc. An extra empty line can be placed after the last line to demarcate one test region, and the bar code pattern can be repeated in succeeding test regions.

The pattern of anchors does not need to be in strict registry with the positions of the separated assay wells (test regions) or separate assay droplets. The term "assay positions" will be used to refer to the positions of the assay surface where assay samples are applied. (These can be defined by the position of separate droplets of assay sample or by the position of walls or separators defining individual assay wells on a multi-well plate for example.) The anchor pattern itself (e.g., a "bar code"-like pattern of oligonucleotide anchors) is used to define where exactly each separate anchor is positioned by pattern recognition—just as each line of a barcode is recognized by its position relative to the remaining lines. Hence the first anchor need not be at one edge or one corner of each assay position. The first anchor will be found by pattern recognition, rather than position relative to the assay position. As long as the area used by each assay position (the area of the droplet or the area of the well for example) is large enough to be certain to contain at least one whole unit of the repeating pattern of anchors, then each assay point will test the sample for that assay position for all of the targets specified by the (bar-coded) pattern wherever the pattern lies within the area of the assay position.

The anchors do not need to be arranged in a strict or even fixed pattern within each test region. For example, each anchor can be attached to a particle, bead, or the like, which assumes a random position within a test region. The location of each anchor can be determined by the use, e.g., of a detectable tag. For example, the linker molecule specific for each type of anchor can be labeled with a different fluorescent, luminescent etc. tag, and the position of a particle comprising a particular linker/anchor pair can be identified by the nature of the signal emanating from the linker, e.g., the excitation or emission spectrum. One skilled in the art can prepare a set of linkers with a variety of such attached tags, each with a distinguishable spectrum. Alternatively, the anchors can be labeled directly. For example, each type of anchor can be labeled with a tag which fluoresces with a different spectrum from the tags on other types of anchors. Alternatively, the particles, beads or the like can be different from one another in size or shape. Any of the labeling and detection methods described herein can be employed. For example, fluorescence can be measured by a CCD-based imaging system, by a scanning fluorescence microscope or Fluorescence Activated Cell Sorter (FACS).

An anchor can interact or become associated specifically with one portion—the anchor-specific portion—of a linker molecule. By the terms "interact" or "associate", it is meant herein that two substances or compounds (e.g., anchor and anchor-specific portion of a linker, a probe and its target, or a target and a target-specific reporter) are bound (e.g., attached, bound, hybridized, joined, annealed, covalently linked, or otherwise associated) to one another sufficiently that the intended assay can be conducted. By the terms "specific" or "specifically", it is meant herein that two components (e.g., anchor and anchor-specific region of a linker, a probe and its target, or a target and a target-specific reporter) bind selectively to each other and, in the absence of any protection technique, not generally to other components unintended for binding to the subject components. The parameters required to achieve specific interactions can be determined routinely, e.g., using conventional methods in the art.

For nucleic acids, for example, one of skill in the art can determine experimentally the features (such as length, base composition, and degree of complementarity) that will enable a nucleic acid (e.g., an oligonucleotide anchor) to hybridize to another nucleic acid (e.g., the anchor-specific portion of a linker) under conditions of selected stringency, while minimizing non-specific hybridization to other substances or molecules (e.g., other oligonucleotide linkers). Typically, the DNA or other nucleic acid sequence of an anchor, a portion of a linker, or a detector oligonucleotide will have sufficient complementarity to its binding partner to enable it to hybridize under selected stringent hybridization conditions, and the $T_m$ will be about 10° to 20° C. above room temperature (e.g., about 37° C.). In general, an oligonucleotide anchor can range from about 8 to about 50 nucleotides in length, preferably about 15, 20, 25 or 30 nucleotides. As used herein, "high stringent hybridization conditions" means any conditions in which hybridization will occur when there is at least 95%, preferably about 97 to 100%, nucleotide complementarity (identity) between the nucleic acids. However, depending on the desired purpose, hybridization conditions can be selected which require less complementarity, e.g., about 90%, 85%, 75%, 50%, etc. Among the hybridization reaction parameters which can be varied are salt concentration, buffer, pH, temperature, time of incubation, amount and type of denaturant such as formamide, etc. (see, e.g., Sambrook et al. (1989). *Molecular Cloning: A Laboratory Manual* (2d ed.) Vols. 1-3, Cold Spring Harbor Press, New York; Hames et al. (1985). *Nucleic Acid Hybridization*, IL Press; Davis et al. (1986), *Basic Methods in Molecular Biology*, Elsevier Sciences Publishing, Inc., New York). For example, nucleic acid (e.g., linker oligonucleotides) can be added to a test region (e.g., a well of a multiwell plate—in a preferred embodiment, a 96 or 384 or greater well plate), in a volume ranging from about 0.1 to about 100 or more μl (in a preferred embodiment, about 1 to about 50 μl, most preferably about 40 μl), at a concentration ranging from about 0.01 to about 5 μM (in a preferred embodiment, about 0.1 μM), in a buffer such as, for example, 6×SSPE-T (0.9 M NaCl, 60 mM $NaH_2PO_4$, 6 mM EDTA and 0.05% Triton X-100), and hybridized to a binding partner (e.g. an oligonucleotide anchor on the surface) for between about 10 minutes and about at least 3 hours (in a preferred embodiment, at least about 15 minutes) at a temperature ranging from about 4° C. to about 37° C. (in a preferred embodiment, at about room temperature). Conditions can be chosen to allow high throughput. In one embodiment of the invention, the reaction conditions can approximate physiological conditions.

The design of other types of substances or molecules (e.g., polypeptides, lectins, etc.) which can, e.g., serve as anchors or as portions of linkers, and the reaction conditions required to achieve specific interactions with their binding partners, are routine and conventional in the art (e.g., as described in Niemeyer et al (1994). *Nucl. Acids Res.* 22, 5530-5539; Fodor et al (1996). U.S. Pat. No. 5,510,270; Pirrung et al (1992), U.S. Pat. No. 5,143,854). Among the incubation parameters are buffer, salt concentration, pH, temperature, time of incubation, presence of carrier and/or agents or conditions to reduce non-specific interactions, etc. For example, to a test region (e.g., a well of a multiwell plate—in a preferred embodiment, a 96 or 384 or greater well plate) which contains, as anchors, antibodies, can be added anti-antibodies (e.g., antigens or antibody-specific secondary antibodies) in a volume ranging from about 0.1 to about 100 or more μl (in a preferred embodiment, about 1 to about 50 μl, most preferably about 40 μl), at a concentration ranging from about 10 pM to about 10 nM (in a preferred embodiment, about 1 nM), in a buffer such as, for example, 6×SSPE-T, PBS or physiological saline, and incubated with the anchors on the surface for between about 10 minutes and at least about 3 hours (in a preferred embodiment, at least about 15 minutes), at a temperature ranging from about 4° C. to about 45° C. (in a preferred embodiment, about 4° C.). For peptide anchors, a length of about 5 to about 20 amino acids is preferred.

In some embodiments of the invention, each anchor in an array can interact with the anchor-specific portion of its corresponding linker to substantially the same degree as do the other anchors in the array, under selected reaction conditions. This can insure that the anchors specify a substantially uniform array of linkers and, therefore, probes.

The anchors (i.e., groups of anchors at individual loci) within a test region can be a "generic" set, each anchor of which can interact with one or more of a variety of different linkers, each having a portion specific to such anchor but with differing "probe" portions; thus, a single array of generic anchors can be used to program or define a varied set of probes. The flexible nature of such a generic assay of anchors can be illustrated with reference to FIGS. 1 and 2. FIG. 2 illustrates a surface which comprises 15 test regions, each of which contains an array of 6 different anchors, which in this example can be oligonucleotides. FIG. 1 schematically illustrates one of these (oligonucleotide) anchors, anchor 1, which is in contact with linker 1, which comprises one portion that is specific for anchor 1 and a second portion that is specific for target mRNA 1. Alternatively, one could substitute, e.g., a linker 2, which, like linker 1, comprises a portion that is specific for anchor 1, but which comprises a second portion that is specific for target mRNA 2 instead of target mRNA 1. Thus, anchor 1 can be used to specify (or program, or define, or determine) probes for either of two or more different target mRNAs. The process of generating and attaching a high resolution pattern (array) of oligonucleotides or peptides can be expensive, time-consuming and/or physically difficult. The ability to use a preformed array of anchors to program a wide variety of probe arrays is one advantage of this invention.

Although the generic anchors illustrated in FIG. 2 define a pattern of oligonucleotide probes, the identical anchor array could also be used to program an array of other probes, for example receptor proteins (see, e.g., FIG. 3). Clearly, many permutations are possible, given the range of types of anchor/linker interactions, e.g., even more complex layers of "sandwiched" or "piggybacked" probes such as protein/antibody combinations. For example, in one embodiment a generic set of anchors can be associated (covalently or non-covalently) with a set of linkers to form a modified array of "conjugated" anchors, as is described in more detail below. Thus, the surface of anchors per this invention, itself, offers novel advantages.

In one embodiment of the invention, anchors can interact reversibly with linkers; thus, a generic set of anchors can be re-used to program a varied set of probes. For example, an oligonucleotide anchor can be separated from the oligonucleotide portion of a linker by, for example, a heating step that causes the two oligonucleotides to dissociate, and can then be rebound to a second linker. The ability to re-use anchor arrays, which can be expensive, time-consuming and/or physically difficult to make, is another advantage of the invention.

An anchor does not necessarily have to interact with a linker. For example, an anchor can be coupled (directly or indirectly) to a detectable molecule, such as a fluorochrome, and can thereby serve to localize a spot within a grid, e.g., for purpose of registration between the test surface and the detector. Alternatively, an anchor can be labeled with a known amount of a detectable molecule so as to serve as internal quantitation marker, e.g., for purposes of calibration.

The term "linker" as used herein refers to a bifunctional substance which comprises a first portion (or moiety or part) that is specific for a chosen (designated) anchor or subset of the anchors ("anchor-specific") and a second portion that comprises a probe which is specific for a target of interest ("target-specific"). The two portions of the linker can be attached via covalent or noncovalent linkages, and can be attached directly or through an intermediate (e.g., a spacer).

The chemical nature of the anchor-specific portion of the linker is, of course, a function of the anchor or anchors with which it interacts. For example, if the anchor is an oligonucleotide, the portion of the linker which interacts with it can be, for example, a peptide which binds specifically to the oligonucleotide, or a nucleic acid which can hybridize efficiently and specifically to it under selected stringent hybridization conditions. The nucleic acid can be, e.g., an oligonucleotide, DNA, RNA, PNA, PCR product, or substituted or modified nucleic acid (e.g., comprising non naturally-occurring nucleotides such as, e.g., inosine; joined via various known linkages such as sulfamate, sulfamide, phosphorothionate, methylphosphonate, carbamate; or a semisynthetic molecule such as a DNA-streptavidin conjugate, etc.). Single strand moieties are preferred. The portion of a linker which is specific for an oligonucleotide anchor can range from about 8 to about 50 nucleotides in length, preferably about 15, 20, 25 or 30 nucleotides. If the anchor is an antibody, the portion of the linker which interacts with it can be, e.g., an anti-antibody, an antigen, or a smaller fragment of one of those molecules, which can interact specifically with the anchor. Substances or molecules which interact specifically with the other types of anchors described above, and which can serve as the anchor-specific portion of a linker, are well-known in the art and can be designed using conventional procedures (e.g., see above).

The chemical nature of the target-specific portion of the linker is, of course, a function of the target for which it is a probe and with which it interacts. For example, if the target is a particular mRNA, the target-specific portion of the linker can be, e.g., an oligonucleotide which binds specifically to the target but not to interfering RNAs or DNAs, under selected hybridization conditions. One of skill in the art can, using art-recognized methods, determine experimentally the features of an oligonucleotide that will hybridize optimally to the target, with minimal hybridization to non-specific, interfering DNA or RNA (e.g., see above). In general, the length of an oligonucleotide probe used to distinguish a target mRNA present in a background of a large excess of untargeted RNAs can range from about 8 to about 50 nucleotides in length, preferably about 18, 20, 22 or 25 nucleotides. An oligonucleotide probe for use in a biochemical assay in which there is not a large background of competing targets can be shorter. Using art-recognized procedures (e.g., the computer program BLAST), the sequences of oligonucleotide probes can be selected such that they are mutually unrelated and are dissimilar from potentially interfering sequences in known genetics databases. The selection of hybridization conditions that will allow specific hybridization of an oligonucleotide probe to an RNA can be determined routinely, using art-recognized procedures (e.g., see above). For example, target RNA [e.g., total RNA or mRNA extracted from tissues or cells grown (and optionally treated with an agent of interest) in any vessel, such as the well of a multiwell microtiter plate (e.g., 96 or 384 or more wells)] can be added to a test region containing a oligonucleotide probe array (see above) in a buffer such as 6×SSPE-T or others, optionally containing an agent to reduce non-specific binding (e.g., about 0.5 mg/ml degraded herring or salmon sperm DNA, or yeast RNA), and incubated at an empirically determined temperature for a period ranging from between about 10 minutes and at least 18 hours (in a preferred embodiment, about 3 hours). The stringency of the hybridization can be the same as, or less than, the stringency employed to associate the anchors with the anchor-specific portion of the linkers. The design and use of other types of probes are also routine in the art, e.g., as discussed above.

In one embodiment, all, or substantially all, of the linkers associated with the anchors at a given locus contain an identical (or substantially identical) probe, which is specific for a single, specific target of interest. In another embodiment, one or more of the linkers associated with the anchors at a given locus comprises a plurality of different probes, and thus is specific for a plurality of different targets. These probes can be situated in the linker as part of a branched structure, or preferably, can be aligned in a linear relationship; and they can be of the same material (e.g., are all nucleic acid or are all peptide sequences), or combinations of various materials. In effect, having multiple probes on each-linker increases the number of targets which can be detected at a particular locus. In one embodiment, a plurality of probes on given linker are all specific for a particular target of interest (e.g., they are specific for different portions of a single mRNA of interest, or are specific for nuclease protection fragments corresponding to different portions of that mRNA); this allows for increased sensitivity of an assay for the target, e.g., a target which is present in a sample at low abundance. The number of probes on a linker can be, e.g., about 2-50, preferably about 2, 4 or 10.

Of course, linkers which comprise such a plurality of different probes are also advantageous for use with surfaces that contain only a single (non-repeated) region.

The anchor-specific and the target-specific portions of a linker can be joined (attached, linked) by any of a variety of covalent or non-covalent linkages, the nature of which is not essential to the invention. The two portions can be joined directly or through an intermediate molecule. In one embodiment, in Which both portions of the linker are oligonucleotides, they can be joined by covalent linkages such as phosphodiester bonds to form a single, colinear nucleic acid. In another embodiment, in which the anchor-specific portion is an oligonucleotide and the target-specific portion is a receptor, for example a receptor protein, the two portions can be joined via the interaction of biotin and streptavidin molecules, an example of which is illustrated in FIG. 3. Many variations of such linkages are known (e.g., see Niemeyer et al (1994). NAR 22, 5530-5539). Alternatively, the two portions can be joined directly, e.g., an oligonucleotide can be amidated and then linked directly (e.g., crosslinked) to a peptide or protein via an amide bond, or joined to a membrane component via an amide bond or a lipid attachment. Methods to form such covalent or noncovalent bonds are conventional and are readily optimized by one of skill in the art. Spacer sequences (e.g., nucleic acid) can also be present between the anchor-specific and target-specific portions of a linker.

After two substances are associated (e.g., by incubation of two nucleic acids, two proteins, a protein plus a nucleic acid, or others) to form a complex (such as, e.g., an anchor/linker complex), the resulting complex can be optionally treated (e.g., washed) to remove unbound substances (e.g., linkers), using conditions which are determined empirically to leave specific interactions intact, but to remove non-specifically bound material. For example, reaction mixtures can be washed between about one and ten times or more under the same or somewhat more stringent conditions than those used to achieve the complex (e.g., anchor/linker complex).

One of skill in the art will recognize that a variety of types of sandwiches of anchors and linkers can be generated. For example, to an array of anchors (e.g., anchors having substantially identical sequences), one can attach a first set of linkers, each of which has a first moiety that is specific for the anchor and a second moiety that is specific for one of a second set of linkers, and so forth. In effect, this second layer of a sandwich allows one to convert a first set of anchors (e.g., identical oligonucleotides) to a different array having a different set of specificities, of "conjugated" anchors. The various sets of linkers and anchors can be associated to one another covalently or non-covalently, as desired.

The combinations of this invention can be manufactured routinely, using conventional technology.

Some of the surfaces which can be used in the invention are readily available from commercial suppliers. In a preferred embodiment, the surface is a 96-, 384- or 1536-well microtiter plate such as modified plates sold by Corning Costar. Alternatively, a surface comprising wells which, in turn, comprise indentations or "dimples" can be formed by micromachining a substance such as aluminum or steel to prepare a mold, then microinjecting plastic or a similar material into the mold to form a structure such as that illustrated in FIG. 4. Alternatively, a structure such as that shown in FIG. 4, comprised of glass, plastic, ceramic, or the like, can be assembled, e.g., from three pieces such as those illustrated in FIG. 5: a first section, called a well separator (FIG. 5a), which will form the separations between the sample wells; a second section, called a subdivider (FIG. 5b), which will form the subdivisions, or dimples, within each test well; and a third section, called a base (FIG. 5c), which will form the base of the plate and the lower surface of the test wells. The separator can be, for example, a piece of material, e.g., silicone, with holes spaced throughout, so that each hole will form the walls of a test well when the three pieces are joined. The subdivider can be, for example, a thin piece of material, e.g., silicone, shaped in the form of a screen or fine meshwork. The base can be a flat piece of material, e.g., glass, in, for example, the shape of the lower portion of a typical microplate used for a biochemical assay. The top surface of the base can be flat, as illustrated in FIG. 5c, or can be formed with indentations that will align with the subdivider shape to provide full subdivisions, or wells, within each sample well. The three pieces can be joined by standard procedures, for example the procedures used in the assembly of silicon wafers.

Oligonucleotide anchors, linker moieties, or detectors can be synthesized by conventional technology, e.g., with a commercial oligonucleotide synthesizer and/or by ligating together subfragments that have been so synthesized. Nucleic acids which are too long to be comfortably synthesized by such methods can be generated by amplification procedures, e.g., PCR, using conventional procedures. In one embodiment of the invention, preformed nucleic acid anchors, such as oligonucleotide anchors, can be situated on or within the surface of a test region by any of a variety of conventional techniques, including photolithographic or silkscreen chemical attachment, disposition by ink jet technology, capillary, screen or fluid channel chip, electrochemical patterning using electrode arrays, contacting with a pin or quill, or denaturation followed by baking or UV-irradiating onto filters (see, e.g., Rava et al (1996). U.S. Pat. No. 5,545,531; Fodor et al (1996). U.S. Pat. No. 5,510,270; Zanzucchi et al (1997). U.S. Pat. No. 5,643,738; Brennan (1995). U.S. Pat. No. 5,474,796; PCT WO 92/10092; PCT WO 90/15070). Anchors can be placed on top of the surface of a test region or can be, for example in the case of a polyacrylamide gel pad, imbedded within the surface in such a manner that some of the anchor protrudes from the surface and is available for interactions with the linker. In a preferred embodiment, preformed oligonucleotide anchors are derivatized at the 5' end with a free amino group; dissolved at a concentration routinely determined empirically (e.g., about 1 µM) in a buffer such as 50 mM phosphate buffer, pH 8.5 and 1 mM EDTA; and distributed with a Pixus nanojet dispenser (Cartesian Technologies) in droplets of about 10.4 nanoliters onto specific locations within a test well whose upper surface is that of a fresh, dry DNA Bind plate (Corning Costar). Depending on the relative rate of oligonucleotide attachment and evaporation, it may be required to control the humidity in the wells during preparation. In another embodiment, oligonucleotide anchors can be synthesized directly on the surface of a test region, using conventional methods such as, e.g., light-activated deprotection of growing oligonucleotide chains (e.g., in conjunction with the use of a site directing "mask") or by patterned dispensing of nanoliter droplets of deactivating compound using a nanojet dispenser. Deprotection of all growing sequences that are to receive a single nucleotide can be done, for example, and the nucleotide then added across the surface. In another embodiment, oligonucleotide anchors are attached to the surface via the 3' ends of the oligonucleotides, using conventional methodology.

Peptides, proteins, lectins, chelation embodiments, plastics and other types of anchors or linker moieties can also be routinely generated, and anchors can be situated on or within surfaces, using appropriate available technology (see, e.g., Fodor et al (1996). U.S. Pat. No. 5,510,270; Pirrung et al (1992). U.S. Pat. No. 5,143,854; Zanzucchi et al (1997). U.S. Pat. No. 5,643,738; Lowe et a! (1985). U.S. Pat. No. 4,562,157; Niemeyer et al (1994). NAR 22, 5530-5539).

In some embodiments of the invention, the disclosed combinations are used in a variety of screening procedures and/or to obtain information about the level, activity or structure of the probes or target molecules. Such assays are termed Multi Array Plate Screen (MAPS) methods or assays, and the surfaces comprising arrays of anchors or anchors plus probes which are used for the assays are termed MAPS arrays or MAPS plates.

The components of a reaction mixture, assay, or screening procedure can be assembled in any order. For example, the anchors, linkers and targets can be assembled sequentially; or targets and linkers, in the presence or absence of reporters, can be assembled in solution and then contacted with the anchors.

One embodiment of the invention relates to a method of detecting at least one target, comprising a) contacting a sample which may comprise said target(s) with a bifunctional linker which has a first portion that is specific for an oligonucleotide anchor and a second portion that comprises a probe which is specific for said target(s), under conditions effective to obtain a first hybridization product between said target(s) and said linker, b) contacting said first hybridization product with a combination under conditions effective to obtain a second hybridization product between said first hybridization product and said combination, wherein said combination comprises, before the addition of said first hybridization product, 1) a surface comprising multiple spatially discrete regions, at least two of which are substantially identical, each region comprising 2) at least 8 different oligonucleotide anchors, c) contacting said first hybridization product or said second hybridization product with a labeled detector probe, and d) detecting said detection probe.

Each of the assays or procedures described below can be performed in a high throughput manner, in which a large number of samples (e.g., as many as about 864, 1036, 1536, 2025 or more, depending on the number of regions in the combination) are assayed on each plate or surface rapidly and concurrently. Further, many plates or surfaces can be processed at one time. For example, in methods of drug discovery, a large number of samples, each comprising a drug candidate (e.g., a member of a combinatorial chemistry library, such as variants of small molecules, peptides, oligonucleotides, or other substances), can be added to separate regions of a combination as described or can be added to biological or biochemical samples that are then added to separate regions of a combination, and incubated with probe arrays located in the regions; and assays can be performed on each of the samples. With the recent advent and continuing development of high-density microplates, DNA spotting tools and of methods such as laser technology to generate and collect data from even denser microplates, robotics, improved dispensers, sophisticated detection systems and data-management software, the methods of this invention can be used to screen or analyze thousands or tens of thousands or more of compounds per day.

For example, in embodiments in which the probes are oligonucleotides, the assay can be a diagnostic nucleic acid or polynucleotide screen (e.g., a binding or other assay) of a large number of samples for the presence of genetic variations or defects (e.g., polymorphisms or specific mutations associated with diseases such as cystic fibrosis. See, e.g., Iitia et al (1992). *Molecular and Cellular Probes* 6, 505-512)); pathogenic organisms (such as bacteria, viruses, and protozoa, whose hosts are animals, including humans, or plants), or mRNA transcription patterns which are diagnostic of particular physiological states or diseases. Nucleic acid probe arrays comprising portions of ESTs (including full-length copies) can be used to evaluate transcription patterns produced by cells from which the ESTs were derived (or others). Nucleic acid probes can also detect peptides, proteins, or protein domains which bind specifically to particular nucleic acid sequences (and vice-versa).

Similarly, in embodiments in which the probes are antigen-binding molecules (e.g., antibodies), the assay can be a screen for variant proteins, or for protein expression patterns which are diagnostic for particular physiological states or disease conditions. See, e.g., FIGS. 40 and 41 for illustrations of the types of molecules which can be detected.

In another embodiment, the combinations of the invention can be used to monitor biochemical reactions such as, e.g., interactions of proteins, nucleic acids, small molecules, or the like—for example the efficiency or specificity of interactions between antigens and antibodies; or of receptors (such as purified receptors or receptors bound to cell membranes) and their ligands, agonists or antagonists; or of enzymes (such as proteases or kinases) and their substrates, or increases or decreases in the amount of substrate converted to a product; as well as many others. Such biochemical assays can be used to characterize properties of the probe or target, or as the basis of a screening assay. For example, to screen samples for the presence of particular proteases (e.g., proteases involved in blood clotting such as proteases Xa and VIIa), the samples can be assayed on combinations in which the probes are fluorogenic substrates specific for each protease of interest. If a target protease binds to and cleaves a substrate, the substrate will fluoresce, usually as a result, e.g., of cleavage and separation between two energy transfer pairs, and the signal can be detected. In another example, to screen samples for the presence of a particular kinase(s) (e.g., Src, tyrosine kinase, or ZAP70), samples containing one or more kinases of interest can be assayed on combinations in which the probes are peptides which can be selectively phosphorylated by one of the kinases of interest. Using art-recognized, routinely determinable conditions, samples can be incubated with the array of substrates, in an appropriate buffer and with the necessary cofactors, for an empirically determined period of time. (In some assays, e.g., for biochemical studies of factors that regulate the activity of kinases of interest, the concentration of each kinase can be adjusted so that each substrate is phosphorylated at a similar rate.) After treating (e.g., washing) each reaction under empirically determined conditions to remove kinases and undesired reaction components (optionally), the phosphorylated substrates can be detected by, for example, incubating them with detectable reagents such as, e.g., fluorescein-labeled anti-phosphotyrosine or anti-phosphoserine antibodies (e.g., at a concentration of about 10 nM, or more or less), and the signal can be detected. In another example, binding assays can be performed. For example, SH2 domains such as GRB2 SH2 or ZAP70 SH2 can be assayed on probe arrays of appropriate phosphorylated peptides; or blood sera can be screened on probe arrays of particular receptors for the presence of immune deficiencies. Also, enzyme-linked assays can be performed in such an array format. Combinations of the invention can also be used to detect mutant enzymes, which are either more or less active than their wild type counterparts, or to screen for a variety of agents including herbicides or pesticides.

Of course, MAPS assays can be used to quantitate (measure, quantify) the amount of active target in a sample, provided that probe is not fully occupied, that is, not more than about 90% of available probe sites are bound (or reacted or hybridized) with target. Under these conditions, target can be quantitated because having more target will result in having more probe bound. On the other hand, under conditions where more than about 90% of available probe sites are bound, having more target present would not substantially increase the amount of target bound to probe. Any of the heretofore-mentioned types of targets can be quantitated in this manner. For example, Example 6 describes the quantitation of oligonucleotide targets. Furthermore, it demonstrates that even if a target is present in large excess (e.g., if it is present in such large amounts that it saturates the amount of available probe in a MAPS probe array), by adding known amounts of unlabeled target to the binding mixture, one can "shift the sensitivity" of the reaction in order to allow even such large amounts of target to be quantitated.

In another embodiment, combinations of the invention can be used to screen for agents which modulate the interaction of a target and a given probe. An agent can modulate the target/probe interaction by interacting directly or indirectly with either the probe, the target, or a complex formed by the target plus the probe. The modulation can take a variety of forms, including, but not limited to, an increase or decrease in the binding affinity of the target for the probe, an increase or decrease in the rate at which the target and the probe bind, a competitive or non-competitive inhibition of the binding of the probe to the target, or an increase or decrease in the activity of the probe or the target which can, in some cases, lead to an increase or decrease in the probe/target interaction. Such agents can be man-made or naturally-occurring substances. Also, such agents can be employed in their unaltered state or as aggregates with other species; and they can be attached, covalently or noncovalently, to a binding member, either directly or via a specific binding substance. For example, to identify potential "blood thinners," or agents which interact with one of the cascade of proteases which cause blood clotting, cocktails of the proteases of interest can be tested with a plurality of candidate agents and then tested for activity as described above. Other examples of agents which can be employed by this invention are very diverse, and include pesticides and herbicides. Examples 16 and 17 describe high throughput assays for agents which selectively inhibit specific kinases, or for selective inhibitors of the interaction between SH2 domains and phosphorylated peptides.

In another embodiment, the combinations of the invention can be used to screen for agents which modulate a pattern of gene expression. Arrays of oligonucleotides can be used, for example, to identify mRNA species whose pattern of expression from a set of genes is correlated with a particular physiological state or developmental stage, or with a disease condition ("correlative" genes, RNAs, or expression patterns). By the terms "correlate" or "correlative," it is meant that the synthesis pattern of RNA is associated with the physiological condition of a cell, but not necessarily that the expression of a given RNA is responsible for or is causative of a particular physiological state. For example, a small subset of mRNAs can be identified which are expressed, upconverted and/or downconverted in cells which serve as a model for a particular disease state; this altered pattern of expression as compared to that in a normal cell, which does not exhibit a pathological phenotype, can serve as a indicator of the disease state ("indicator" genes, RNAs, or expression patterns). The terms "correlative" and "indicator" can be used interchangeably. For example, cells treated with a tumor promoter such as phorbol myristate might exhibit a pattern of gene expression which mimics that seen in the early stages of tumor growth. In another model for cancer, mouse insulinoma cells (e.g., cell line TGP61), when infected with adenovirus, exhibit an increase in the expression of, e.g., c-Jun and MIP-2, while the expression of housekeeping genes such as GAPDH and L32 remains substantially unaffected.

Agents which, after contacting a cell from a disease model, either directly or indirectly, and either in vivo or in vitro (e.g., in tissue culture), modulate the indicator expression pattern, might act as therapeutic agents or drugs for organisms (e.g., human or other animal patients, or plants) suffering from the disease. Agents can also modulate expression patterns by contacting the nucleic acid directly, e.g., in an in vitro (test tube) expression system. As used herein, "modulate" means to cause to increase or decrease the amount and/or activity of a molecule or the like which is involved in a measurable reaction. The combinations of the invention can be used to screen for such agents. For example, a series of cells (e.g., from a disease model) can be contacted with a series of agents (e.g., for a period of time ranging from about 10 minutes to about 48 hours or more) and, using routine, art-recognized methods (e.g., commercially available kits), total RNA or mRNA extracts can be made. If it is desired to amplify the amount of RNA, standard procedures such as RT-PCR amplification can be used (see, e.g., Innis et al eds., (1996) *PCR Protocols: A Guide to Methods in Amplification*, Academic Press, New York). The extracts (or amplified products from them) can be allowed to contact (e.g., incubate with) a plurality of substantially identical arrays which comprise probes for appropriate indicator RNAs, and those agents which are associated with a change in the indicator expression pattern can be identified. Example 15 describes a high throughput assay to screen for compounds which may alter the expression of genes that are correlative with a disease state.

Similarly, agents can be identified which modulate expression patterns associated with particular physiological states or developmental stages. Such agents can be man-made or naturally-occurring substances, including environmental factors such as substances involved in embryonic development or in regulating physiological reactions, or substances important in agribusiness such as pesticides or herbicides. Also, such agents can be employed in their unaltered state or as aggregates with other species; and they can be attached, covalently or noncovalently, to a binding member, either directly or via a specific binding substance.

Another embodiment of the invention is a kit useful for the detection of at least one target in a sample, which comprises:
  a) a surface, comprising multiple spatially discrete regions, at least two of which are substantially identical, each region comprising at least eight different anchors (oligonucleotide, or one of the other types described herein), and
  b) a container comprising at least one bifunctional linker molecule, which has a first portion specific for at least one of said anchor(s) and a second portion that comprises a probe which is specific for at least one of said target(s).

In one embodiment, there is provided a surface as in a) above and a set of instructions for attaching to at least one of said anchors a bifunctional linker molecule, which has a first portion specific for at least one of said anchor(s) and a second portion that comprises a probe which is specific for at least one target. The instructions can include, for example (but are not limited to), a description of each of the anchors on the surface, an indication of how many anchors there are and where on the surface they are located, and a protocol for specifically attaching (associating, binding, etc.) the linkers to the anchors. For example, if the anchors are oligonucleotides, the instructions can include the sequence of each anchor, from which a practitioner can design complementary anchor-specific moieties of linkers to interact specifically with (e.g., hybridize to) the anchors; if the anchors are peptides, the instructions can convey information about, e.g., antibodies which will interact specifically with the peptides. The instructions can also include a protocol for associating the anchors and linkers, e.g., conditions and reagents for hybridization (or other type of association) such as temperature and time of incubation, conditions and reagents for removing unassociated molecules (e.g., washes), and the like. Furthermore, the instructions can include information on the construction and use of any of the types of control linkers discussed herein, and of methods, e.g., to quantitate, normalize, "fine-tune" or calibrate assays to be performed with the combinations. The instructions can encompass any of the parameters, conditions or embodiments disclosed in this application, all of which can be performed routinely, with conventional procedures, by one of skill in the art.

As discussed elsewhere in this application, a practitioner can attach to a surface of the invention comprising a given array (or arrays) of anchors, a wide variety of types of linkers, thereby programming any of a wide variety of probe arrays. Moreover, a practitioner can remove a given set of linkers from a surface of the invention and add to it another set of linkers (either the same or different from the first set), allowing a given surface to be reused many times. This flexibility and reusability constitute further advantages of the invention.

In another embodiment, combinations of the invention can be used to map ESTs (Expressed Sequence Tags). That is, MAPS assays can be used to determine which, if any, of a group of ESTs were generated from different (or partially overlapping) portions of the same gene(s), and which, if any, are unique. FIGS. 18, 19, 20 and 21 illustrate such an assay, in this example an assay to determine which, if any, of 16 ESTs are "linked" to a common gene. A first step of the assay (see FIG. 18) is to assemble arrays in which each of the ESTs to be mapped is represented by at least one oligonucleotide probe that corresponds to it. A number of arrays equal to (or greater than) the number of ESTs to be mapped are distributed in separate regions (e.g., wells) of a surface; in the illustrated example, the surface of the combination comprises 16 wells, each of which contains an array of 16 different EST-specific oligonucleotides, numbered 1-16. An oligonucleotide which "corresponds to" an EST (is "EST-specific") is one that is sufficiently complementary to an EST such that, under selected stringent hybridization conditions, the oligonucleotide will hybridize specifically to that EST, but not to other, unrelated ESTs. An EST-corresponding oligonucleotide of this type can bind specifically (under optimal conditions) to the coding or non-coding strand of a cDNA synthesized from the gene from which the EST was originally generated or to an mRNA synthesized from the gene from which the EST was originally generated. Factors to be considered in designing oligonucleotides, and hybridization parameters to be optimized in order to achieve specific hybridization, are discussed elsewhere in this application. In order to assemble the arrays, linker molecules are prepared, each of which comprises a moiety specific for one of the anchors of a generic array plus a moiety comprising an oligonucleotide probe that corresponds to one of the ESTs to be mapped; and the linkers are attached to anchors as described elsewhere in this application. In a subsequent step, an aliquot of a sample comprising a mixture of nucleic acids (e.g., mRNA or single stranded or denatured cDNA), which may contain sequences that are complementary to one or more of the oligonucleotide probes, is added to each of the regions (wells) which comprises a probe array; the mixture is then incubated under routinely determined optimal conditions, thereby permitting nucleic acid to bind to complementary probes. If several of the EST-specific probes are complementary to different portions of a single nucleic acid, that nucleic acid will bind to each of the loci in the array at which one of those probes is located.

In a subsequent step, a different detector oligonucleotide (in the illustrated example, detectors #1 to 16) is added to each region (well) (see FIG. 19). A detector oligonucleotide is designed for each of the ESTs to be mapped. Each EST-specific detector corresponds to a different (at least partially non-overlapping) portion of the EST than does the probe oligonucleotide, so that the probe and the detector oligonucleotides do not interfere with one another. Consider, for example, the ESTs depicted in FIG. 21, which correspond to ESTs 1, 2 and 6 of FIGS. 18-20. FIG. 21 indicates that ESTs #1 and #2 were both obtained from gene X (they are "linked"), whereas EST #6 was obtained from a different unrelated gene. If aliquots of a sample containing a mixture of mRNAs, including one generated from gene X, are incubated with the probe arrays shown in FIGS. 18-20, the gene X mRNA will, under optimal conditions, hybridize at the loci with probes 1 and 2, but not at those with probe 6. (Of course, each mRNA must be added in molar excess over the sum of the probes to which it can hybridize.) If detector oligonucleotide 1 is added to region (well) 1, it will hybridize to the gene X mRNA which is bound at loci 1 and 2 of the probe array, but not at locus 6. Similarly, if detector oligonucleotide 2 is added to another well—say, well #2—it will also bind at loci 1 and 2, but not 6. In this fashion, one can determine in a high throughput manner which of the ESTs are linked, i.e. code for portions of the same gene, and which ESTs are unique. For the hypothetical example shown in FIG. 20, the first 3 ESTs encode portions of the same gene, the last 5 ESTs encode portions of another gene, and the remaining ESTs appear not to be linked. Conditions of hybridization, optional wash steps, methods of detection, and the like are discussed elsewhere in this application with regard to other MAPS assays. In order to confirm the linkage data obtained by the MAPS assay, one could perform PCR reactions using pairs of EST-specific oligonucleotide probes as sense and anti-sense primers. Every pair of linked ESTs should yield a PCR product. Note that this pairwise PCR test could be performed to determine linkage directly without using the Linkage MAPS assay; however, many reactions would be required, and each EST primer would have to be synthesized as both sense and anti-sense strands. For the illustrated example, 180 such reactions would be required.

In one aspect, the invention relates to a method of determining which of a plurality of ESTs are complementary to a given nucleic acid, comprising, a) incubating an immobilized array of oligonucleotide probes, at least one of which corresponds to each of said ESTs, with a test sample which may contain said given nucleic acid, to obtain a hybridization product between said oligonucleotide probes and said nucleic acid, b) incubating said hybridization product with a detector oligonucleotide, which corresponds to an EST to which one of said oligonucleotide probes corresponds, but which is specific for a different portion of the EST than is said oligonucleotide probe, and c) detecting which oligonucleotide probes of said array are labeled by said detector oligonucleotide;

wherein said array of oligonucleotide probes is immobilized on a region of a combination, wherein said combination comprises 1) a surface comprising a number of spatially discrete, substantially identical, regions equal to the number of ESTs to be studied, each region comprising 2) a number of different anchors equal to the number of ESTs to be studied, each anchor in association with 3) a bifunctional linker which has a first portion that is specific for the anchor, and a second portion that comprises an oligonucleotide probe which corresponds to at least one of said ESTs.

In another aspect, the invention relates to a method as above, wherein of said ESTs may be complementary to said nucleic acid, and wherein each of said ESTs comprises two different oligonucleotide sequences, the first of which defines an oligonucleotide probe corresponding to said EST, and the second of which defines a detector oligonucleotide corresponding to said EST, comprising, a) contacting a sample which comprises molecules of said nucleic acid with at least one region of a combination, wherein said region comprises an array of oligonucleotide probes, at least one of which corresponds to each of said ESTs, b) incubating said sample with said region, thereby permitting molecules of said nucleic acid to bind to said EST-corresponding oligonucleotide probes which are complementary to portions of said nucleic acid, c) incubating said region comprising molecules of said nucleic acid bound to one or more of said EST-corresponding oligonucleotide probes with a detector oligonucleotide which corresponds to an EST to which a given one of the oligonucleotide probes of said array corresponds, thereby binding detector oligonucleotides to nucleic acid molecules which have bound to said given oligonucleotide probe or to other oligonucleotide probes which are complementary to said nucleic acid, d) detecting the presence of said detector oligonucleotides, thereby identifying which EST-corresponding oligonucleotide probes of said array are complementary to portions of a nucleic acid which binds to said given oligonucleotide EST-corresponding probe, thereby identifying which ESTs are complementary to said given nucleic acid wherein said array of oligonucleotide probes is immobilized on a region of a combination, wherein said combination comprises 1) a surface comprising a number of spatially discrete, substantially identical regions equal to the number of ESTs to be studied, each region comprising 2) a number of different anchors equal to the number of ESTs to be studied, each anchor in association with 3) a bifunctional linker which has a first portion that is specific for the anchor, and a second portion that comprises an oligonucleotide probe which corresponds to at least one of said ESTs.

The components of an EST mapping assay can be assembled in any order. For example, the anchors, linkers and ESTs can be assembled sequentially; or linkers and ESTs, in the presence or absence of reporters, can be assembled in solution and then added to the anchors.

In another aspect, the invention relates to a method of determining which of a plurality of ESTs are complementary to a given nucleic acid, comprising, a) incubating a collection of bifunctional oligonucleotide linker molecules, each of which comprises a first portion which is a probe that corresponds to at least one of said ESTs, and a second portion which is specific for an anchor oligonucleotide, with a test sample which may contain said given nucleic acid, to obtain a first hybridization product between said oligonucleotide probes and said nucleic acid, b) incubating said first hybridization product with an immobilized array of anchor oligonucleotides, wherein each anchor oligonucleotide corresponds to the anchor-specific portion of at least one of said linker molecules, to form a second hybridization product comprising said anchors, said oligonucleotide probes and said nucleic acid, and c) incubating either said first or said second hybridization product with a detector oligonucleotide; which corresponds to an EST to which one of said oligonucleotide probes corresponds, but which is specific for a different portion of the EST than is said oligonucleotide probe, and d) detecting which oligonucleotide probes of said array are labeled by said detector oligonucleotide, wherein said array of anchor oligonucleotides is immobilized on a region of a combination, wherein said combination comprises 1) a surface comprising a number of spatially discrete, substantially identical, regions equal to the number of ESTs to be studied, each region comprising 2) a number of different anchors equal to the number of ESTs to be studied.

Of course, the above methods for mapping ESTs can be used to map test sequences (e.g., polynucleotides) onto any nucleic acid of interest. For example, one can determine if two or more cloned DNA fragments or cDNAs map to the same genomic DNA. Such a procedure could aid, for example, in the structural elucidation of long, complex genes. In a similar manner, one can determine if one or more spliced out sequences or coding sequences map to the same genomic DNA. Such a determination could be used, for example, in a diagnostic test to distinguish between a normal and a disease condition which are characterized by differential splicing patterns. Many other applications of the mapping method will be evident to one of skill in the art.

In another aspect, the invention relates to a method of determining which of a plurality of polynucleotides are complementary to a given nucleic acid, wherein one or more of said polynucleotides may be complementary to said nucleic acid, and wherein each of said polynucleotides comprises two different oligonucleotide sequences, the first of which defines an oligonucleotide probe corresponding to said polynucleotide, and the second of which defines a detector oligonucleotide corresponding to said polynucleotide, comprising, a) contacting a sample which comprises molecules of said nucleic acid with at least one region of a combination, wherein said region comprises an array of oligonucleotide probes, at least one of which corresponds to each of said polynucleotides, b) incubating said sample with said region, thereby permitting molecules of said nucleic acid to bind to said polynucleotide-corresponding oligonucleotide probes which are complementary to portions of said nucleic acid, c) incubating said region comprising molecules of said nucleic acid bound to one or more of said polynucleotide-corresponding oligonucleotide probes with a detector oligonucleotide which corresponds to a polynucleotide to which a given one of the oligonucleotide probes of said array corresponds, thereby binding detector oligonucleotides to nucleic acid molecules which have bound to said given oligonucleotide probe or to other oligonucleotide probes which are complementary to said nucleic acid, d) detecting the presence of said detector oligonucleotides, thereby identifying which polynucleotide-corresponding oligonucleotide probes of said array are complementary to portions of a nucleic acid which binds to said given oligonucleotide polynucleotide-corresponding probe, thereby identifying which polynucleotides are complementary to said given nucleic acid, wherein said array of oligonucleotide probes is immobilized on a region of a combination, wherein said combination comprises 1) a surface comprising a number of spatially discrete, substantially identical, regions equal to the number of polynucleotides to be studied, each region comprising 2) a number of different anchors equal to the number of polynucleotides to be studied, each anchor in association with 3) a bifunctional linker which has a first portion that is specific for the anchor, and a second portion that comprises an oligonucleotide probe which corresponds to at least one of said polynucleotides.

In another aspect of the invention, the above methods to map ESTs or other polynucleotides further comprise removing unbound portions of the sample between one or more of the steps.

In another embodiment of the invention, one or more RNA targets of interest (e.g., mRNA, or other types of RNA) are converted into cDNAs by reverse transcriptase, and these cDNAs are then hybridized to a probe array. This type of assay is illustrated schematically in FIG. 8. RNA extracts (or purified mRNA) are prepared from cells or tissues as described herein. Reverse transcriptase and oligonucleotide primers which are specific for the RNAs of interest are then added to the RNA sample, and, using art-recognized conditions and procedures, which can be routinely determined and optimized, the first strands of cDNAs are generated. The term "specific" primer refers to one that is sufficiently complementary to an mRNA of interest to bind to it under selected stringent hybridization conditions and be recognized by reverse transcriptase, but which does not bind to undesired nucleic acid (see above for a discussion of appropriate reaction conditions to achieve specific hybridization). Residual RNA—mRNAs which were not recognized by the specific primers, and/or other types of contaminating RNAs in an RNA extract, such as tRNA or rRNA—can be removed by any of a variety of ribonucleases or by chemical procedures, such as treatment with alkali, leaving behind the single strand cDNA, which is subsequently placed in contact with a MAPS probe array. The use of reverse transcriptase in this method minimizes the need for extensive handling of RNA, which can be sensitive to degradation by nucleases and thus difficult to work with. Furthermore, the additional specificity engendered by the specific reverse transcriptase primers imparts an added layer of specificity to the assay.

Optionally, the cDNAs described above can be amplified before hybridization to the probe array to increase the signal strength. The oligonucleotide reverse transcriptase primers described above can comprise, at their 5' ends, sequences (which can be about 22-27 nucleotides long) that specify initiation sites for an RNA polymerase (e.g., T7, T3 or SP2 polymerase, or the like). In the example shown in FIG. 8, a T7 promoter sequence has been added to the reverse transcriptase primer. The polymerase recognition site becomes incorporated into the cDNA and can then serve as a recognition site for multiple rounds of transcription by the appropriate RNA polymerase (in vitro transcription, or IVT). Optionally, the mRNAs so generated can be amplified further, using PCR and appropriate primers, or the cDNA, itself, can be so amplified. Procedures for transcription and PCR are routine and well-known in the art.

The flexibility of PCR allows for many variations in the methods of the invention. In one embodiment, one or both of the PCR primers which are used to amplify a target can comprise a chemical modification which allows the resulting PCR product to attach, specifically or non-specifically, to a solid support. Such chemical modifications include, for example, 5' amidation which allows binding to surfaces such as Costar's DNA Bind Plates, (e.g., which are modified with N-oxysuccinimide ester, or maleic anhydride coated plates such as Reacti-Bind plates from Pierce, Rockford, Ill.). Methods for generating oligonucleotides comprising such chemical modifications are routine and conventional in the art. A PCR product comprising such a modified primer can be attached to any desired support, including a solid support, e.g., the inner walls of a microtiter well, a bead (e.g., a non-magnetic or magnetic bead), or any of the types of surfaces described herein. Of course, a PCR primer can also be attached to a support before a PCR reaction is initiated. Several cycles of PCR can be repeated without washing but with an excess of bound primer, so that the resulting PCR product remains attached to the support. The attachment of an amplified target sequence to a support can facilitate the washing (or purification) of the target, either before it is contacted with (e.g., hybridized to) a surface comprising anchors and/or linkers, or after it has been contacted with and then released from such a surface.

In another embodiment, one or both of the PCR primers used to amplify a target can comprise one or more restriction enzyme sites, allowing the introduction of restriction sites adjacent to either end of, or flanking, a target sequence of interest. Restriction sites can be added to an amplified target by PCR either before or after it has contacted (e.g., hybridized to) a surface comprising anchors and/or linkers. Restriction site(s) introduced in this manner can, for example, facilitate the cloning of an amplified target by providing cloning sites which flank the target sequence. Restriction sites can also facilitate the purification of an amplified sequence. For example, one or more restriction sites can be placed in a PCR primer between a target specific sequence and a chemical modification which allows attachment to a support. After a target has been PCR amplified, using the modified PCR primer, and has been bound to a support via the chemical modification, it can be washed and then cleaved at the restriction site(s) adjacent to the target sequence, thereby releasing the washed target. See, e.g., FIG. 23.

Of course, cleavable sites other than restriction enzyme sites can also be used in the methods described above, e.g., a peptide which can be cleaved by a specific protease, or another component which can be cleaved and/or released by physical, chemical or other means.

In another embodiment, one or both of the PCR primers used to amplify a target can comprise a sequence (which is not necessarily present in the target) that is specific for, e.g., a target-specific reporter or a detection linker.

Of course, the above-described primer modifications can be used together in any desired combination, and can be added to an amplified product at any stage of an assay. Examples 21 and 22 demonstrate protocols in which several of the primer modifications described above are incorporated into an amplified target.

The above-described methods, in which mRNA targets are converted to cDNA with reverse transcriptase and/or are amplified by PCR before assaying on MAPS plates, can be used instead of the standard MAPS assay procedure for any of the RNA-based assays described above.

Nucleic acids used in the methods of the invention, e.g., targets, oligonucleotides involved in the detection of a target, or nuclease protection fragments (described elsewhere herein) can be amplified by any of a variety of conventional enzymatic procedures, including PCR and ligase reactions. One such amplification method is Transcription-Mediated Amplification (see, e.g., Abe et al. (1993). *J. Clin. Microbiol.* 31, 3270-3274). See also Example 32 and FIGS. 36-39 and 42.

In another embodiment of the invention, one or more nucleic acid targets of interest are hybridized to specific polynucleotide protection fragments and subjected to a nuclease protection procedure, and those protection fragments which have hybridized to the target(s) of interest are assayed on MAPS plates. Of course, such "MAPS plates" can contain anchors which are not associated with linkers (e.g., which can be associated directly with a target or nuclease protection fragment of interest); the advantages of nuclease protection as used in conjunction with any type of probe array will be evident to one of skill in the art from this specification and any of its ancestors to which benefit is claimed. If the target of interest is an RNA and the protection fragment is DNA, a Nuclease Protection/MAPS Assay (NPA-MAPS) can reduce the need for extensive handling of RNA, which can be sensitive to degradation by contaminating nucleases and thus difficult to work with. Treatment of a sample with a nuclease protection procedure also allows for a sample with reduced viscosity. Nuclease protection of a sample can allow for greater sensitivity and reproducibility in an assay. See, e.g., Example 30, which illustrates the sensitivity and reproducibility of a typical-assay in which a sample is treated with a nuclease protection procedure. An advantage of the invention is that assays can be sensitive enough that amplification of the target (e.g., by PCR) is not necessary in order to detect a signal. In an NPA-MAPS assay, the probes in the probe array are oligonucleotides of the same strandedness as the nucleic acid targets of interest, rather than being complementary to them, as in a standard MAPS assay. One example of an NPA-MAPS assay is schematically represented in FIG. 9.

In an NPA-MAPS assay, the target of interest can be any nucleic acid, e.g., genomic DNA, cDNA, viral DNA or RNA, rRNA, tRNA, mRNA, oligonucleotides, nucleic acid fragments, modified nucleic acids, synthetic nucleic acids, or the like. In a preferred embodiment of the invention, the procedure is used to assay for one or more mRNA targets which are present in a tissue or cellular RNA extract. A sample which contains the target(s) of interest is first hybridized under selected stringent conditions (see above for a discussion of appropriate reaction conditions to achieve specific hybridization) to an excess of one or more specific protection fragment(s). A protection fragment is a polynucleotide, which can be, e.g., RNA, DNA (including a PCR product), PNA or modified or substituted nucleic acid, that is specific for a portion of a nucleic acid target of interest. By "specific" protection fragment, it is meant a polynucleotide which is sufficiently complementary to its intended binding partner to bind to it under selected stringent conditions, but which will not bind to other, unintended nucleic acids. A protection fragment can be at least 10 nucleotides in length, preferably 50 to about 100, or about as long as a full length cDNA. In a preferred embodiment, the protection fragments are single stranded DNA oligonucleotides. Protection fragments specific for as many as 100 targets or more can be included in a single hybridization reaction. After hybridization, the sample is treated with a cocktail of one or more nucleases so as to destroy nucleic acid other than the protection fragment(s) which have hybridized to the nucleic acid(s) of interest and (optionally) the portion(s) of nucleic acid target which have hybridized and been protected from nuclease digestion during the nuclease protection procedure (are in a duplexed hybrid). For example, if the sample comprises a cellular extract, unwanted nucleic acids, such as genomic DNA, tRNA, rRNA and mRNA's other than those of interest, can be substantially destroyed in this step. Any of a variety of nucleases can be used, including, e.g., pancreatic RNAse, mung bean nuclease, S1 nuclease, RNAse A, Ribonuclease T1, Exonuclease III, Exonuclease VII, RNAse CLB, RNAse PhyM, RNAse U2, or the like, depending on the nature of the hybridized complexes and of the undesirable nucleic acids present in the sample. RNAse H can be particularly useful for digesting residual RNA bound to a DNA protection fragment. Reaction conditions for these enzymes are well-known in the art and can be optimized empirically. Also, chemical procedures can be used, e.g., alkali hydrolysis of RNA. As required, the samples can be treated further by well-known procedures in the art to remove unhybridized material and/or to inactivate or remove residual enzymes (e.g., phenol extraction, precipitation, column filtration, etc.). The process of hybridization, followed by nuclease digestion and (optionally) chemical degradation, is called a nuclease protection procedure; a variety of nuclease protection procedures have been described (see, e.g., Lee et al (1987). *Meth. Enzymol.* 152, 633-648. Zinn et al (1983). *Cell* 34, 865-879.). Samples treated by nuclease protection, followed by an (optional) procedure to inactivate nucleases, are placed in contact with a MAPS probe array and the usual steps of a MAPS assay are carried out. Bound protection fragments can be detected by, e.g., hybridization to labeled target-specific reporters, as described herein for standard MAPS assays, or the protection fragments, themselves, can be labeled, covalently or non-covalently, with a detectable molecule.

If desired, one or more controls can be included for normalizing an NPA-MAPS assay. For example, one or more protection fragments corresponding to a nucleic acid which is expected to be present in each of a series of samples in a substantially constant amount (e.g., a constitutively produced mRNA, a portion of a genomic DNA, a tRNA or rRNA) can be used. The ability to detect and quantify an internal normalization control, e.g., genomic DNA, in an assay for measuring nucleic acids which are present in variable amounts (e.g., mRNAs), is an advantage of using protection fragments in the assays.

Because the amount of the normalization standard(s) may be lower than that of expressed mRNAs of interest, the assay may be adjusted so the signals corresponding to the expressed genes do not swamp out the signal(s) corresponding to the normalization standard(s). Methods of adjusting the signal levels are conventional and will be evident to one of skill in the art. For example, any of the methods described herein for balancing signal intensities (e.g., signal attenuation, fine-tuning) can be used (e.g., using blocked linkers; labeling the signal moiety designed to detect the normalization standard at a greater level than that designed to detect the mRNA; placing at a locus designated for detecting a normalization standard a plurality of linkers which are specific for different portions of the normalization nucleic acid, or for protection fragments that correspond to different portions of that nucleic acid, etc.). The normalization standard(s) and the nucleic acid targets (e.g., mRNAs) of interest can be detected simultaneously or sequentially, e.g., by any of the methods described elsewhere herein. Example 28 and FIG. 29 illustrate a typical experiment in which internal DNA normalization standards are used in an assay of mRNAs.

In a preferred embodiment, the protection fragment is directly labeled, e.g., rather than being labeled by hybridization to a target-specific reporter. For example, the reporter is bound to the protection fragment through a ligand-antiligand interaction, e.g., a streptavidin enzyme complex is added to a biotinylated protection oligonucleotide. In another example, the protection fragment is modified chemically, (e.g., by direct coupling of horseradish peroxidase (HRP) or of a fluorescent dye) and this chemical modification is detected, either with the nucleic acid portion of the protection fragment or without it, (e.g., after cleavage of the modification by, for example, an enzymatic or chemical treatment). In any of the above methods, a protection fragment can be labeled before or after it has hybridized to a corresponding linker molecule.

In order to control that the nuclease protection procedure has worked properly, i.e. that non-hybridized nucleic acids have been digested as desired, one can design one or more protection fragments to contain overhanging (non-hybridizing) segments that should be cleaved by the nucleases if the procedure works properly. The presence or absence of the overhanging fragments can be determined by hybridization with a complementary, labeled, detection probe, or the overhanging portion of the protection fragment, itself, can be labeled, covalently or non-covalently, with a detectable molecule. This control can be performed before the sample is placed in contact with the probe array, or as a part of the MAPS assay, itself. An example of such a control assay is described in Example 15. Of course, because different labels can be easily distinguished (e.g., fluors with different absorption spectra), several differently labeled oligonucleotides can be included in a single assay. Further, the standard nuclease protection assay as analyzed by gel electrophoresis can be used during assay development to verify that the protection fragments are processed as expected.

Other controls for correct nuclease digestion will be evident to one of skill in the art. For example, one can include in an assay a nuclease protection fragment which is known not to have specificity for any nucleic acid in the sample (e.g., in an assay for plant nucleic acids, one can include a protection fragment specific for an animal gene which is known to be absent in plants).

After detection of targets, the detection probe (e.g., HRP-labeled) signal can be eliminated (e.g. denatured, killed, quenched, suppressed, blocked), plates washed to remove any resulting reagents, agents, or buffers which might interfere in the next step (e.g., denaturing regent), and then the overhang can be detected with a different detection probe (e.g., also HRP-labeled). The use of signal denaturation followed by addition of a different detection probe with the same signaling moiety can be used at various stages of the assay.

Utilization of two different flourescent probes and dual color detection can be used without denaturation or signal blocking.

In one embodiment of the invention, as was noted above, an oligonucleotide probe is used to screen for a nucleic acid which comprises one or more polymorphisms. In a preferred embodiment, the nucleic acid (e.g., a DNA, such as a genomic DNA, or an RNA, such as an mRNA) comprises one or more SNPs. Routine, art-recognized procedures can be used to carry out the procedure. For example, to screen for a DNA comprising a known SNP, or an mRNA expressed from such a DNA, a "SNP-specific" protection fragment is hybridized to a sample comprising nucleic acids which may comprise that SNP. By "SNP-specific" protection fragment is meant in this context a protection fragment which comprises the altered base of the SNP or, if an mRNA is to be analyzed, the reverse complement of such a sequence. The sample is then treated with one or more appropriate nucleases which, under appropriate, empirically determinable conditions, digest unhybridized single stranded nucleic acid and cleave double stranded (duplex) nucleic acid (e.g., DNA-DNA hybrids, DNA-RNA hybrids, or the like) at the site of a mismatch (e.g., a single base mismatch). Appropriate nucleases include, e.g., S1 or RHAse H. If a nucleic acid which comprises a SNP is present in the sample and hybridizes to the SNP-specific protection fragment, the protection fragment will survive the digestion procedure intact, and can be subjected to a MAPS assay and detected by a detection probe or detection oligonucleotide which is specific for a sequence of the protection fragment. Nucleic acids which do not comprise the SNP will be cleaved at the site of the mismatch between the SNP-specific protection fragment and the corresponding wild type sequence in the nucleic acid. If desired, a portion of the protection fragment which lies either distal to or proximal to the site of cleavage can be removed, using conventional methods (e.g., heat denaturation, enzymatic cleavage, etc.) An assay can be designed either so that the cleaved molecules (or portions thereof) will not bind to linkers, or so that such cleaved molecules, even if a portion thereof binds to a linker, will not be detected by an appropriately designed detection probe or detection oligonucleotide. Example 29 and FIGS. 30 and 31 illustrate, i.a., that assays of the invention can detect a single base mismatch in an expressed SNP. Example 32 (FIG. 41) illustrates an assay for the detection of SNPs, which is applicable, e.g., to the detection of SNPs in genomic DNA.

NPA-MAPS assays can be used to quantitate the amount of a target in a sample. If protection fragment is added at a large enough molar excess over the target to drive the hybridization reaction to completion, the amount of protection fragment remaining after the nuclease protection step will reflect how much target was present in the sample. One example of such a quantitation reaction is described in Examples 12 and 13.

In one embodiment of the invention, different types of targets in a sample, e.g., various combinations of DNA, RNA, intracellular proteins and secreted proteins, can be assayed with a single probe array. See FIGS. 40 and 41 for examples of such assays.

NPA-MAPS assays can be used to implement any of the methods described above that use standard MAPS assays.

In a preferred embodiment, the polynucleotide protection fragments are measured by the mass spectrometer rather than on MAPS plates. In a most preferred embodiment, none of the polynucleotides are bound (attached) to a solid surface during the hybridization or nuclease digestion steps. After hybridization, the hybridized target can be degraded, e.g., by nucleases or by chemical treatments, leaving the protection fragment in direct proportion to how much fragment had been hybridized to target. Alternatively, the sample can be treated so as to leave the (single strand) hybridized portion of the target, or the duplex formed by the hybridized target and the protection fragment, to be further analyzed. The samples to be analyzed are separated from the rest of the hybridization and nuclease mixture (for example by ethanol precipitation or by adsorption or affinity chromatography, etc.), eluted or solubilized, and injected into the mass spectrometer by loop injection for high throughput. In a preferred embodiment, the samples to be analyzed (e.g., protection fragments) are adsorbed to a surface and analyzed by laser desorption, using well-known methods in the art. For highest sensitivity Fourier Transform Mass Spectrometry (FTMS) (or other similar advanced technique) may be used, so that femtomoles or less of each protection fragment can be detected.

The protection fragments that are to be detected within one (or more) samples can be designed to give a unique signal for the mass spectrometer used. In one embodiment, the protection fragments each have a unique molecular weight after hybridization and nuclease treatment, and their molecular weights and characteristic ionization and fragmentation pattern will be sufficient to measure their concentration. To gain more sensitivity or to help in the analysis of complex mixtures, the protection fragments can be modified (e.g., derivatized) with chemical moieties deigned to give clear unique signals. For example each protection fragment can be derivatized with a different natural or unnatural amino acid attached through an amide bond to the oligonucleotide strand at one or more positions along the hybridizing portion of the strand. With a mass spectrometer of appropriate energy, fragmentation occurs at the amide bonds, releasing a characteristic proportion of the amino acids. This kind of approach in which chemical moieties of moderate size (roughly 80 to 200 molecular weight) are used as mass spectrometric tags is desirable, because molecules of this size are generally easier to detect. In another example, the chemical modification is an organic molecule with a defined mass spectrometric signal, such as a tetraalkylammonium group which can, for example, derivatize another molecule such as, e.g., an amino acid. In another example, positive or negative ion signals are enhanced by reaction with any of a number of agents. For example, to enhance positive ion detection, one can react a pyrylium salt (such as, e.g., 2-4-dithenyl, 6-ethyl pyrylium tetrafluoroborate, or many others) with an amine to form a pyridinium salt; any of a number of other enhancing agents can be used to form other positively charged functional groups (see, e.g., Quirke et al (1994). *Analytical Chemistry* 66, 1302-1315). Similarly, one can react any of a number of art-recognized agents to form negative ion enhancing species. The chemical modification can be detected, of course, either after having been cleaved from the nucleic acid, or while in association with the nucleic acid. By allowing each protection fragment to be identified in a distinguishable manner, it is possible to assay (e.g., to screen) for a large number of different targets (e.g., for 2, 6, 10, 16 or more different targets) in a single assay. Many such assays can be performed rapidly and easily. Such an assay or set of assays can be conducted, therefore, with high throughput as defined herein.

Regardless of whether oligonucleotides are detected directly by their mass or if unique molecular tags are used, the signals for each molecule to be detected can be fully characterized in pure preparations of known concentration. This will allow for the signal to be quantified (measured, quantitated) accurately. For any molecule to be detected by mass spectrometry, the intensity and profile cannot be predicted with accuracy. The tendency of the molecule to be ionized, the sensitivity of all chemical bonds within the molecule to fragmentation, the degree to which each fragment is multiply charged or singly charged, are all too complex to be predicted. However, for a given instrument with fixed energy and sample handling characteristics the intensity and profile of the signal is very reproducible. Hence for each probe the signal can be characterized with pure standards, and the experimental signals interpreted quantitatively with accuracy.

In one aspect, the invention relates to a method to detect one or more nucleic acids of interest, comprising subjecting a sample comprising the nucleic acid(s) of interest to nuclease protection with one or more protection fragments, and detecting the hybridized duplex molecules, or the protected nucleic acid, or the protection fragment, with mass spectrometry.

Methods of analyzing nucleic acids by mass spectrometry are well-known in the art. See, e.g., Alper et al (1998). *Science* 279, 2044-2045 and Koster, U.S. Pat. No. 5,605,798.

In addition to the variety of high throughput assays described above, many others will be evident to one of skill in the art.

An advantage of using multiprobe assays is the ability to include a number of "control" probes in each probe array which are subject to the same reaction conditions as the actual experimental probes. For example, each region in the array can comprise positive and/or negative controls. The term, a "positive control probe," is used herein to mean a control probe that is known, e.g., to interact substantially with the target, or to interact with it in a quantitatively or qualitatively known manner, thereby acting as a(n internal) standard for the probe/target interaction. Such a probe can control for hybridization efficiency, for example. The term, a "negative control probe," is used herein to mean a control probe which is known not to interact substantially with the target. Such a probe can control for hybridization specificity, for example. As examples of the types of controls which can be employed, consider an assay in which an array of oligonucleotide probes is used to screen for agents which modulate the expression of a set of correlative genes for a disease. As an internal normalization control for variables such as the number of cells lysed for each sample, the recovery of mRNA, or the hybridization efficiency, a probe array can comprise probes which are specific for one or more basal level or constitutive house-keeping genes, such as structural genes (e.g., actin, tubulin, or others) or DNA binding proteins (e.g., transcription regulation factors, or others), whose expression is not expected to be modulated by the agents being tested. Furthermore, to determine whether the agents being tested result in undesired side effects, such as cell death or toxicity, a probe array can comprise probes which are specific for genes that are known to be induced as part of the apoptosis (programmed cell death) process, or which are induced under conditions of cell trauma (e.g., heat shock proteins) or cell toxicity (e.g., p450 genes).

Other control probes can be included in an array to "fine tune" the sensitivity of an assay. For example, consider an assay for an agent which modulates the production of mRNAs associated with a particular disease state. If previous analyses have indicated that one of the correlative mRNAs (say, mRNA-A) in this set is produced in such high amounts compared to the others that its signal swamps out the other mRNAs, the linkers can be adjusted to "fine tune" the assay so as to equalize the strengths of the signals. "Blocked linkers," which comprise the anchor-specific oligonucleotide sequence designated for the mRNA-A target, but which lack the probe-specific sequence, can be added to dilute the pool of target-specific linkers and thus to reduce the sensitivity of the assay to that mRNA. The appropriate ratios of blocked and unblocked linkers can be determined with routine, conventional methods by one of skill in the art.

The "fine tuning" of an assay for a particular target by diluting an active element with an inactive element can also be done at other steps in the assay. For example, it can be done at the level of detection by diluting a labeled, target-specific reporter with an "inactive" target-specific reporter, e.g., one with the same target-specific moiety (e.g., an oligonucleotide sequence) but without a signaling entity, or with an inactivated or inactive form of the signaling entity. The term "signaling entity," as used herein, refers to a label, tag, molecule, or any substance which emits a detectable signal or is capable of generating such a signal, e.g., a fluorescent molecule, luminescence enzyme, or any of the variety of signaling entities which are disclosed herein). In an especially preferred embodiment, the "fine tuning" can be done at the step of contacting a target-containing complex with a detection linker (detection linkers are described below, e.g., in the section concerning complex sandwich-type detection methods, Example 23, and FIG. 24). A set of detection linkers can be designed, e.g., to fine tune the sensitivity for each individual target in an assay. For example, if a particular target is known to be present in a sample at very high levels, the detection linker for that target can be diluted with an empirically-determinable amount of "blocked detection linker," comprising the target-specific moiety (e.g., oligonucleotide sequence) but no moiety specific for a reporter reagent, or comprising the target-specific moiety and a reporter reagent-specific moiety which is pre-bound to an inactive reporter reagent. That is, instead of comprising a moiety specific for a reporter reagent, that moiety can be absent, or prevented (e.g., blocked) from interacting with (e.g., hybridizing to) the reporter reagent. Such fine tuning is sometimes referred to herein as signal "attenuation." FIG. 28 illustrates an experiment in which such signal attenuation was performed.

Samples to be tested in an assay of the invention can comprise any of the targets described above, or others. Liquid samples to be assayed can be of any volume appropriate to the size of the test region, ranging from about 100 nanoliters to about 100 microliters. In a preferred embodiment, liquid drops of about 1 microliter are applied to each well of a 1536 well microtiter dish. Samples can be placed in contact with the probe arrays by any of a variety of methods suitable for high throughput analysis, e.g., by pipetting, inkjet based dispensing or by use of a replicating pin tool. Samples are incubated under conditions (e.g., salt concentration, pH, temperature, time of incubation, etc.—see above) effective for achieving binding or other stable interaction of the probe and the target. These conditions are routinely determinable. After incubation, the samples can optionally be treated (e.g. washed) to remove unbound target, using conditions which are determined empirically to leave specific interactions intact, but to remove non-specifically bound material. For example, samples can be washed between about one and ten times or more under the same or somewhat more stringent conditions than those used to achieve the probe/target binding.

Samples containing target RNA, e.g., mRNA, rRNA, tRNA, viral RNA or total RNA, can be prepared by any of a variety of procedures. For example, in vitro cell cultures from which mRNA is to be extracted can be plated on the regions of a surface, such as in individual wells of a microtiter plate. Optionally, these cells, after attaining a desired cell density, can be treated with an agent of interest, such as a stimulating agent or a potential therapeutic agent, which can be added to the cells by any of a variety of means, e.g., with a replicating pin tool (such as the 96 or 384 pin tools available from Beckman), by pipetting or by ink-jet dispensing, and incubated with the cells for any appropriate time period, e.g., between about 15 minutes and about 48 hours, depending upon the assay. Total RNA, mRNA, etc. extracts from tissues or cells from an in vitro or in vivo source can be prepared using routine, art-recognized methods (e.g., commercially available kits).

In one embodiment, cells are lysed (or permeabilized), in the presence or absence of nuclease protection fragment(s), and the crude lysate is used directly (e.g., in the well of a microtiter plate), without further purification from, e.g., other cellular components. If the cells are lysed in the absence of nuclease protection fragments, such protection fragments can optionally be added subsequently to the lysate.

In a preferred embodiment, e.g., in which nuclease protection fragments are detected, samples are prepared by contacting cells of interest (e.g., cells on the surface of a well of a microtiter plate; cells in a tissue or whole organism sample; or the like) with an aqueous medium (lysis solution) which comprises a surfactant or detergent (e.g., SDS, e.g., at about 0.01% to about 0.5% w/v) and an agent (e.g., formamide (e.g., at about 8-about 60%, v/v), guanidium HCl (e.g., at about 0.1-about 6M), guanidium isothyocyanate (e.g., at about 0.05-about 8 M) or urea (e.g., at about 40-about 46%, w/v, or about 7M)), which, alone or in combination with one or more other agents, can act as a chaotropic agent. The aqueous medium can be buffered by any standard buffer. In a preferred embodiment, the buffer is about 0.5-6×SSC, more preferably about 3× SSC. Optionally, the aqueous medium can also comprise tRNA at an appropriate concentration, e.g., about 0.1-2.0 mg/ml, preferably about 0.5 mg/ml. Nuclease protection fragments may also be added to the aqueous medium before it is added to the cells. The optimal concentration of each protection fragment can be determined empirically, using conventional methods. In a preferred embodiment, the concentration of each protection fragment is about 3 to about 300 pM, more preferably about 30 pM.

Cells are incubated in the aqueous solution until the cells become permeabilized and/or lysed, and DNA and/or mRNA is released from the cells into the aqueous medium. Cells are incubated in the aqueous medium for an empirically determinable period of time (e.g., about 1 min to about 60 min), at an empirically determinable optimizable temperature (e.g., about 37° C. to about 115° C., preferably about 90° C. to about 115° C.)

For example, in one embodiment, in which both DNA and RNA are released from the cells in a denatured form capable of binding to a protection fragment, the cells are incubated for about 1 min to about 60 min, preferably about 5 to about 20 min, in the aqueous medium at about 90° to about 115° C., preferably about 105° C. If desired, e.g., when it is desirable to assay for DNA in the absence of RNA, any of a variety of conventional ribonucleases can be included in the incubation mixture. Selection of an appropriate ribonuclease, and optimization of digestion conditions, are conventional and readily determined by a skilled worker.

In another embodiment, mRNA can be prepared by incubating cells for about 5 to about 20 min, preferably about 10 min, in an aqueous medium at about 90° to about 100° C., preferably about 95° C., optionally in the presence of one or more protection fragments. In this case, mRNA is substantially released from the cells in a denatured form capable of binding to a protection fragment, and DNA remains substantially inside or attached to the cells, or is unavailable to a probe by virtue of its double-stranded nature, or is released from the cells, but in a form which is not able to bind to a protection fragment (e.g., is not denatured). Without wishing to be bound by any particular mechanism, it appears that, as the nucleic acid is released from the lysed/permeabilized cells, it is sufficiently denatured to allow it to bind to a protection fragment to form a stable duplex which is resistant to degradation by endogenous or exogenous reagents or enzymes, and proteins within the cell (e.g., nucleases) are denatured and/or inactivated.

Following preparation of a nucleic acid of interest by the above procedure, the sample can be diluted, in the appropriate volume, so that the aqueous medium does not inhibit the function of exogenously added proteins such as, e.g., nucleases (e.g., S1 nuclease), polymerases (e.g., polymerases required for PCR reactions), or binding proteins (e.g., streptavidin). The amounts of dilution, and the identity and amounts of the components to be used in the aqueous solution, as described above, can be determined empirically, using conventional methods.

For any of the methods of this invention, targets can be labeled (tagged) by any of a variety of procedures which are well-known in the art and/or which are described elsewhere herein (e.g., for the detection of nuclease protection fragments). For example, the target molecules can be coupled directly or indirectly with chemical groups that provide a signal for detection, such as chemiluminescent molecules, or enzymes which catalyze the production of chemiluminescent molecules, or fluorescent molecules like fluorescein or cy5, or a time resolved fluorescent molecule like one of the chelated lanthanide metals, or a radioactive compound. Alternatively, the targets can be labeled after they have reacted with the probe by one or more labeled target-specific reporters (e.g., antibodies, oligonucleotides as shown in FIG. 1, or any of the general types of molecules discussed above in conjunction with probes and targets).

One type of fluorescent molecule can be an "upconverting phosphore," i.e., a fluor which absorbs and is excited at a long wavelength (e.g, IR), then emits at a shorter wavelength (e.g., visible light). Because upconverting phosphores absorb at a longer wavelength than do most potentially interfering materials present in a typical sample to be analyzed, upconverting phosphores allow a reduction in interference caused by material in the sample, compared to phosphores which absorb at a lower wavelength. The narrow emission spectrum of most upconverting phosphores also allows the simultaneous detection of a large number of different upconverting phosphores. Upconverting phosphores are well-known and conventional in the art, and include, e.g., rare earth metal ions such as, e.g., Ytterbium (Yb), Erbium (Er), Thulium (Tm) and Praseodymium (Pr), particularly in the form of an oxysulfide salt. As many as 80 or more independently detectable upconverting phosphores have been described. (See, e.g., *Biological Agent Detection and Identification*, Apr. 27-30, 1999, DARPA, Biological Warfare Defense, Defense Sciences Office. The phosphores can optionally be attached to any surface, e.g., to a microsphere or a latex bead. Like other fluorescent labels, upconverting phosphores can be detected by energy transfer to (or modulation by) the label on a sufficiently close linker, target or reporter. Furthermore, as with other signaling entities disclosed herein, upconverting phosphores can be used to quantitate the amount of a target, and can be used in any of the variety of procedures described herein, e.g., to detect nuclease protection fragments.

Of course, upconverting phosphores can also be used to detect targets which are distributed in any other fashion on a surface, e.g., targets (including nuclease protection fragments) which are bound directly to a surface, bound directly to an array of different oligonucleotides on a surface, or bound via bifunctional linkers to anchors (different or substantially identical) which are distributed substantially evenly, or in any desired organization or pattern, on a surface.

Any surface can be used, e.g., a flow-through system, or a solid surface such as, e.g., a bead. Beads used in any of the assays of the invention can be of any type, e.g., made of any material, magnetic and/or non-magnetic; and the beads used in a single assay can be of substantially the same, or different, sizes and/or shapes.

A variety of more complex sandwich-type detection procedures can also be employed. For example, a target can be hybridized to a bifunctional molecule containing a first moiety which is specific for the target and a second moiety which can be recognized by a common (i.e., the same) reporter reagent, e.g., a labeled polynucleotide, antibody or the like. The bifunctional molecules can be designed so that any desired number of common reporters can be used in each assay.

For any of the methods of this invention, a variety of complex sandwich-type detection procedures can be employed to label (tag) targets. For example, a target can interact with, e.g., hybridize to, a bifunctional (or multifunctional) molecule (a "detection linker") containing a first moiety that is specific for the target and a second moiety that is specific for a "reporter reagent." The term "specific for" has the meaning as used herein with respect to the interactions of, e.g., probes and targets. The term "reporter reagent," as used herein, refers to a labeled polynucleotide, antibody or any of the general types of molecules discussed herein in conjunction with probes and targets. These two moieties of a detection linker can recognize (interact or associate with) their respective binding partners in any of the manners discussed above in conjunction, e.g., with probes and targets. A detection linker can also comprise other sequences, e.g., sequences that are specific for a target but are different from (non-overlapping with) the target-specific moiety of the corresponding anchor-bound linker. Any sequence present in a detection linker can serve as a recognition sequence for a detection probe or a reporter agent. In a preferred embodiment, a detection linker is a polynucleotide.

Detection linkers can be designed so that any desired number of common reporter reagents can be used in an assay. For example, a set of detection linkers can be designed such that each detection linker is specific for a different target, but comprises a binding site for the same (common), or for one of a limited number of, reporter reagents. The ability to use a limited number of (e.g., one) reporter reagents to label a variety of targets in a single assay provides the advantage of reduced cost and lower backgrounds. Of course, detection linker/reporter reagent combinations can be used to detect targets which are distributed in any fashion on a surface, e.g., as described above for the types of target arrangements that can be detected by upconverting phosphors.

In a most preferred embodiment, detection linkers can be designed to detect nuclease protection fragments in such a way that protection fragments which have been cleaved by a nuclease from control "overhang" sequences during a nuclease protection procedure (as described, e.g., in Example 15) are preferentially labeled. This type of detection procedure is illustrated schematically in FIG. 24. In this embodiment, a detection linker comprises a first moiety that is specific for a target and a second moiety that is specific for the common control overhang sequence which, in a preferred embodiment, is present on substantially all of the nuclease protection fragments at the start of an assay. If, as desired, the control overhang sequence has been cleaved from a nuclease protection fragment during a nuclease protection reaction, the target-specific moiety of the detection linker will hybridize to the cleaved protection fragment, but the control overhang-specific moiety of the detection linker will be unbound and will remain available for further hybridization. If, on the other hand, the control overhang-specific sequence is not cleaved from a protection fragment, e.g., because of incomplete nuclease digestion during a nuclease protection procedure, both the target-specific and the control overhang-specific moieties of the detection linker will hybridize to the protection fragment and will not be available for further hybridization. In a preferred embodiment, complexes comprising nuclease protection fragments and bound detection linkers are then hybridized in a further step to a reporter reagent which comprises a signaling entity (e.g., a fluorochrome, hapten, enzyme, or any other molecule bearing a detectable signal or signal-generating entity, as described herein) and an moiety (e.g., an oligonucleotide) which is specific for the control overhang-specific moiety of a detection linker. The reporter reagent will preferentially bind to and label those complexes in which the control overhang sequence of the nuclease protection fragment has been cleaved off, (i.e., a complex in which the control overhang-specific moiety of the detection linker is available for further hybridization to the reporter reagent.)

Numerous other variations of sandwich detection procedures will be evident to one of skill in the art.

Methods by which targets can be incubated with a target-specific reporter(s), or target/detection linker complexes can be incubated with reporter reagents, under conditions effective for achieving binding or other stable interaction, are routinely determinable (see above). For example, fluorescent oligonucleotide reporters (at a concentration of about 10 nM to about 1 µM or more, preferably about 30 nM, in a buffer such as 6×SSPE-T or others) can be incubated with the bound targets for between about 15 minutes to 2 hours or more (preferably about 30 to 60 minutes), at a temperature between about 15° C. and about 45° C. (preferably about room temperature). After incubation, the samples can optionally be treated (e.g., washed) to remove unbound target-specific reporters, using conditions which are determined empirically to leave specific interactions intact, but to remove non-specifically bound material. For example, samples can be washed between about one and ten times or more under the same or somewhat more stringent conditions than those used to achieve the target/reporter binding.

Tagging with a target-specific reporter(s) can provide an additional layer of specificity to the initial hybridization reaction, e.g., in the case in which a target-specific oligonucleotide reporter is targeted to a different portion of the sequence of a target nucleic acid than is the probe oligonucleotide, or in which probe and reporter antibodies recognize different epitopes of a target antigen. Furthermore, tagging with target-specific reporters can allow for "tuning" the sensitivity of the reaction. For example, if a target mRNA which is part of a correlative expression pattern is expressed at very low levels, the level of signal can be enhanced (signal amplification) by hybridizing the bound target to several (e.g., about two to about five or more) target-specific oligonucleotide reporters, each of which hybridizes specifically to a different portion of the target mRNA.

The ability to detect two types of labels independently allows for an additional type of control in MAPS assays. Some (e.g., about 10 to about 100%) of the linkers designated for a particular anchor locus (FIG. 7 shows 3 typical anchor loci, each comprising a plurality of substantially identical anchors (A, B or C)) can have a label (e.g., a fluor) attached to one end. For example, a rhodamine or Cy5 fluor can be attached at the 5' end of the linker. Such modified linkers are termed "control linkers." After a mixture of linkers and control linkers has been associated with anchors and a sample containing a target has been incubated with the resulting probe array, a target-specific reporter bearing a different fluor (e.g., fluorescein or another detection label such as a chemiluminescent one) can be used (or the target can be directly labeled with a fluor or other detection label); and the ratio of the two signals can be determined. The presence of control linkers permits calibration of the number of functional (e.g., able to interact with linkers) anchors within and between test regions (i.e. tests the capacity of each locus of the array to bind target, for purposes of normalizing signals), serves as a basis for quantitation of the amount of bound target, aids in localization of the anchor loci and/or provides a positive control, e.g., in cases in which there is no signal as a result of absence of target in a sample. In one embodiment of the invention, two different labels (e.g., fluorophores) can also be used to detect two different populations of target molecules; however, the ability to recognize the presence of targets by spatial resolution of signals allows the use of a single type of label for different target molecules.

The ability to detect labels independently (e.g., fluorescent labels which emit at distinguishable wavelengths, such as, e.g., fluorescein and rhodamine, or different upconverting phosphors) allows additional flexibility in the methods of the invention. For example, each of two or more targets can be labeled, directly or indirectly, with its own, uniquely detectable, label. This allows for the detection of targets on the basis of features specific to the labels (e.g., color of the emission) in addition to (or instead of), e.g., identifying the position of a localized target on a surface, or identifying a target by virtue of the size of a bead to which it is localized. In another embodiment of the invention, a multiplicity of targets can be detected independently at a single locus within a region. For example, two or more (e.g., 2, 3, 4, 5, 6 or more) targets can be detected at a locus which is defined by a single group of (substantially identical) anchors. That is, a set of linkers can be used, each of which has an anchor-specific portion specific for the same anchor plus a target-specific portion specific for a different target. If a set of, e.g., four such linkers is used, all four can bind to members of the group of anchors at a single locus, allowing four different targets to bind at that locus. If each of these targets is labeled (directly or indirectly) with a different, distinguishable, label, an investigator can determine the presence of each of the four targets at the locus independently. Therefore, an array of, e.g., five anchors (groups of anchors) in a region can be used in the scenario described above to detect as many as twenty different targets. Such an assay is illustrated in Example 24 and FIG. 25. Similarly, a plurality of targets, e.g., as many as 80 or more, can be detected independently when a single type of anchor is distributed, not at a single locus, but evenly, or in any desired fashion, on a solid surface such as, e.g., a bead or a flow through apparatus; and other aspects such as bead size or scatter can be used to provide information about target identity or groups of targets.

The association of multiple linkers (e.g., ranging from about two to about 50 or more), having different target specificities, with the anchors at a given locus (either a group of substantially identical anchors or a "mixed locus"), sometimes referred to herein as "mixed linkers," forms the basis for other embodiments of the invention, which will be evident to those of skill in the art. For example, at a given locus the anchors can be bound to a mixture of linkers which are specific for a plurality of different protection fragments, each of which corresponds to (is specific for) a different portion of a nucleic acid (e.g., an mRNA) of interest. The presence of such a plurality of different linkers at a locus allows for considerably increased sensitivity in the detection of a target (e.g., an mRNA) of interest, e.g., one present at low abundance in a sample. Each locus can be designed so that the number of linkers corresponding to different portions of an mRNA designated for that locus is inversely proportional (in an empirically determinable fashion) to the abundance of that mRNA in the sample. For example, if one mRNA of interest is found in a preliminary experiment to be present in a sample in large excess over a second mRNA of interest, the relative number of linkers corresponding to different portions of the two mRNAs can be adjusted so that the relative intensities of the signals corresponding to each mRNA are substantially the same. That is, the signal intensities can be adjusted so that the signal corresponding to the first mRNA does not swamp out the signal corresponding to the second mRNA. In this manner, one can adjust an assay to allow for simultaneous detection of a plurality of mRNAs which are present in widely different amounts in a sample, balancing the signal intensity corresponding to each mRNA.

In another embodiment of the invention, as was noted above, a given locus can comprise linkers which are specific for a plurality of unrelated or different targets or protection fragments, allowing for the detection of a greatly increased number of targets or protection fragments with a single array of anchors. If, for example, each locus of an array of 350 anchors comprises linkers specific for 10 different targets, then the array can be used to detect as many as 3500 targets. In effect, such an arrangement allows one to convert an array which can detect a low density of targets to one which can detect a high density of targets.

Multiple molecules (e.g., protection fragments) bound at a single locus can be detected sequentially or simultaneously, e.g., using the detection methods described elsewhere in this application. (For a discussion of "detection linkers" and "reporter reagents," see, e.g., the section above concerning complex sandwich-type detection methods.) In one embodiment, a first target (e.g., a protection fragment) at a given locus is detected, e.g., with a first detection system (e.g., a detection linker/reporter reagent, or a detection probe specific for it); then that first detection linker/reporter reagent or probe is removed or inactivated, using conventional procedures (e.g., changing the pH to inactivate a reporter reagent comprising an enzyme that generates a chemoluminescent signal), and a second detection linker/reporter reagent or detection probe specific for a second target at the same locus is used to detect that second target; and so forth for as many cycles as desired. In another embodiment, the first detection linker/reporter reagent or detection probe is added to a combination as above, but it is not removed or inactivated before the second detection linker/reporter reagent or detection probe is added. In this embodiment, the amount of signal corresponding to the second target can be determined by subtracting out the amount of signal corresponding to the first target. In another embodiment, the first and second detection linker/reporter reagents or detection probes are added to the combinations as above, substantially simultaneously, and are detected individually, e.g., using differentially detectable labels as described elsewhere herein. In any of the detection methods described herein, the detection linkers can comprise moieties which are specific for the same or for different reporter reagents. For example, if four targets are associated with the linkers at a given locus, the detection linkers specific for each of the four targets can each comprise a moiety specific for a different reporter reagent. Therefore, after the set of all four detection linkers is hybridized to the targets, the targets can be detected sequentially or simultaneously, as described above, using the four different reporter reagents.

Other detection methods, as well as combinations of the above methods, will be evident to one of skill in the art.

Of course, "mixed linkers" are also advantageous for use with surfaces which contain a single (non-repeated) region.

In another embodiment of the invention, "anchors" which are specific for a target(s) of interest are not associated with linkers, but rather are associated directly with the target(s); the target(s), in turn, can interact optionally with detection linker(s) or with detection probe(s).

Targets, whether labeled or unlabeled, can be detected by any of a variety of procedures, which are routine and conventional in the art (see, e.g., Fodor et al (1996). U.S. Pat. No. 5,510,270; Pirrung et al (1992). U.S. Pat. No. 5,143,854; Koster (1997). U.S. Pat. No. 5,605,798; Hollis et al (1997) U.S. Pat. No. 5,653,939; Heller (1996). U.S. Pat. No. 5,565,322; Eggers et al (1997). U.S. Pat. No. 5,670,322; Lipshutz et al (1995). *BioTechniques* 19, 442-447; Southern (1996). *Trends in Genetics* 12, 110-115). Detection methods include enzyme-based detection, colorimetric methods, SPA, autoradiography, mass spectrometry, electrical methods, detection of absorbance or luminescence (including chemiluminescence or electroluminescence), and detection of light scatter from, e.g., microscopic particles used as tags. Also, fluorescent labels can be detected, e.g., by imaging with a charge-coupled device (CCD) or fluorescence microscopy (e.g., scanning or confocal fluorescence microscopy), or by coupling a scanning system with a CCD array or photomultiplier tube, or by using array-based technology for detection (e.g., surface potential of each 10-micron part of a test region can be detected or surface plasmon resonance can be used if resolution can be made high enough.) Alternatively, an array can contain a label (e.g., one of a pair of energy transfer probes, such as fluorescein and rhodamine) which can be detected by energy transfer to (or modulation by) the label on a linker, target or reporter. Among the host of fluorescence-based detection systems are fluorescence intensity, fluorescence polarization (FP), time-resolved fluorescence, fluorescence resonance energy transfer and homogeneous time-released fluorescence (HTRF). Analysis of repeating bar-code-like patterns can be accomplished by pattern recognition (finding the appropriate spot or line for each specific labeled target by its position relative to the other spots or lines) followed by quantification of the intensity of the labels. Bar-code recognition devices and computer software for the analysis of one or two dimensional arrays are routinely generated and/or commercially available (e.g., see Rava et al (1996). U.S. Pat. No. 5,545,531).

Another method which can be used for detection is 2-photon fluorescence, including applications where the fluorescence of endogenous or conjugated fluorochromes of components bound to the array surface is enhanced by being bound close to the surface of the array, for instance by close apposition to the substrate on which the array is formed, or by close apposition to other agents included in the anchor or linker or otherwise incorporated in the bound complex. Other fluorescence methods or utility include lifetime fluorescence, polarization, energy transfer, etc. For instance, such methods permit the simultaneous detection and discrimination of multiple targets within the same locus, and in some instances can discriminate between bound label and unbound label, eliminating the need to wash unbound lable away from the array, and thus facilitating the measurment of rapidly reversible or weak interactions by the array.

Methods of making and using the arrays of this invention, including preparing surfaces or regions such as those described herein, synthesizing or purifying and attaching or assembling substances such as those of the anchors, linkers, probes and detector probes described herein, and detecting and analyzing labeled or tagged substances as described herein, are well known and conventional technology. In addition to methods disclosed in the references cited above, see, e.g., patents assigned to Affymax, Affymetrix, Nanogen, Protogene, Spectragen, Millipore and Beckman (from whom products useful for the invention are available); standard textbooks of molecular biology and protein science, including those cited above; and Cozette et al (1991). U.S. Pat. No. 5,063,081; Southern (1996), *Current Opinion in Biotechnology* 7, 85-88; Chee et al (1996). *Science* 274, 610-614; and Fodor et al (1993). *Nature* 364, 555-556.

BRIEF DESCRIPTION OF THE DRAWINGS

FIG. 5*a* represents a well separator; FIG. 5*b* represents a subdivider; and FIG. 5*c* represents a base.

FIG. 17 illustrates an assay to detect peptides containing phosphotyrosine residues.

cDNAs or mRNAs generated from the genes from which the ESTs were obtained are added to all 16 wells and allowed to hybridize under appropriate conditions. Hence, any cDNA or mRNA that contains one of the 16 EST sequences will be assembled at the locus where its complementary probe was placed.

Figure 19:
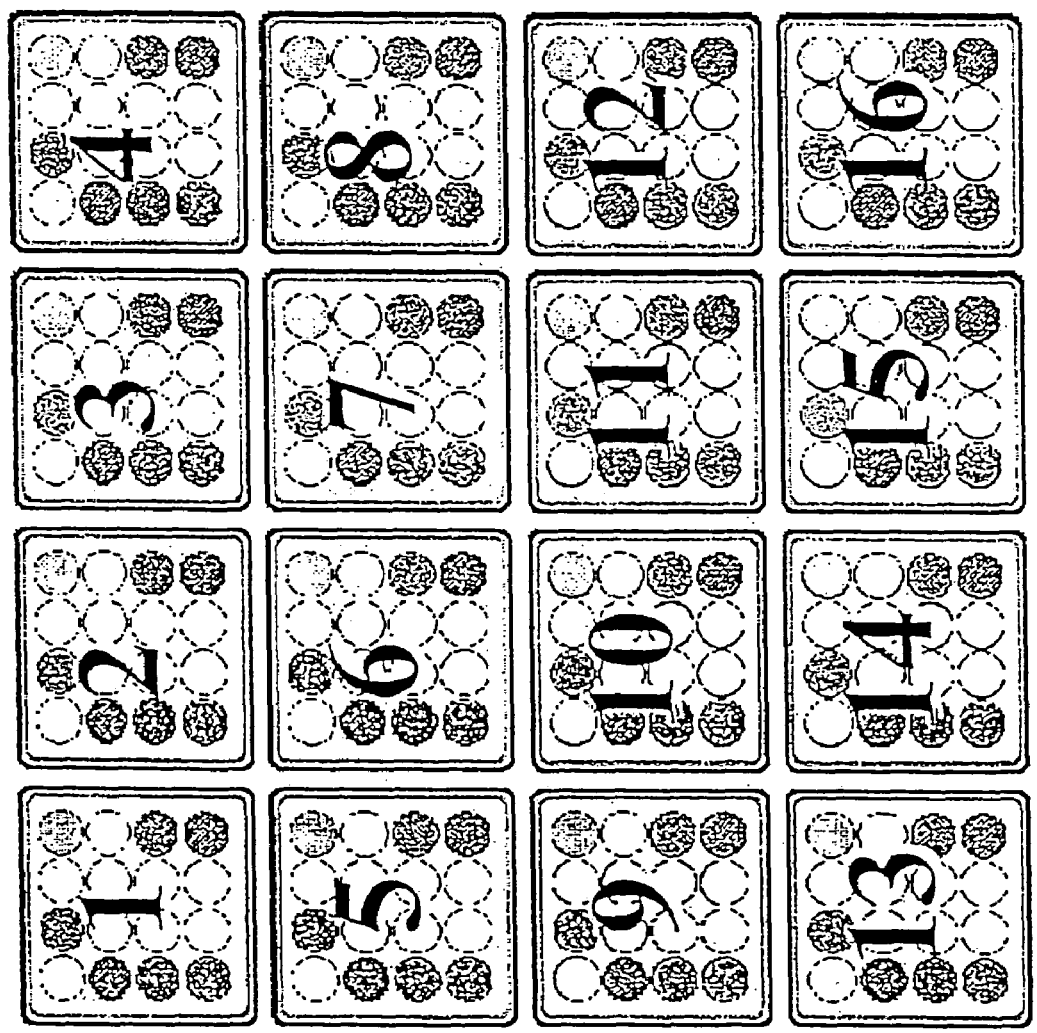

FIG. 19 illustrates a subsequent step in an assay to map ESTs: adding detector oligonucleotides to the MAPS plate. Each well of the plate receives a detector oligonucleotide which corresponds to one of the ESTs to be mapped. Each detector oligonucleotide is an oligonucleotide coupled to a molecule used for detection, e.g., fluorescein if fluorescence imaging is to be the method of detection. Each detector oligonucleotide is complementary to one of the ESTs, but different from the EST-specific probe, so that a probe and a detector oligonucleotide which are complementary to a single EST can both bind at the same time.

After washing, a single detector oligonucleotide is added to each well, as numbered in the figure. That is, the detector oligonucleotide with sequences complementary to the first EST is added to the first well, and so on.

Figure 18:
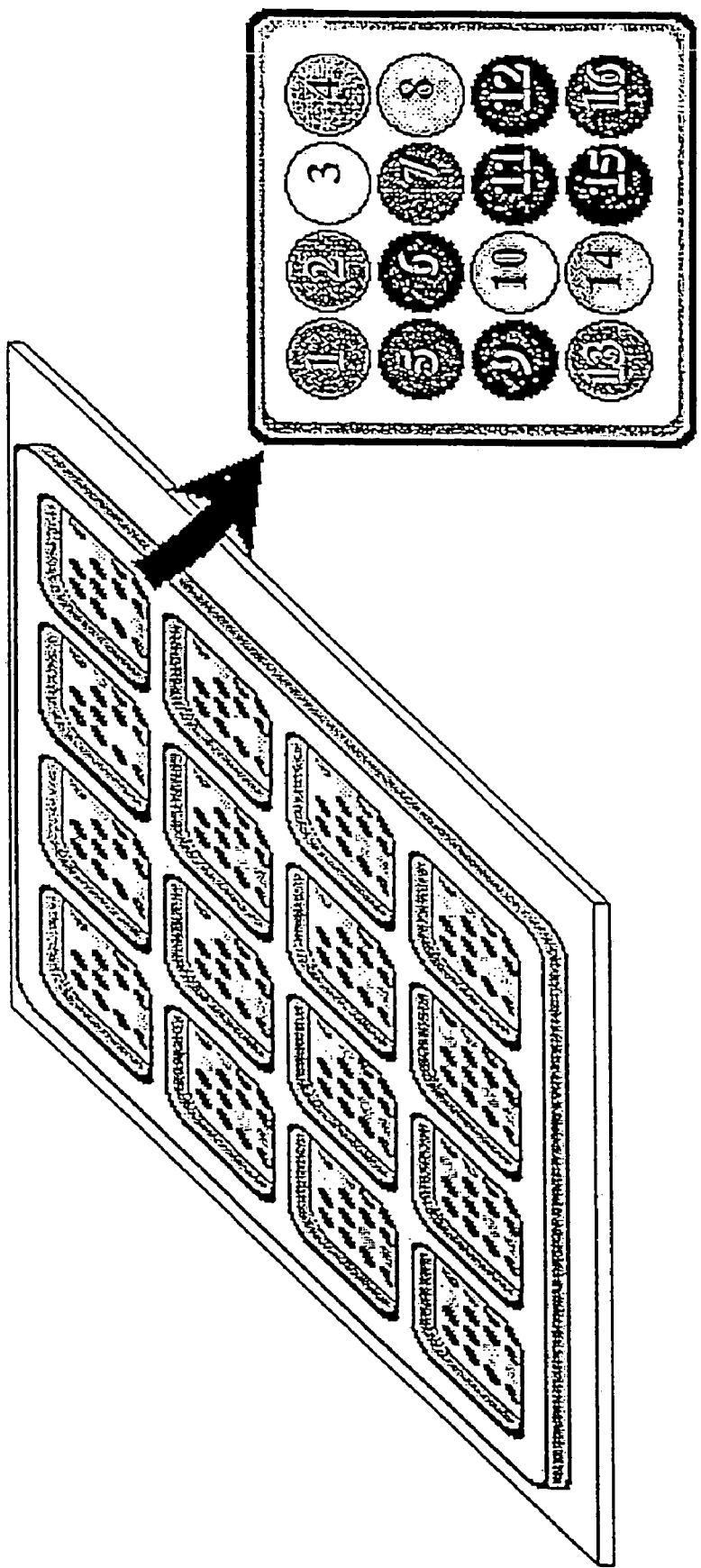
FIG. 18 illustrates the first step in an assay to map ESTs: assembling linkers corresponding to each of the ESTs to be mapped on arrays of generic anchors on a MAPS plate. To the surface of each of 16 wells of a microplate are attached linkers comprising 16 different oligonucleotide probes, arranged in a 4×4 matrix. The first locus has oligo 1, which is complementary to a portion of the first EST sequence, and so on for the 16 ESTs to be tested.
Figure 20B:
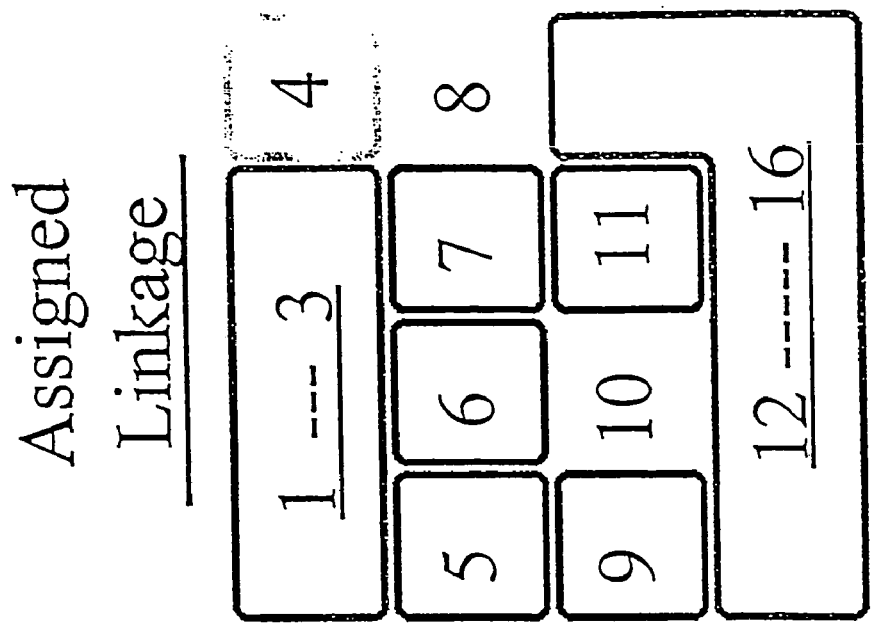
Figure 20A:
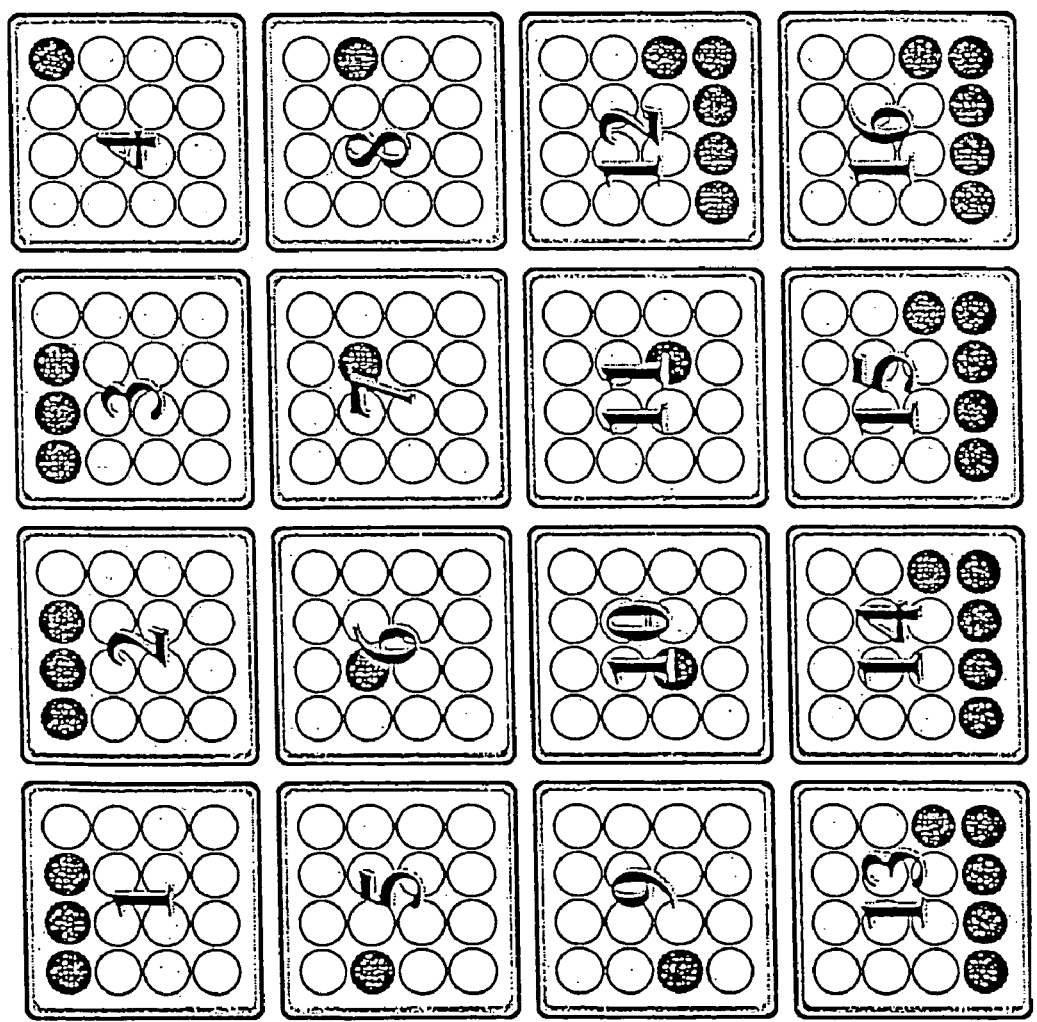

FIGS. 20*a* and *b* illustrate the results of the assay to map ESTs shown in FIGS. 18 and 19. After hybridization of detector oligonucleotides and washing with appropriate conditions of stringency, the 16 wells of the microplate are imaged with a CCD-based fluorescence imager, for example. FIG. 20*a* shows stylized results. It is expected that each EST-specific detector oligonucleotide should label the mRNA or cDNA held down by the corresponding EST-specific probe. For example, probe 5 assembles the cDNA or mRNA containing the fifth EST sequence at that locus, so the fifth detector oligonucleotide should also hybridize to the cDNA or mRNA at the same locus. This is the case for these stylized data, with each detection oligonucleotide labeling the matching probe. In addition, the first three detector oligonucleotides each label cDNA or mRNA held down by the first three probes, showing that these sequences lie along the same gene. Similarly, the last five ESTs appear to be linked. The linkage assigned from these data are presented graphically in FIG. 20*b*.

Figure 21:
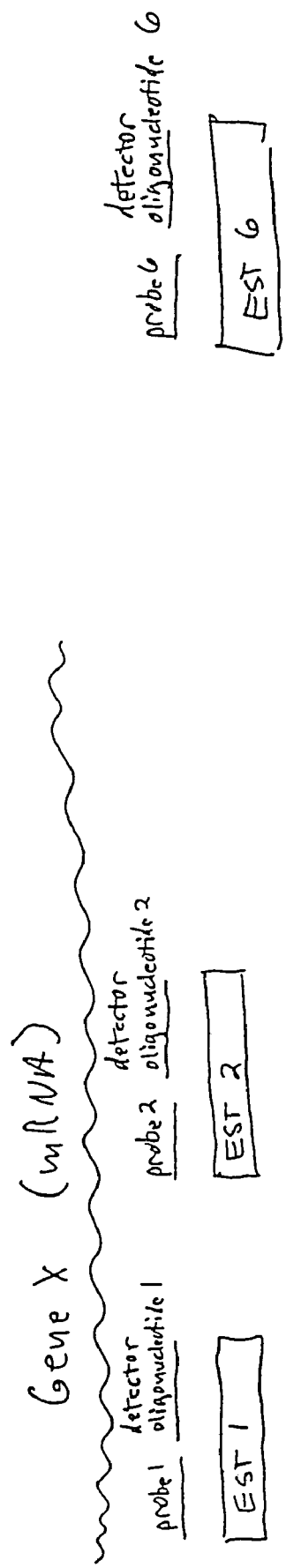

FIG. 21 illustrates the relationships of the probes, detector oligonucleotides and ESTs #1, 2 and 6 shown in FIGS. 18-20.

Figure 22:
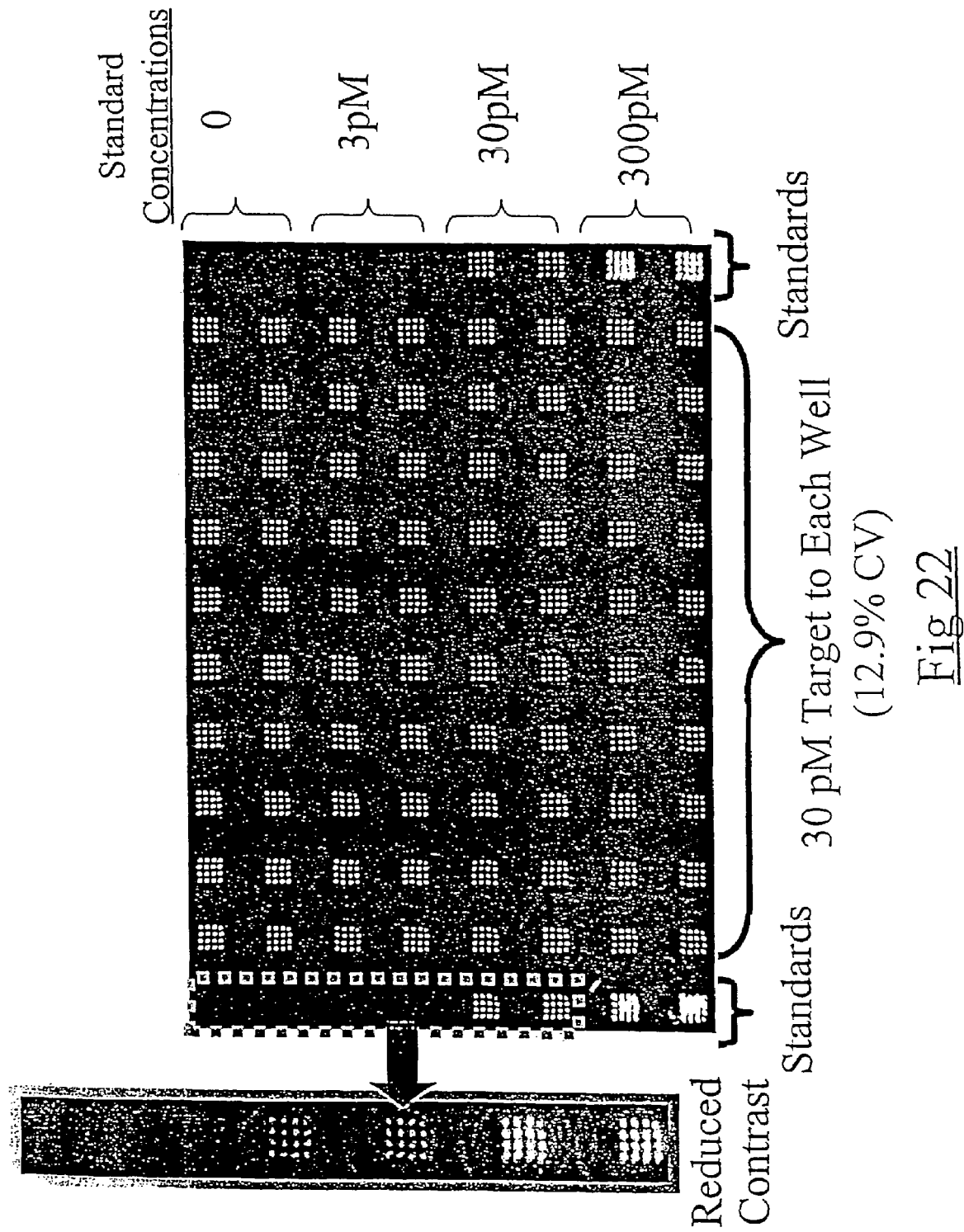

FIG. 22 illustrates a high throughput assay.

Figure 23:

FIG. 23 illustrates a method to prepare an amplified target.

Figure 24:
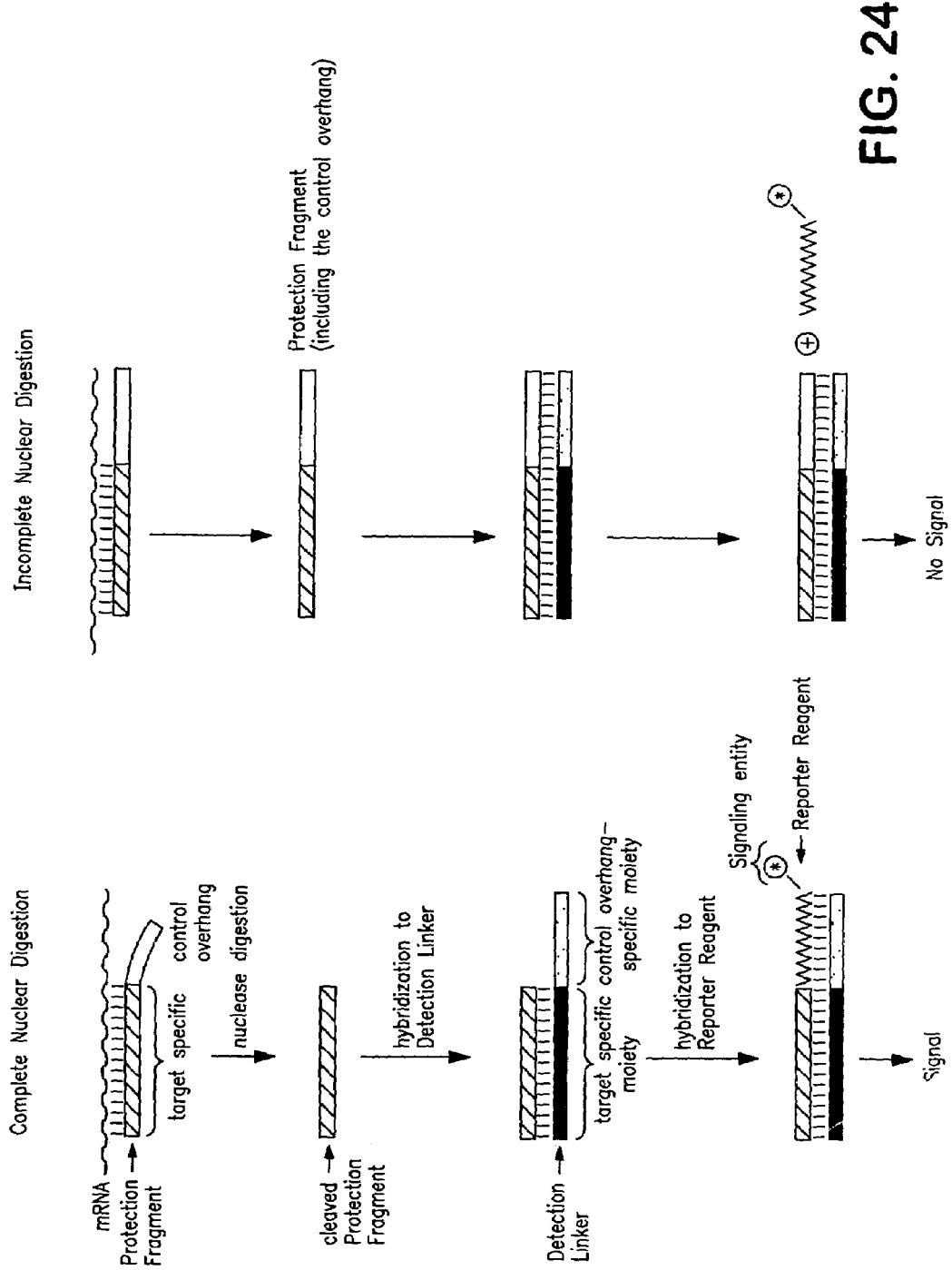

FIG. 24 illustrates an assay with detection linkers and reporter agents.

Figure 25:
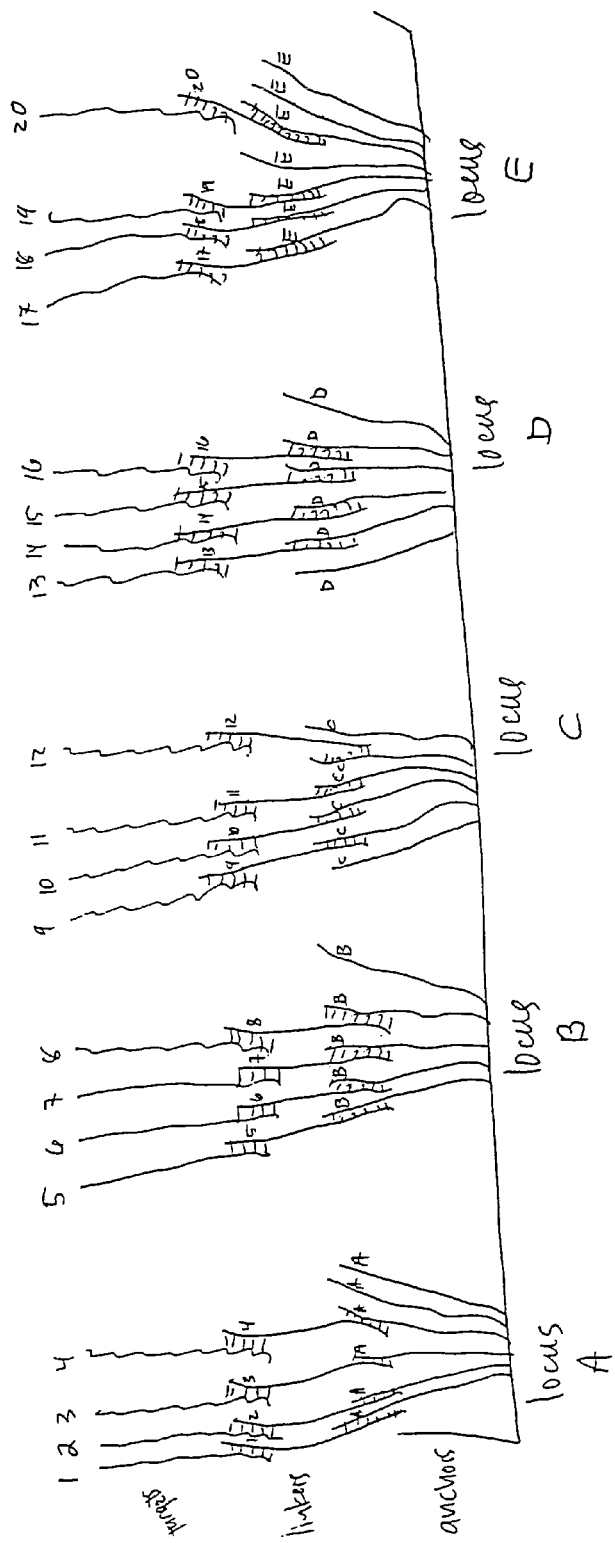

FIG. 25 illustrates a use of multiple flours.

Figure 26:
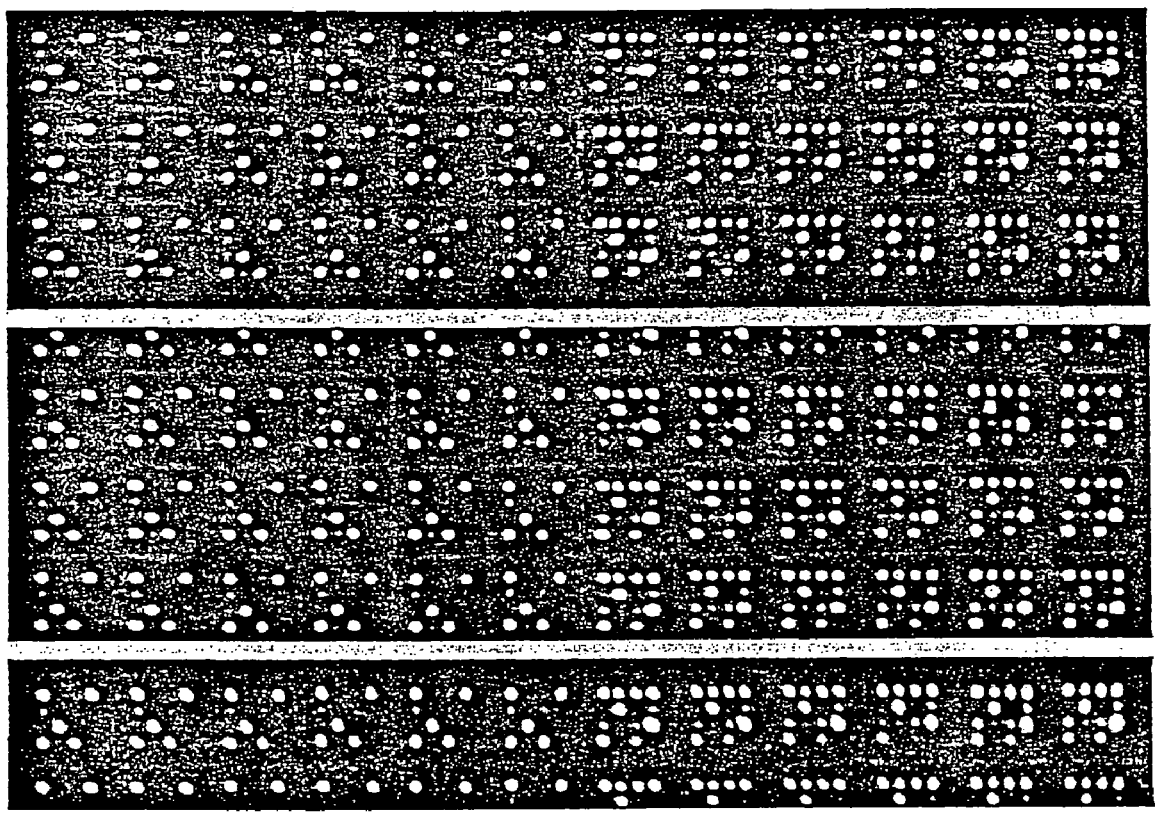

FIG. 26 illustrates a high throughput assay.

Figure 27:
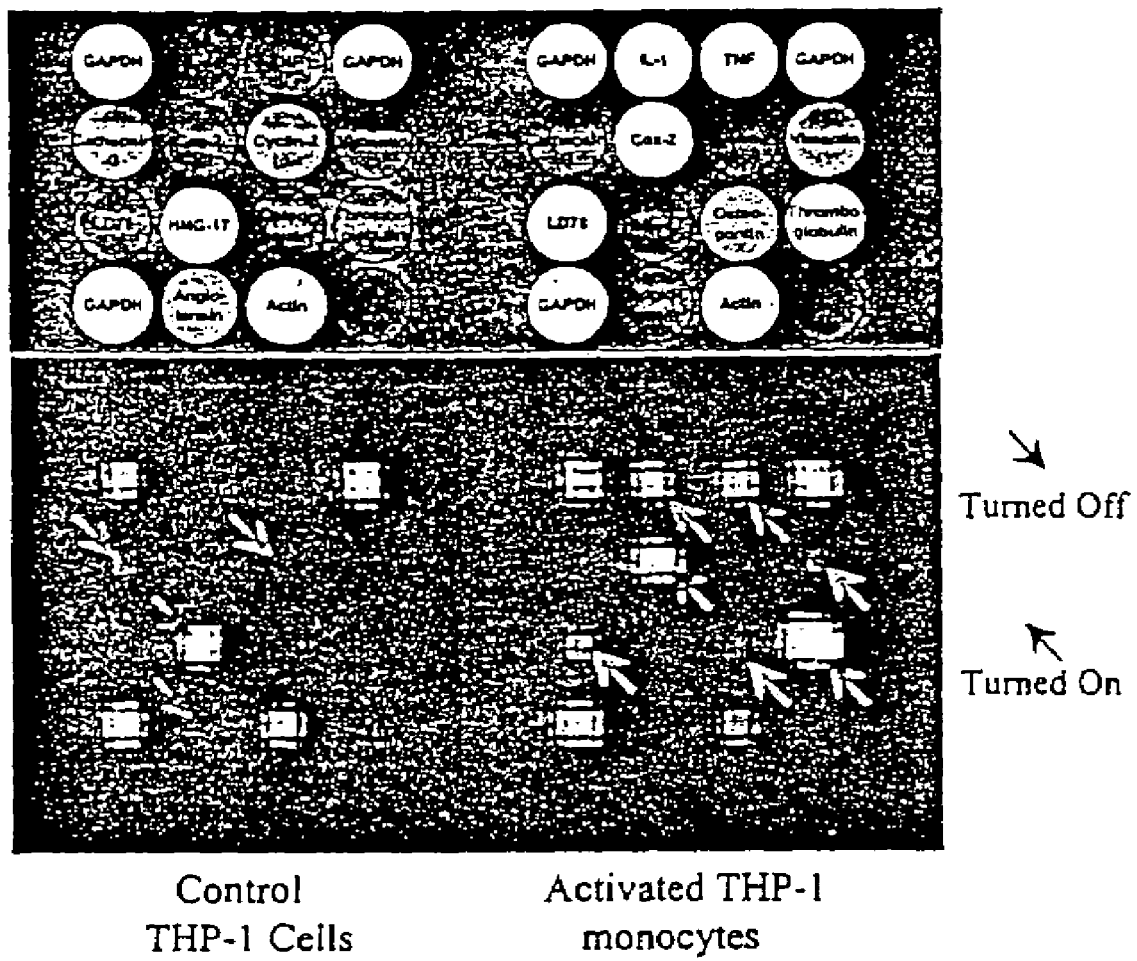

FIG. 27 illustrates the spatial arrangement of genes for the THP-1 cells, along with two sample cells of data (selected from FIG. 26).

Figure 28:
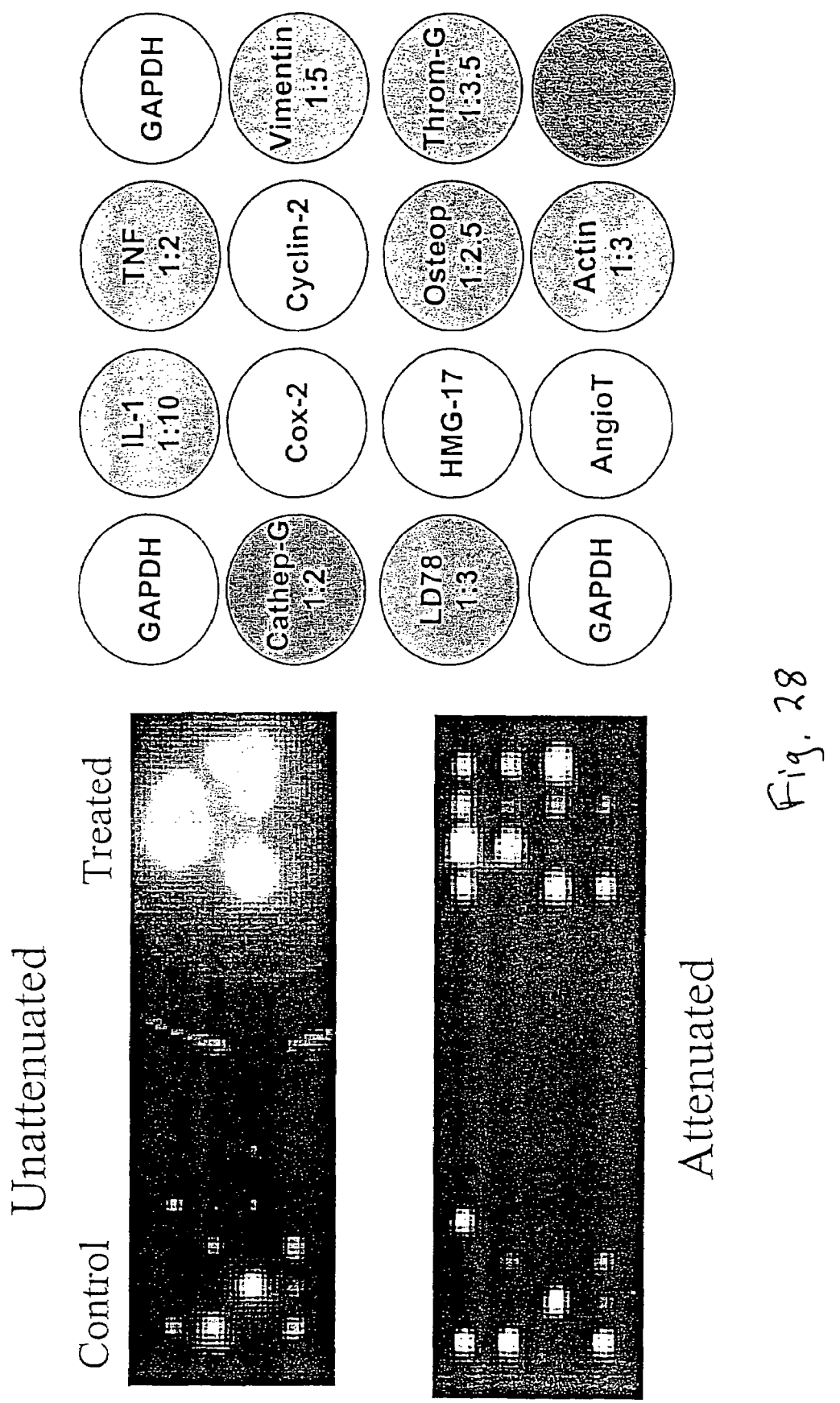

FIG. 28 illustrates an assay with signal attenuation.

FIG. 29 illustrates an assay in which genomic DNA and expressed RNA are measured from the same sample in the same well, e.g., in which genomic DNA serves as a normalization control. The left panel depicts the measurement of DNA alone; the right panel depicts the measurement of both the DNA and GAPDH RNA (measured in each corner of the array).

Figure 30:
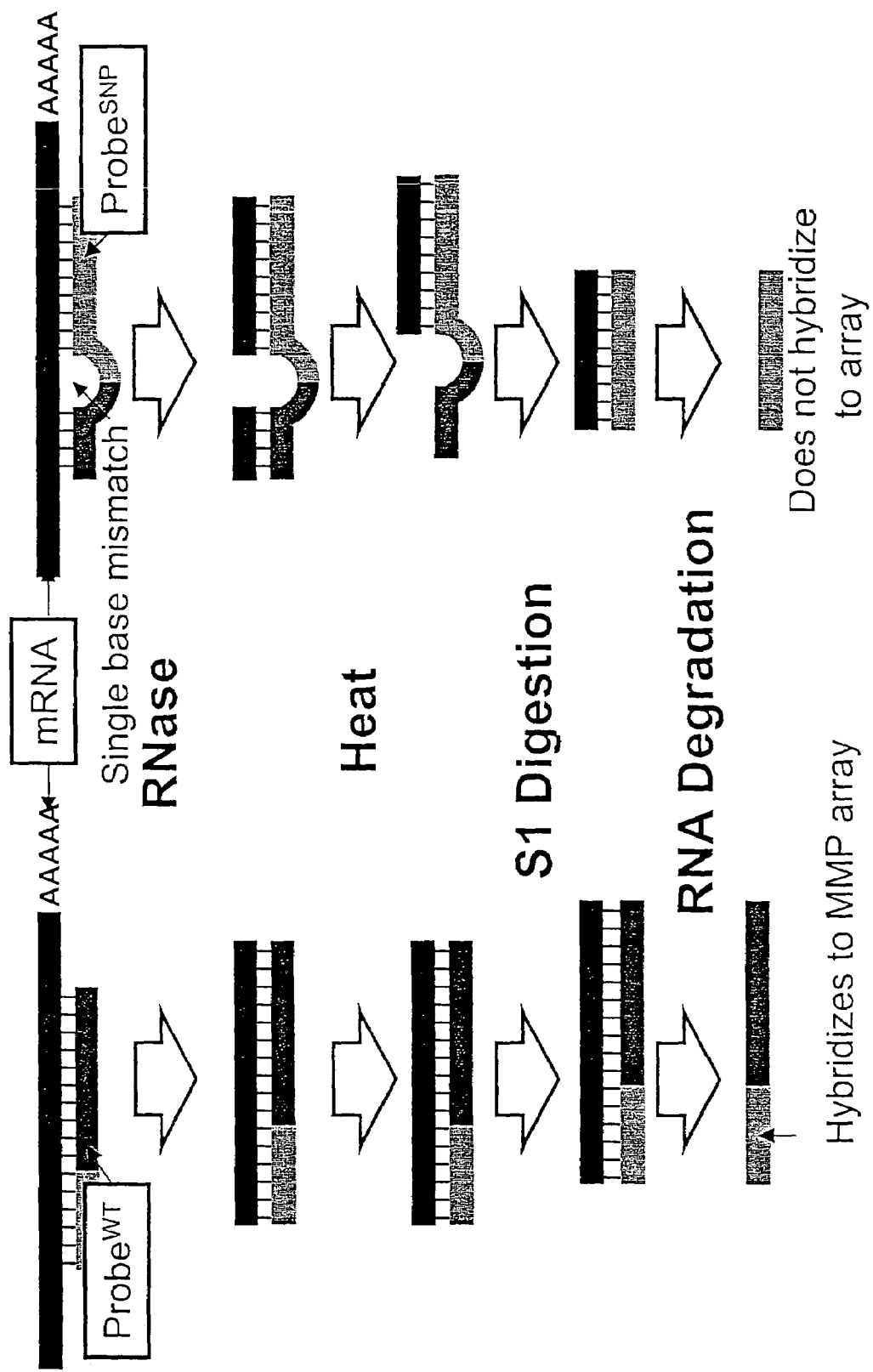
Figure 31:
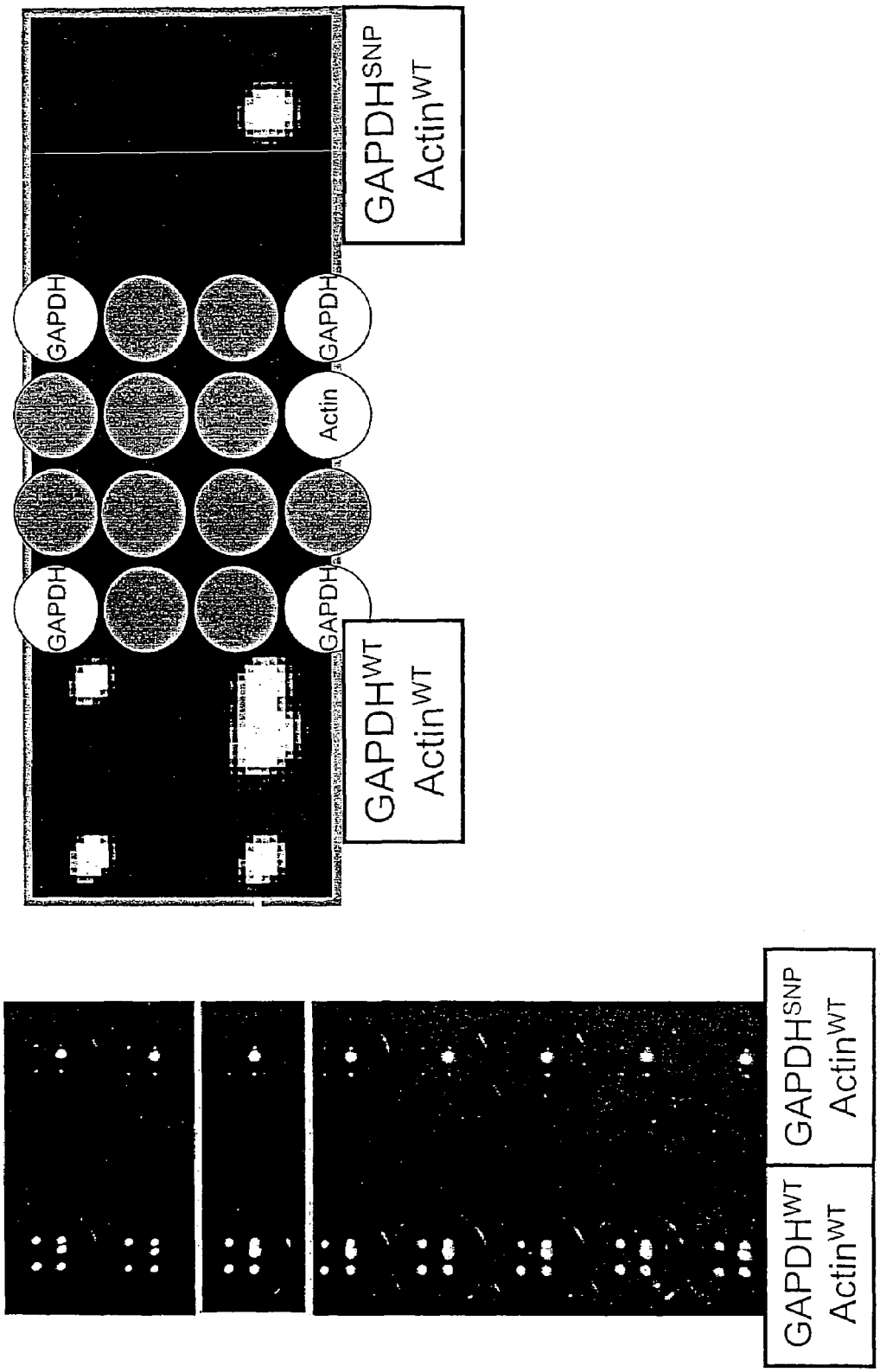

FIGS. 30 and 31 illustrate the detection of expressed SNPs.

FIGS. 32-35 illustrate the sensitivity and reproducibility of an assay.

Figure 36:
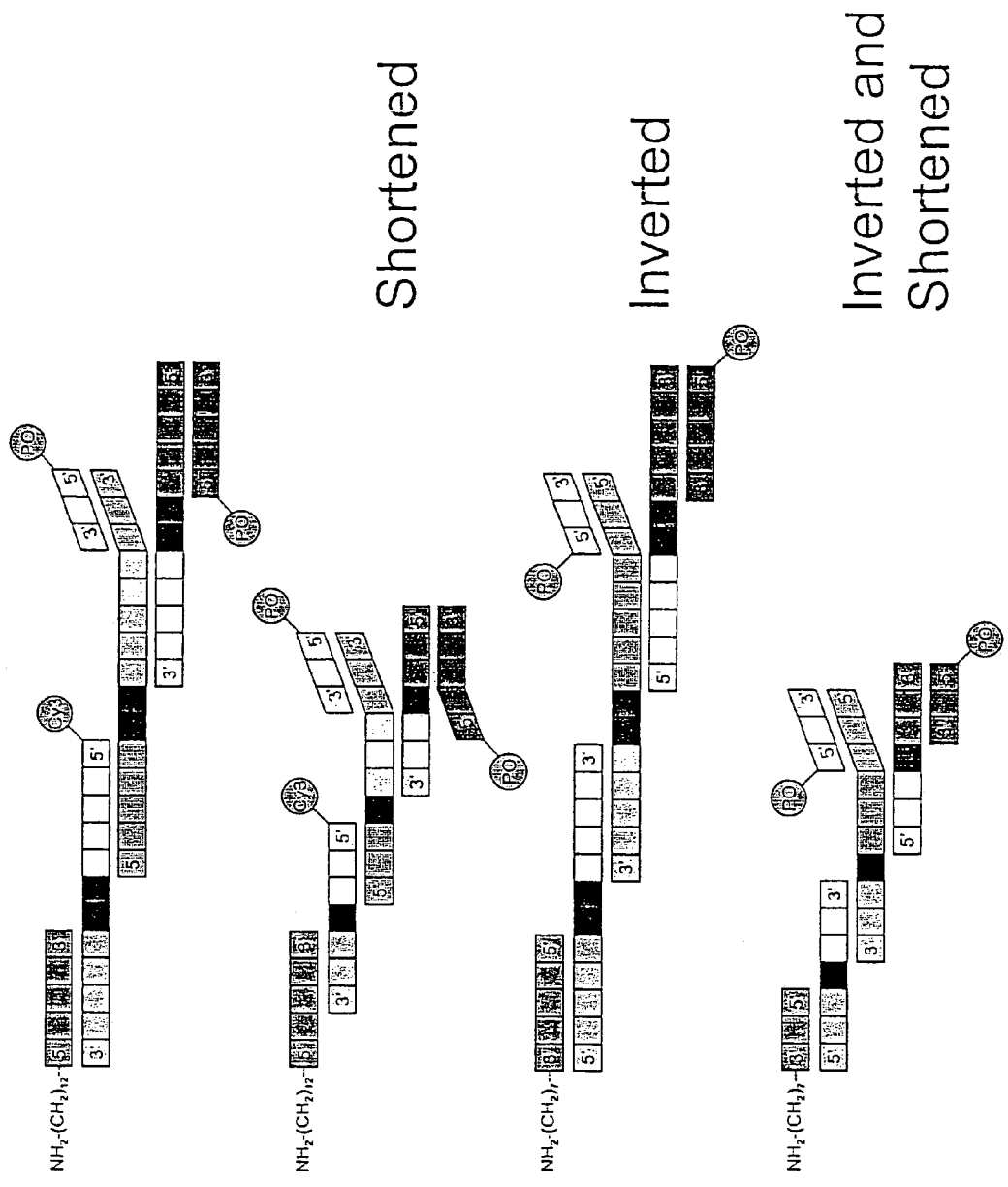

FIG. 36 illustrates some types of assay configurations encompassed by the invention.

Figure 37:
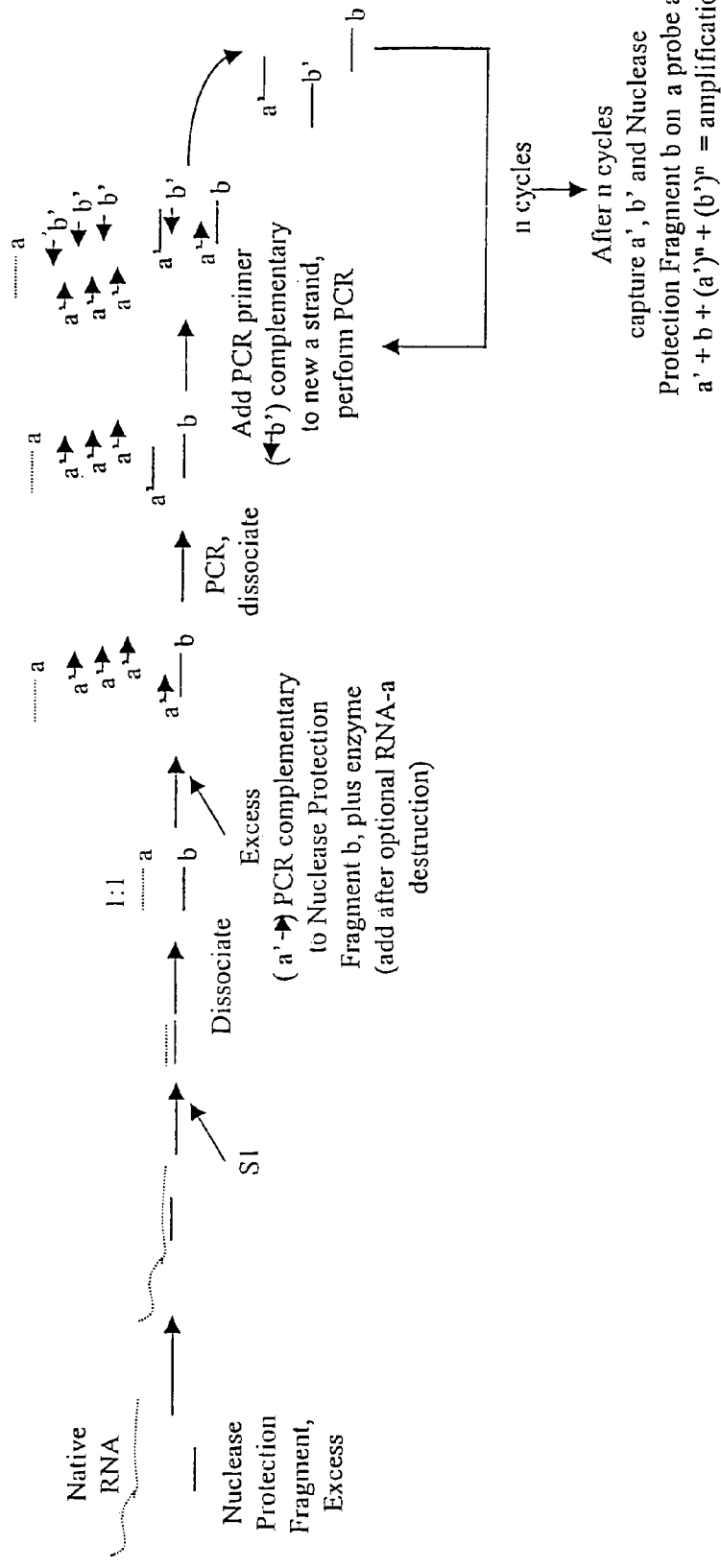

FIG. 37 illustrates nuclease protection fragment amplification by PCR.

Figure 38:
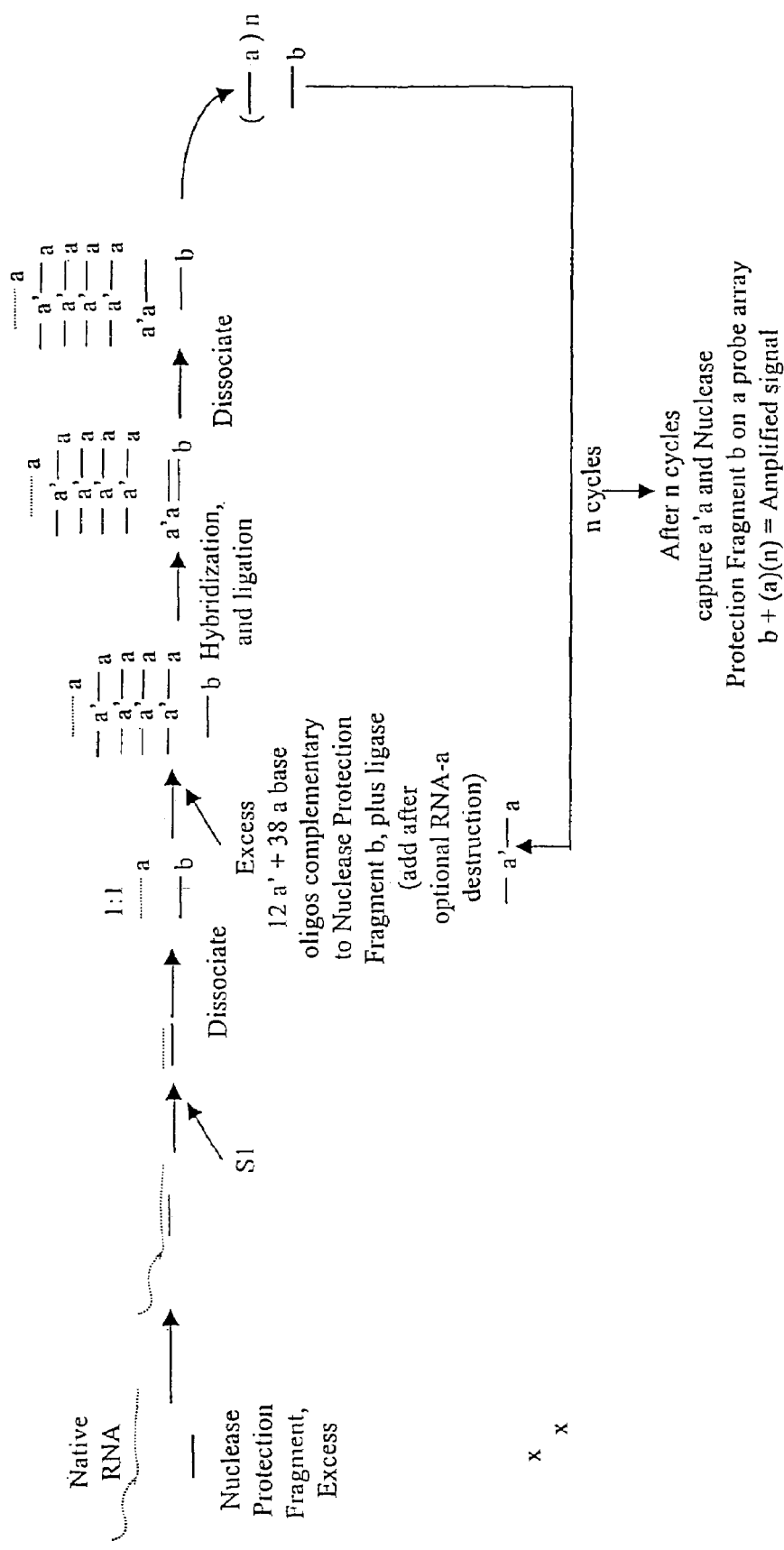

FIG. 38 illustrates nuclease protection fragment amplification by Ligase.

Figure 39:
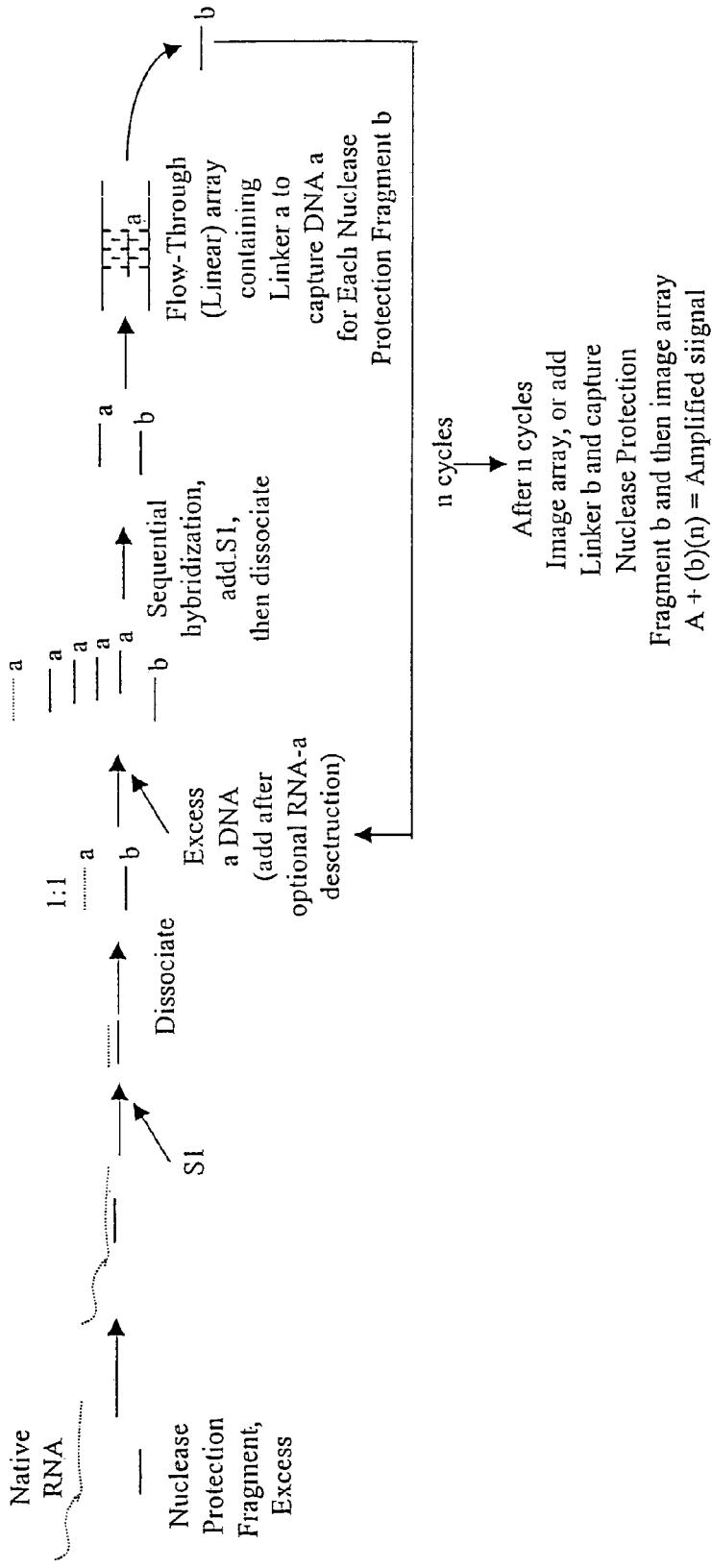

FIG. 39 illustrates nuclease protection fragment amplification by Nuclease Protection.

Figure 40:
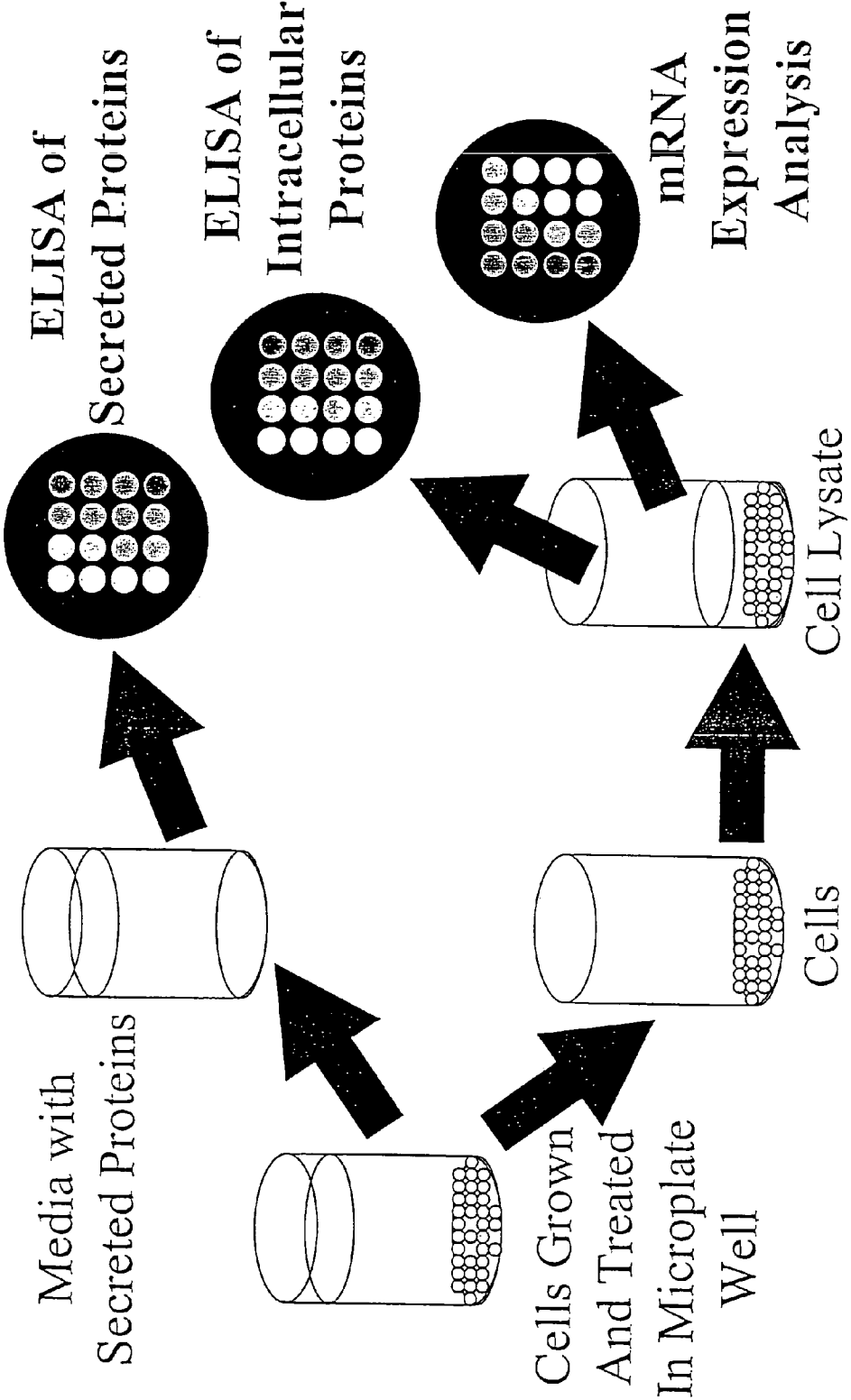
Figure 41:
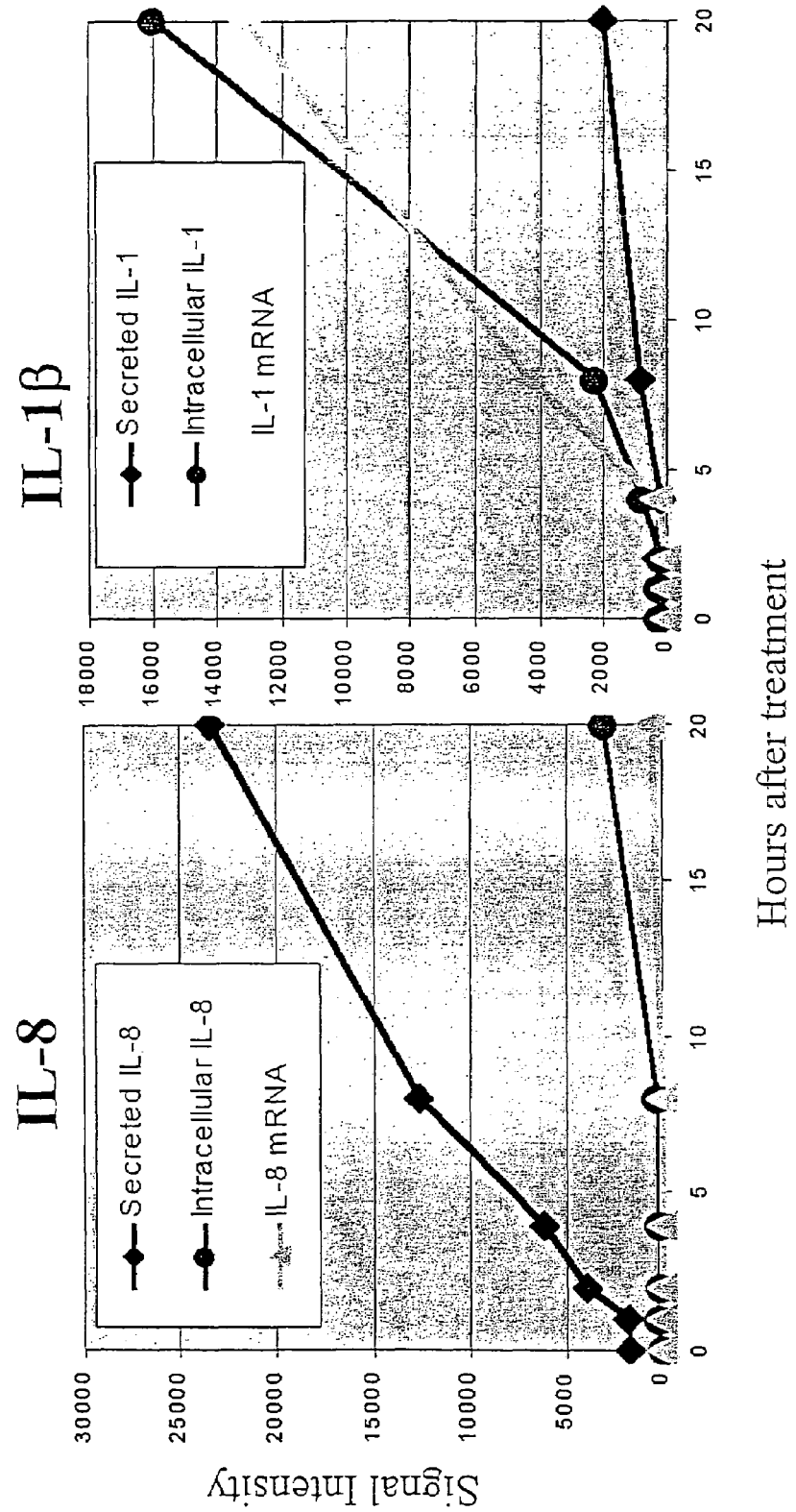

FIGS. 40 and 41 illustrate assays in which, e.g., protein and mRNA are assayed together from the same sample.

Figure 42:
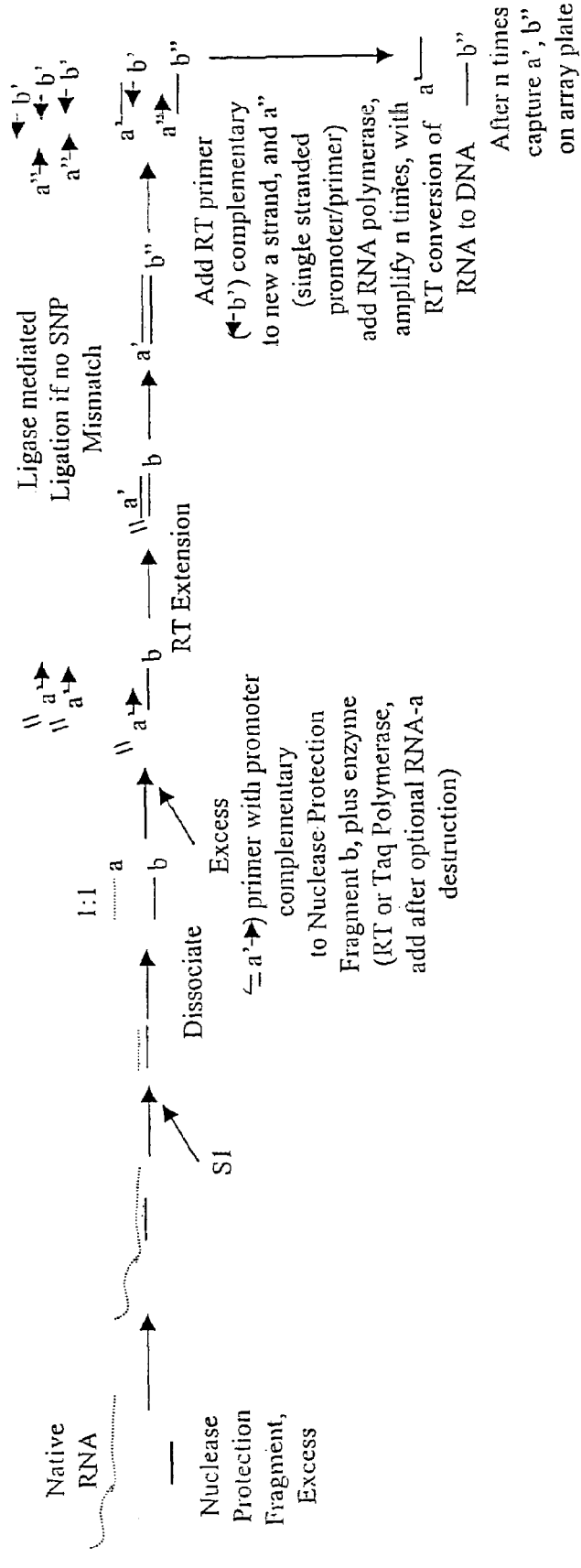

FIG. 42 illustrates nuclease protection fragment amplification by polymerase. An application for the detection of SNPs is illustrated.

EXAMPLES

Example 1

Figure 10:
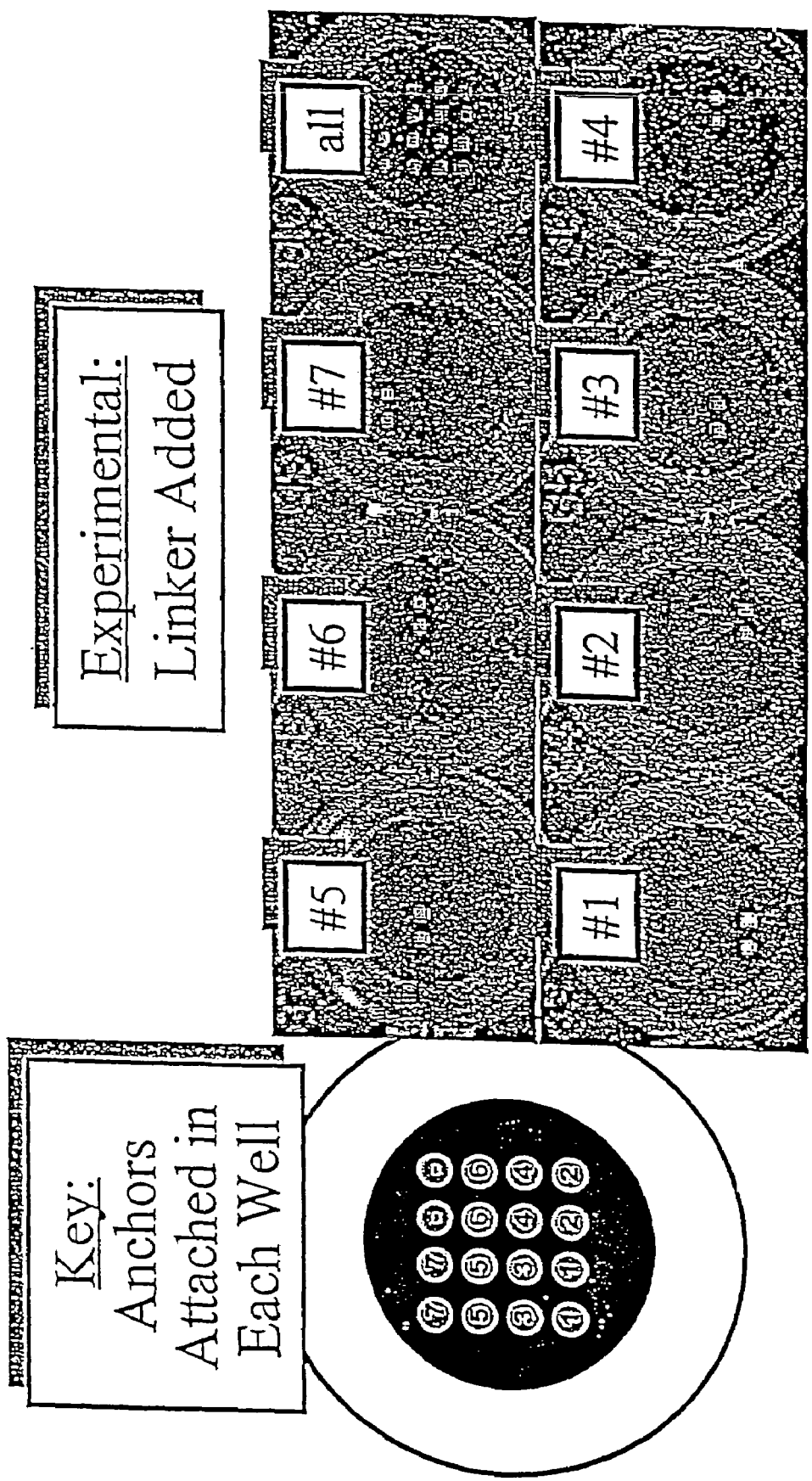
FIG. 10 illustrates hybridization specificity in a MAPS assay.

Hybridization Specificity (see FIG. 10)

A generic MAPS plate was produced by using an inkjet dispenser, the Pixus system (Cartesian Technologies, Inc., Irvine, Calif.) to form an identical grid of DNA within each well of a microtiter plate. All oligonucleotides were purchased from Biosource International (Camarillo, Calif.). For this plate, seven different oligonucleotide anchors were dispensed within each well in the pattern shown as the Key (left side of the figure). Each oligonucleotide was dispensed as a 10 nanoliter droplet to two spots, from a 2 uM solution containing 500 mM sodium phosphate pH 8.5 and 1 mM EDTA to the wells of a DNA Bind plate (Corning Costar), and allowed to dry. After attachment, wells were blocked with 50 mM Tris pH 8, and then oligonucleotide that had not covalently attached to the surface was washed away with 0.1% SDS in 5×SSP buffer.

To the washed plate fluorescently labeled linker oligonucleotides were added and allowed to hybridize in 6×SSPE with 0.1% Triton X-100 at room temperature for thirty minutes. This is a preferred protocol for attachment of linkers. The linker oligonucleotides were cy5-derivatized during synthesis, and were complementary in 25 base-pair segments to specific anchoring oligonucleotides. The sequences of the seven anchors and linkers were as follows (all shown 5' to 3'):

```
#1Anchor*:
TCCACGTGAGGACCGGACGGCGTCC                                  SEQ ID:1

Linker**
GTCGTTTCCATCTTTGCAGTCATAGGATACTGAGTGGACGCCGTCCGGTCCTCACGTG  SEQ ID:2
GA RNA mimic(mouse C-jun):
CTATGACTGCAAAGATGGAAACGACGATACTGAGTTGGACCTAACATTCGATCTCAT   SEQ ID:3
TCA Detector Oligonucleotide***
TGAATGAGATCGAATGTTAGGTCCA                                   SEQ ID:4

#2 Anchor*:
CACTACGGCTGAGCACGTGCGCTGC                                   SEQ ID:5

Linker**
CTAGGCTGAAGTGTGGCTGGAGTCTGCAGCGCACGTGCTCAGCCGTAGTG          SEQ ID:6

RNA mimic (mouse MIP-2):
AGACTCCAGCCACACTTCAGCCTAGGATACTGAGTCTGAACAAAGGCAAGGCTAACT   SEQ ID:7
GAC Detector Oligonucleotide***
GTCAGTTAGCCTTGCCTTTGTTCAG                                   SEQ ID:8

#3 Anchor*:
GTCAGTTAGCCTTGCCTTTGTTCAG                                   SEQ ID:9

Linker**
ACCATGTAGTTGAGGTCAATGAAGGGCGCTCCCACAACGCTCGACCGGCG          SEQ ID:10

RNA mimic (mouse GAPDH):
CCTTCATTGACCTCAACTACATGGTGATACTGAGTGGAGAAACCTGCCAAGTATGAT   SEQ ID:11
GAC Detector Oligonucleotide***
GTCATCATACTTGGCAGGTTTCTCC                                   SEQ ID:12

#4 Anchor*:
GAACCGCTCGCGTGTTCTACAGCCA                                   SEQ ID:13

Linker**
CTACCGAGCAAACTGGAAATGAAATTGGCTGTAGAACACGCGAGCGGTTC          SEQ ID:14

RNA mimic (mouse L32 protein):
ATTTCATTTCCAGTTTGCTCGGTAGGATACTGAGTGAGTCACCAATCCCAACGCCAGG  SEQ ID:15
CT Detector Oligonucleotide***
AGCCTGGCGTTGGGATTGGTGACTC                                   SEQ ID:16

#5 Anchor*:
CTCGTTCCGCGTCCGTGGCTGCCAG                                   SEQ ID:17

Linker**
CTGGCAGCCACGGACGCGGAACGAG                                   SEQ ID:18

#6 Anchor*:
CGGTCGGCATGGTACCACAGTCCGC                                   SEQ ID:19

Linker**
GCGGACTGTGGTACCATGCCGACCG                                   SEQ ID:20

#7 Anchor*:
GCGCGCCGCGTTATGCATCTCTTCG                                   SEQ ID:21

Linker**
CGAAGAGATGCATAACGCGGCGCCG                                   SEQ ID:22

*Anchors were synthesized with C12 spacer with amide at the 5' end
**Linkers were synthesized with Cy5 attached at the 5' end
***Detector Oligonucleotides were synthesized with biotin attached at
the 5' end
```

To each well either one linker or a mixture of linkers (as indicated in the figure) was added in bulk. (To the well marked "all" was added a mixture of all seven linkers.) Following incubation and washing in 5×SSP 3 times, the fluorescence picture shown on the right portion of the figure was taken with a Tundra imager (IRI, St. Catherines, Ontario). As can be seen, the linkers self-assembled to the surface, by specifically associating with their complementary anchors.

This process is repeated except that eight different anchors are dispersed in each well and linkers subsequently preferentially associated therewith. The entire process is repeated with 36, 64 etc. different anchors in each well of a 24, 96, 384, 864 or 1536 well plate.

Example 2

Figure 11:
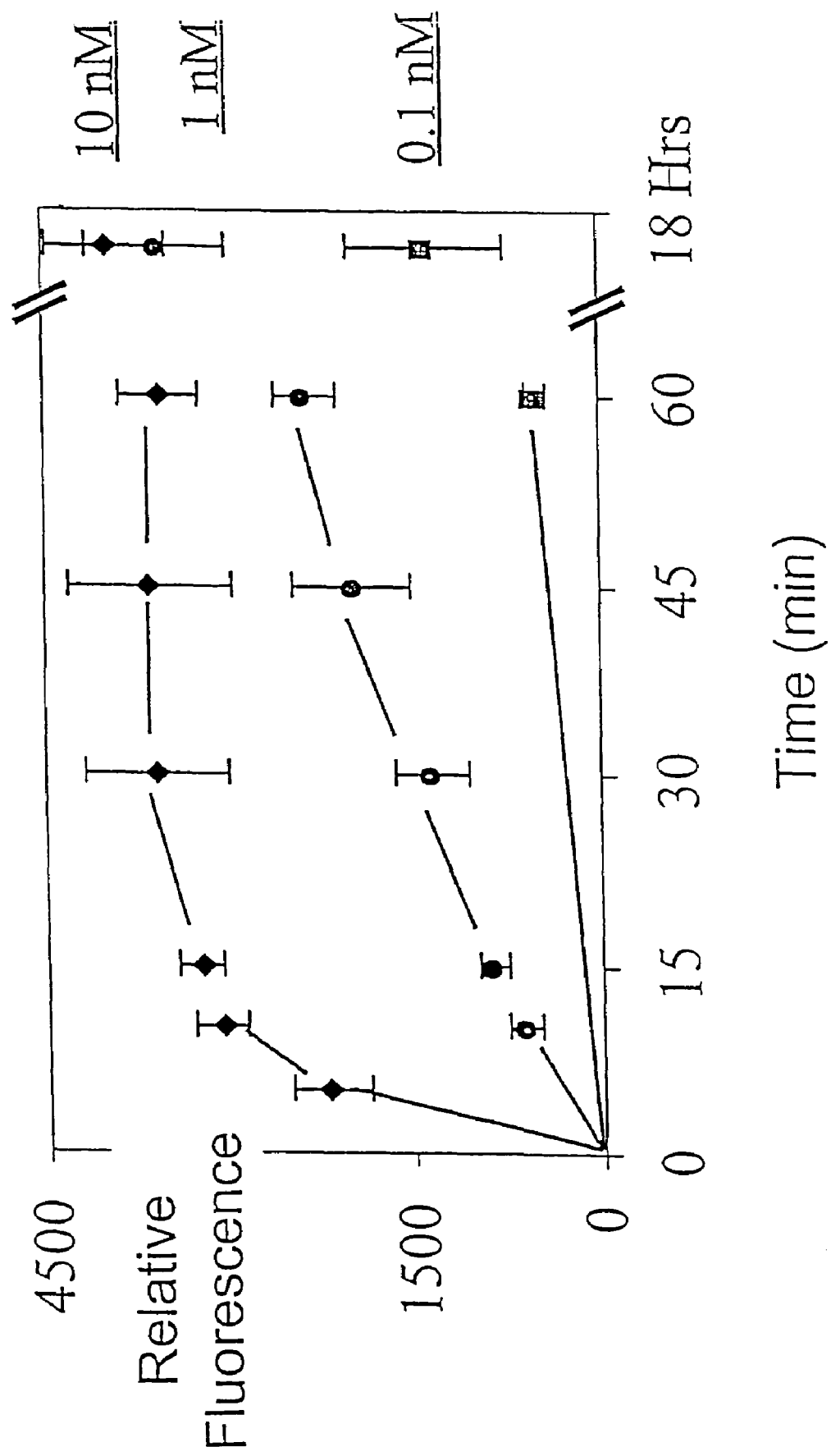
FIG. 11 illustrates binding kinetics of an anchor to a linker.

Binding Kinetics (see FIG. 11)

Figure 1:
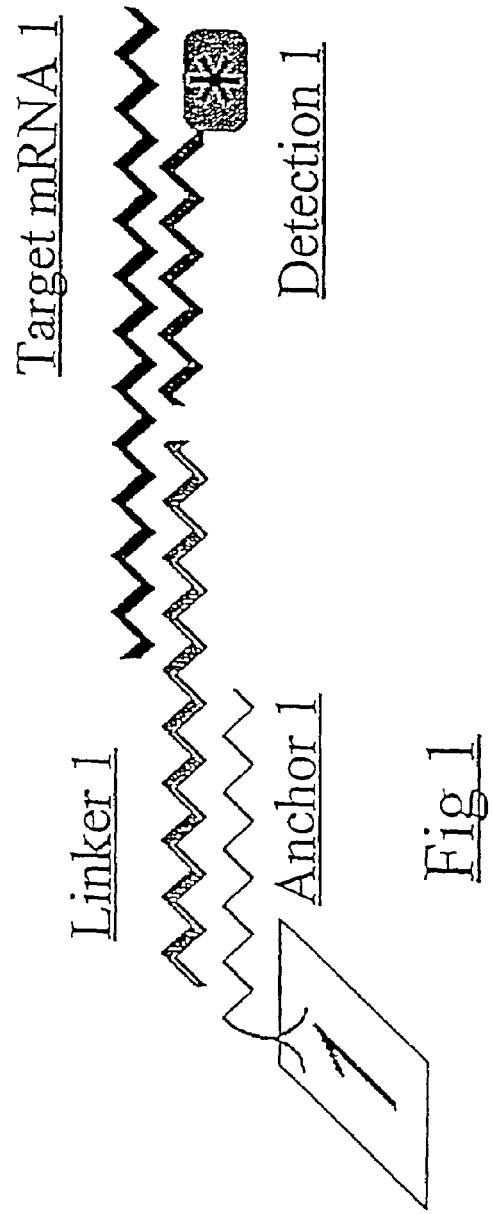
FIG. 1 illustrates a design scheme for oligonucleotides, in which a linker 1 contains a portion that is specific for anchor 1 and another portion (a probe) that is specific for target mRNA 1, and in which a labeled detection probe 1 is specific for a sequence of target mRNA 1 which is different from the sequence of the target-specific portion of the linker.
Figure 2:
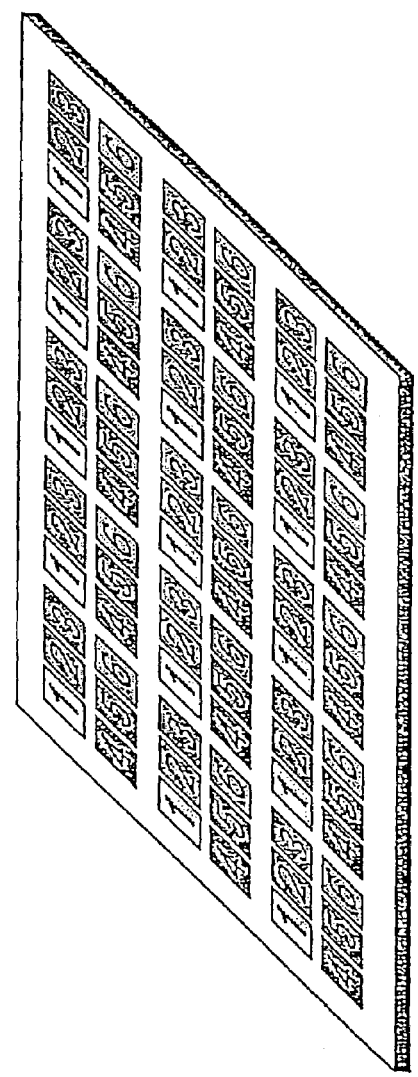
FIG. 2 illustrates a surface which comprises 15 test regions, each of which comprises an array of six anchor oligonucleotides.
Figure 3:
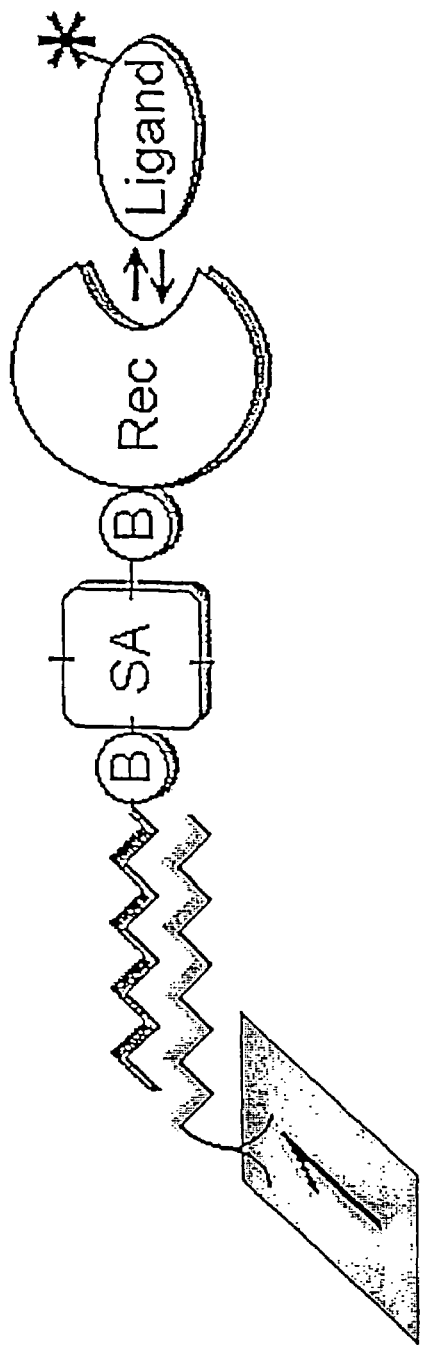
FIG. 3 illustrates the design of a linker for a receptor binding assay, in which the anchor-specific portion of the linker is associated with the probe portion (the receptor protein) via biotin and streptavidin molecules, and in which a ligand specific for the receptor is labeled with a fluorescent labeling molecule. B: Biotin. SA: Streptavidin. Rec: Receptor protein. Ligand: a natural or synthetic ligand for the receptor. *: a fluorescent labeling molecule attached to the Ligand.
Figure 4:
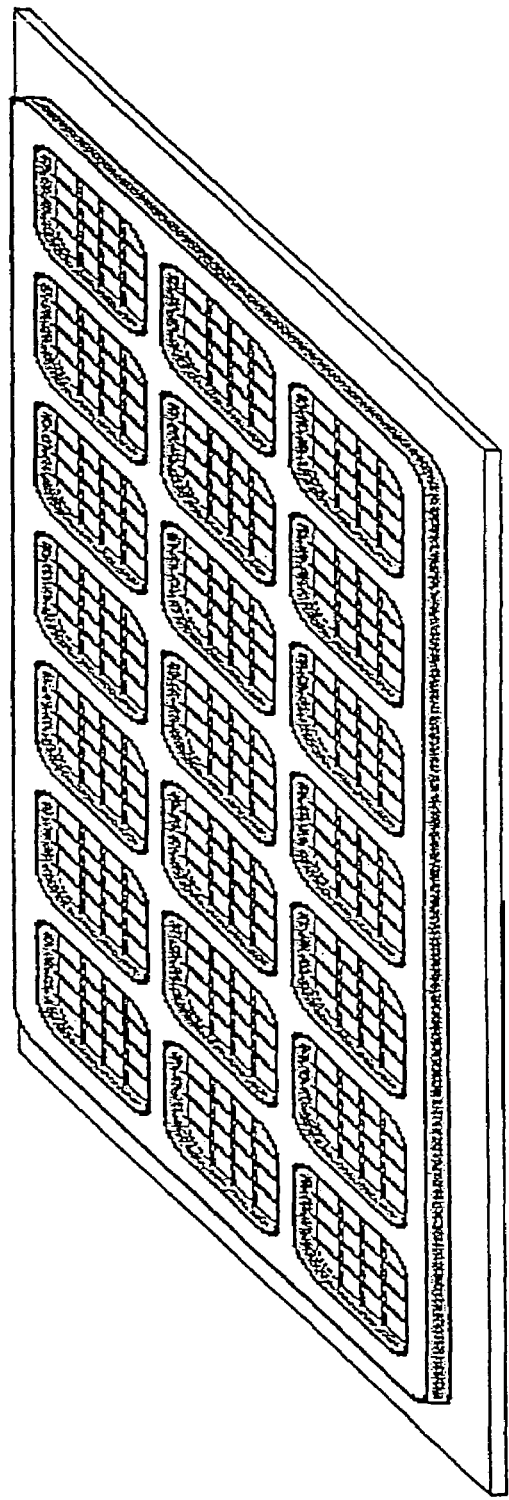
FIG. 4 illustrates a surface which comprises 21 test regions, each of which is further subdivided into 16 subregions (indentations, dimples).
Figure 5A:
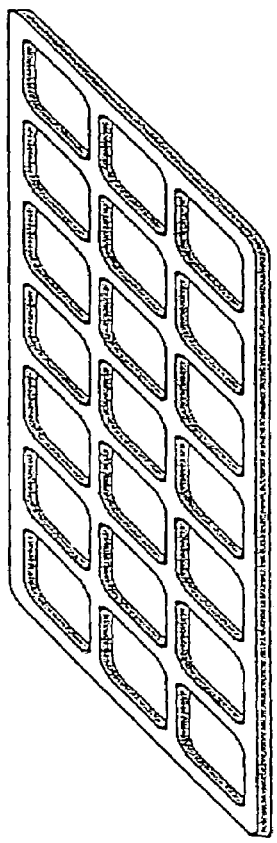
FIGS. 5*a*, 5*b* and 5*c* illustrate three pieces from which a surface such as that shown in FIG. 4 can be assembled.
Figure 5B:
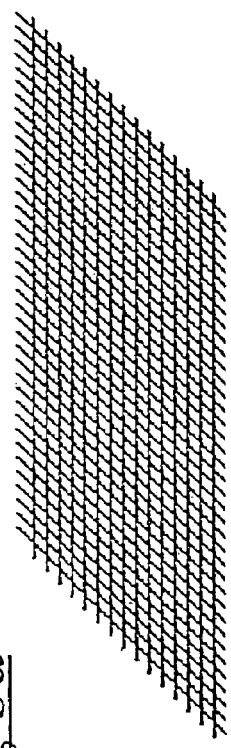
Figure 5C:
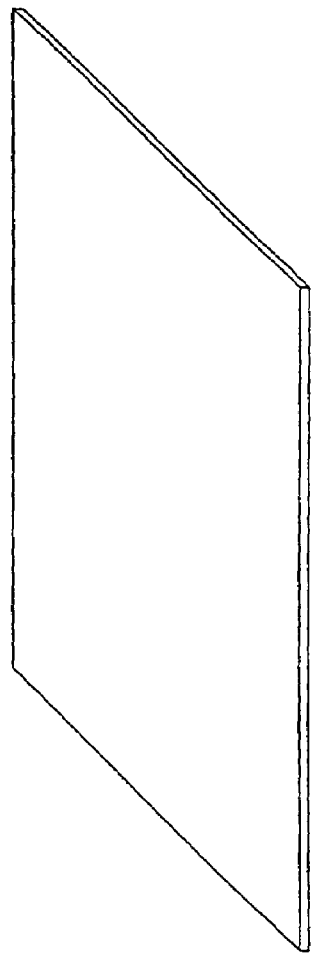
Figure 6:
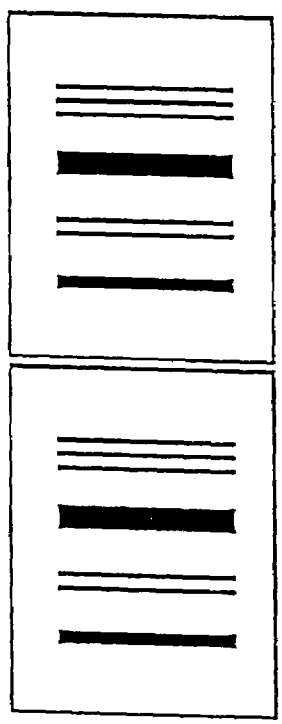
FIG. 6 represents two test regions, each of which comprises a linear array of probes (or anchors) which are in a "bar-code"-like formation.
Figure 7:
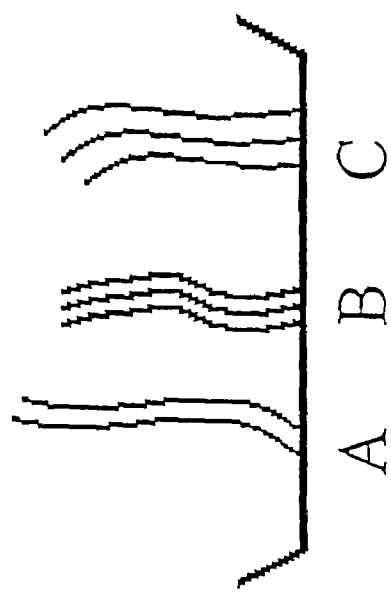
FIG. 7 schematically represents a test region comprising 3 anchors (A, B and C), each of which is present in multiple copies (a "group"). The location of each group of anchors is termed a "locus."
Figure 8:
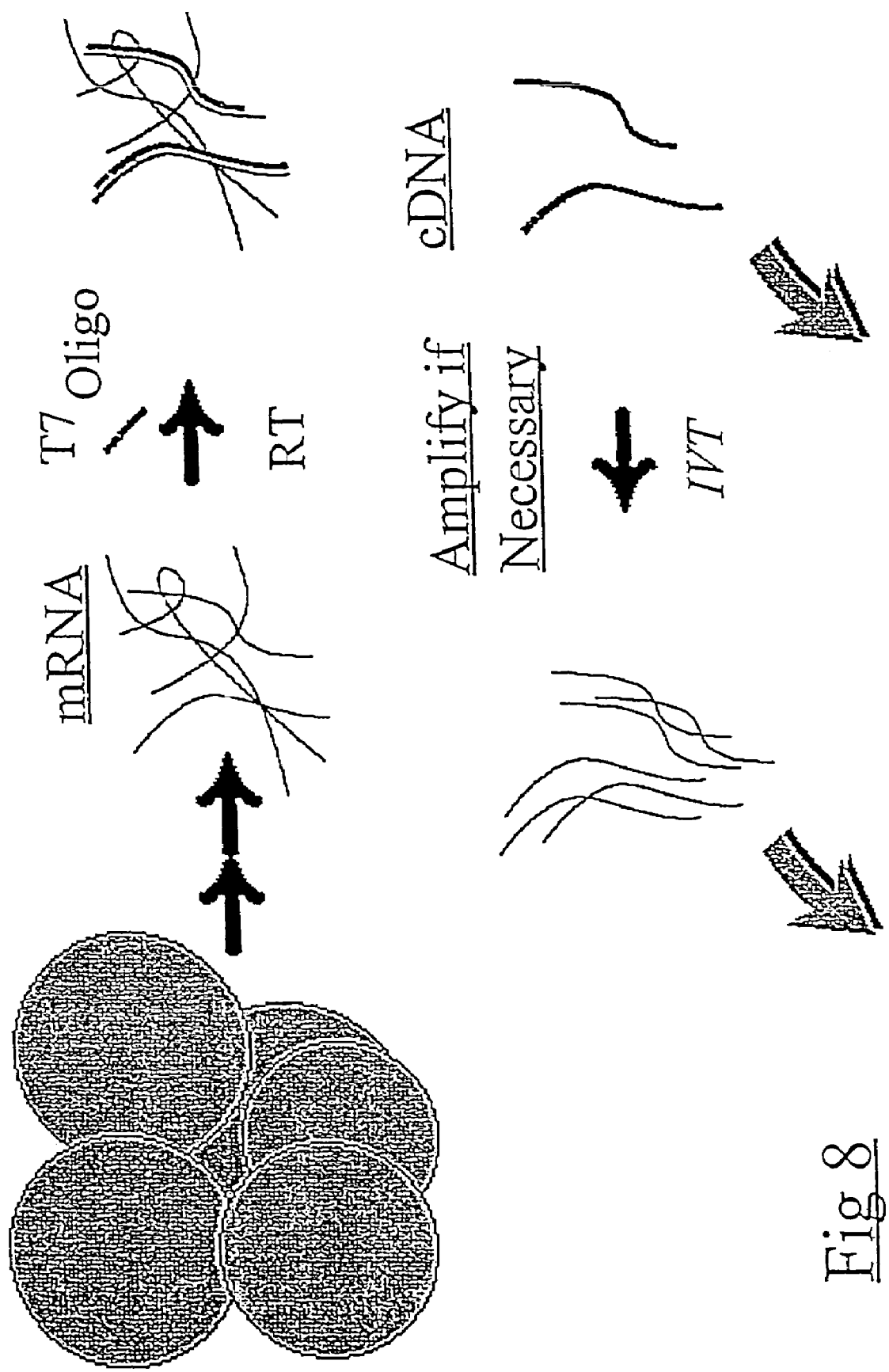
FIG. 8 illustrates an assay in which cDNA(s) generated by specific reverse transcriptase are assayed on MAPS plates.
Figure 9:
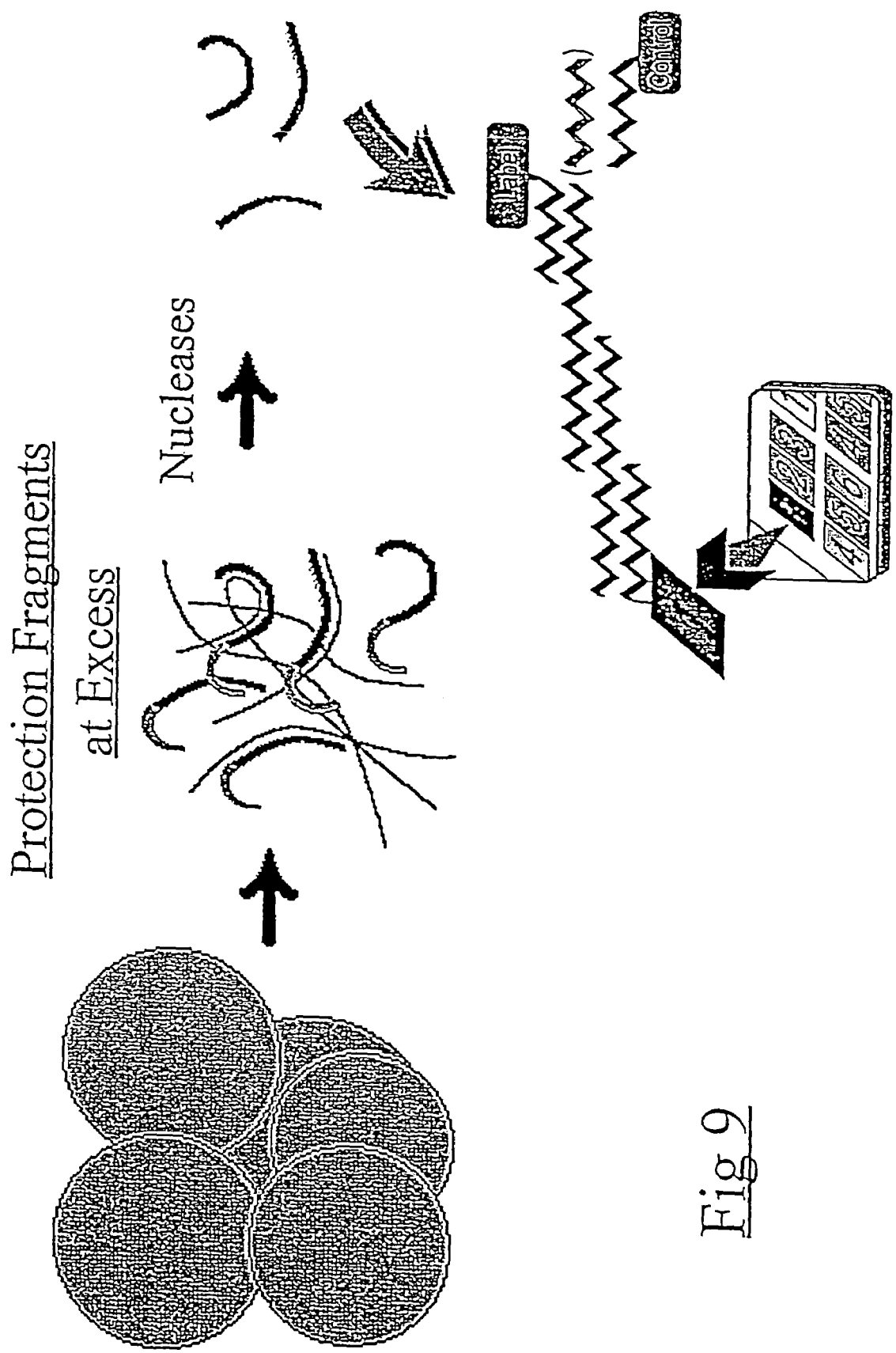
FIG. 9 illustrates an assay which uses a nuclease protection procedure (NPA-MAPS assay). Sample RNA is prepared from cells or from tissue and is represented as thin wavy lines. To the RNA sample is added a group of polynucleotide protection fragments, portrayed as thick, dark and light lines. The dark sections of the protection fragments represent segments that are complementary to specific RNA targets and hybridize to those targets. The light sections represent overhanging portions: sequences contiguous with the complementary sequence but not complementary to target. The protection fragments are added in excess. Following hybridization of all available target to the protection fragments, the samples are treated with an appropriate cocktail of nucleases and with chemical treatments that destroy unwanted non-hybridized RNA and non-hybridized polynucleotide. For example, S1 nuclease can destroy any single stranded DNA present. Hence, excess protection fragment is hydrolyzed as is the overhanging non-hybridized portion of bound protection fragment. RNA can be hydrolyzed by addition of ribonucleases including ribonuclease H and or by heating samples in base. Remaining is a collection of cleaved protection fragments that reflect how much of each target RNA had been present in the sample. The remaining protection fragments are measured by a MAPS hybridization assay.

The rate of hybridization of Cy5-derivatized linker number 1 to its complementary attached anchor is shown, for different concentrations of linker. The generic MAPS plate was prepared as for FIG. 1, except anchor 1 was attached at four spots per well. Incubations were done at room temperature in 5×SSP with 0.1% tween-20, wells were washed 3 times with 5×SSP, and bound fluorescence was measured. A fluorescence picture of the plate was taken with the Tundra, and background was subtracted and the integrated intensity of each spot within each well was calculated with Tundra software. Plotted is the average and standard deviation for the integrated intensity for the four spots within each of two duplicate wells.

Example 3

Fluorescent Linker

A generic MAPS plate is produced with one anchoring oligonucleotide spotted to either 1 spot per well (top two rows), 4 spots per well (next four rows) or 16 spots per well (lower two rows), according to the methods discussed above. To each well complementary, fluorescently labeled, linker is attached by the preferred protocol described in Example 1. Following washing the fluorescence picture of the plate is taken with the Tundra. The amount of fluorescence at each spot reports how much functional linker is available to hybridize to target. The amount of signal detected at repeated spots is highly reproducible.

Example 4

Binding Curves

To the plate prepared as described in Example 3, is added different concentrations of a target oligonucleotide. The linker that has been associated contains a 25-mer sequence complementary to a portion of the target. The target is added in 5×SSC with 0.05% SDS in a total volume of either 30 or 100 microliters, and the plate is covered and incubated at 50° C. overnight. Following hybridization of the target to the attached linker, the target is visualized by a preferred protocol using chemiluminescence. A biotinylated detector oligonucleotide, containing a 25-mer sequence complementary to a separate portion of the target (not to the same portion complementary to linker) is added at 30 nM. Biotinylated detector can be added for 30 minutes after washing away excess unattached target, or it can be added along with target for the length of the overnight hybridization. Following attachment of detector, the surface is washed twice with 5×SSC, once with 1×SSP containing 0.1% Tween-20 and 1% PEG (SSPTP), and a 1:50,000 dilution of 250 ug/ml Horse Radish Peroxidase conjugated to Streptavidin (HRP:SA, from Pierce, Rockford, Ill.) is added for 5 hours in SSPTP at room temperature. Wells are washed four times with SSPTP, and washed once and then incubated with Super Signal Ultra reagent (Pierce). After a few minutes, pictures of luminescence are collected with the Tundra imager, e.g., the picture can accumulate within the CCD array for five minutes. Low levels of target can be visualized in some wells at a target concentration of as little as ~$5 \times 10^{-13}$ M; the amount of signal generally becomes saturated at a target concentration of ~$10^{-10}$ M. The amount of signal detected at repeated spots is highly reproducible.

Example 5

Figure 12:
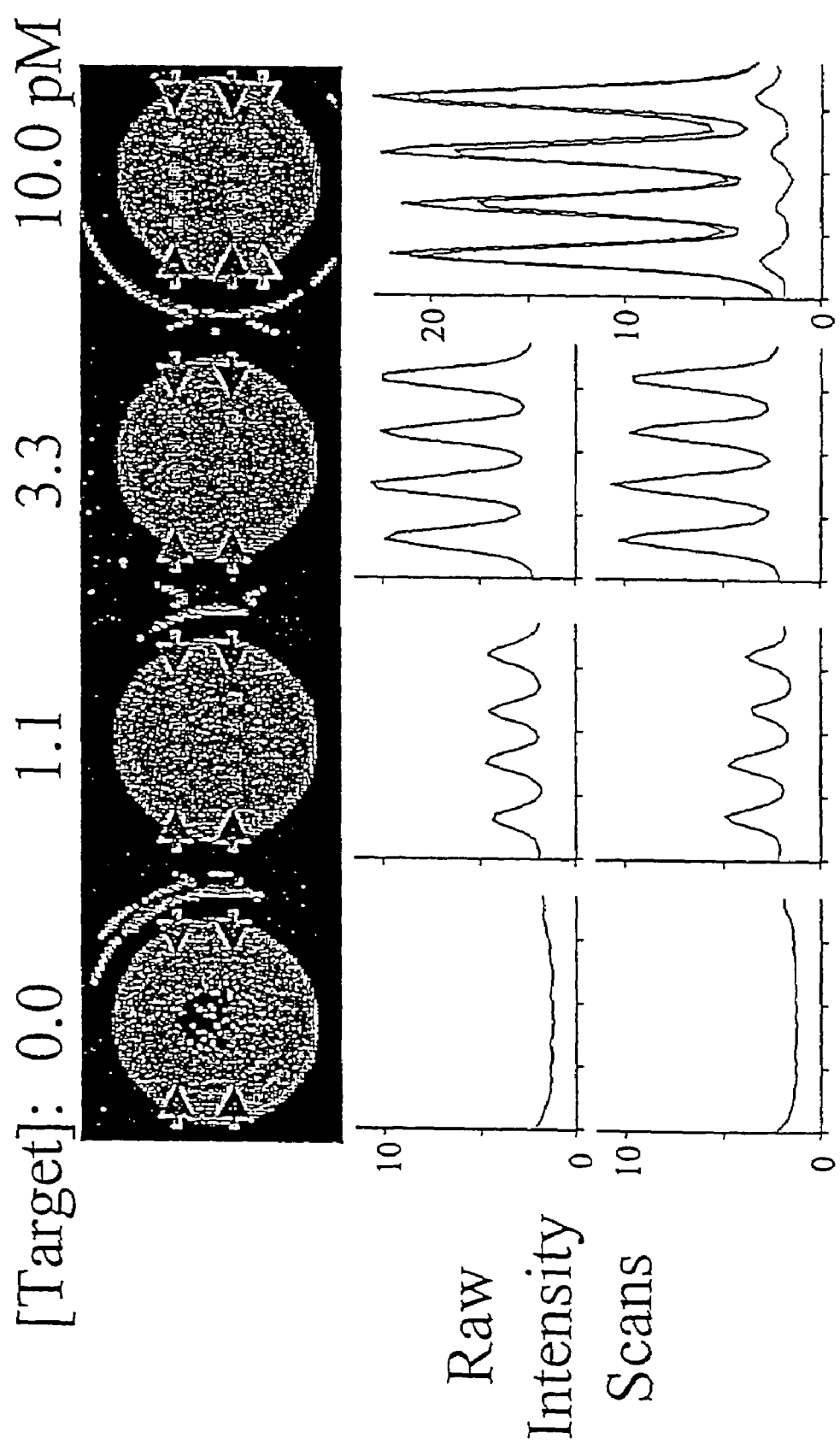
FIG. 12 illustrates a MAPS assay of two oligonucleotide targets.

Assay of Two Oligonucleotides (see FIG. 12)

A binding curve demonstrating a MAPS hybridization assay using the preferred protocol discussed above for two different target oligonucleotides is shown. A generic MAPS plate was prepared with four different anchoring oligonucleotides each spotted four times within each well. For the second and fourth anchor, complementary linker oligonucleotides were self-assembled onto the surface as described. Two targets were added at the concentrations shown in 40 microliters to each well as described, and incubated at 50° C. overnight. The amount of each target attached was visualized by attaching biotinylated detection oligonucleotide specific for each target followed by HRP:SA and chemiluminescence imagine as described. In the lower panel the intensity of the image is quantified. Software that is part of the Tundra Imager package was used to scan the intensity of the images along lines between the arrows shown in the upper panel. At the lowest concentration of target, 1.1 pM, the scanned images show well-defined gaussian peaks at each spot, while there are no discernable background peaks seen in the left-most sample, at 0 concentration of target.

Example 6

Figure 13:
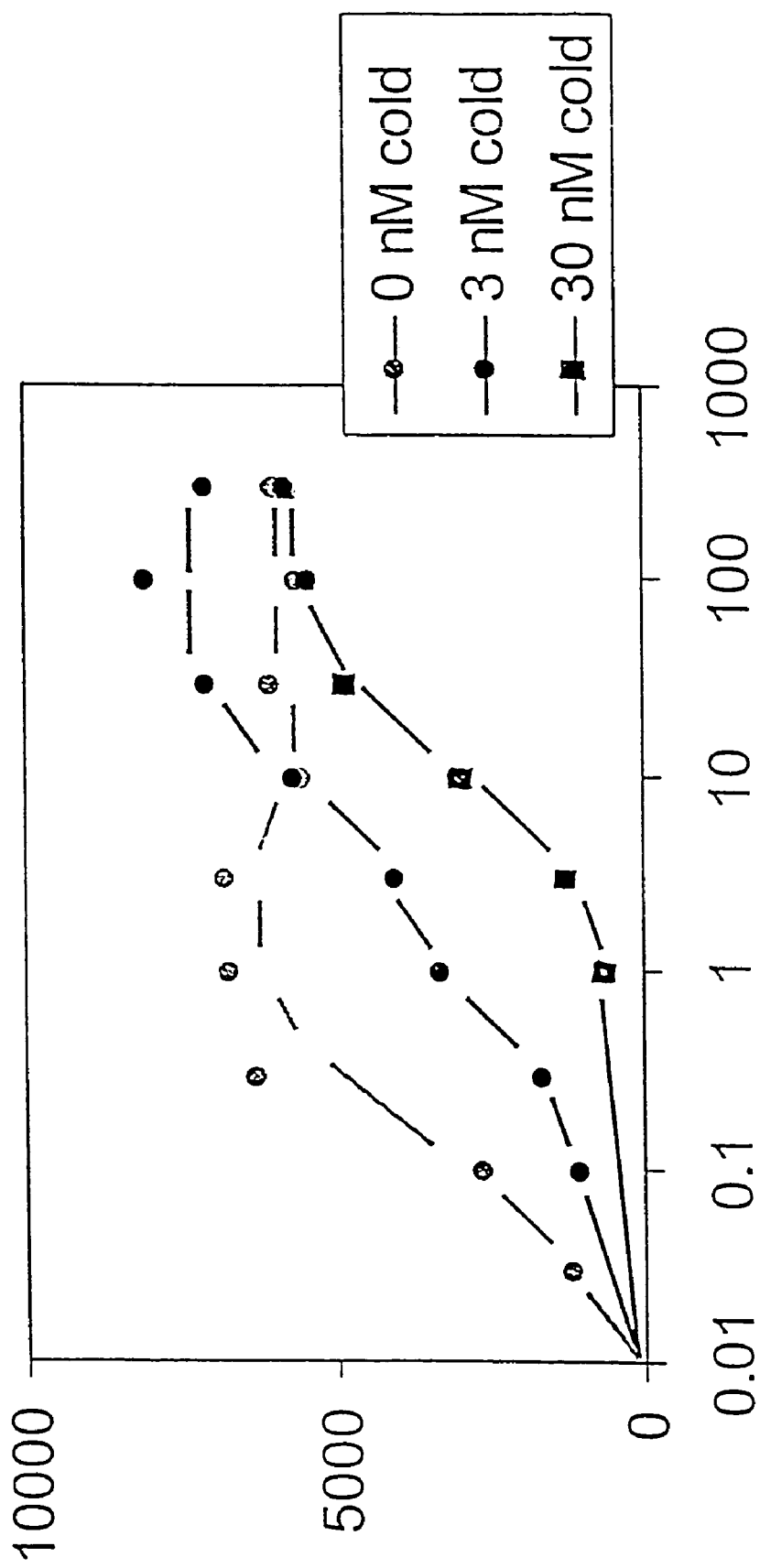
FIG. 13 illustrates the quantification of a sensitivity shift.

Sensitivity Shifting (see FIG. 13)

A MAPS hybridization assay can be used for measuring the concentration of a set of oligonucleotides, by binding them to a surface and labeling them. This works well for those oligonucleotides which are at modest or low concentration. Two samples can be distinguished in such a case because if one sample contains more oligonucleotide, more will bind. On the other hand, if the concentration of targeted oligonucleotide is saturating for the surface (i.e. if it is high enough to occupy all binding sites), then if the concentration goes up no more can bind, so the amount cannot be measured. However, the binding curve of a target can be shifted by adding unlabeled competing ligand.

Binding data are obtained for four different oligonucleotide targets, all of which saturate the surface (i.e. reach maximal binding) at roughly 3 nM. By adding unlabeled competitive targets to all wells, the binding of labeled oligonucleotide is shifted, so that less binds at the lower concentration, and the level at which saturation occurs is moved up. One can add competitive oligonucleotides for, say, targets 1 and 3 but not 2 and 4. This shifts the sensitivity of the assay only for targets 1 and 3. In this way oligonucleotide targets of widely different concentrations can be measured within one assay well, if the relative amount of oligonucleotide expected is known.

The data can be quantified as explained above for the binding of one of the oligonucleotide targets. FIG. 13 shows quantitatively that including competitive oligonucleotide in the assay shifts the binding curve used to assay for this target to higher concentrations.

Example 7

Figure 14:
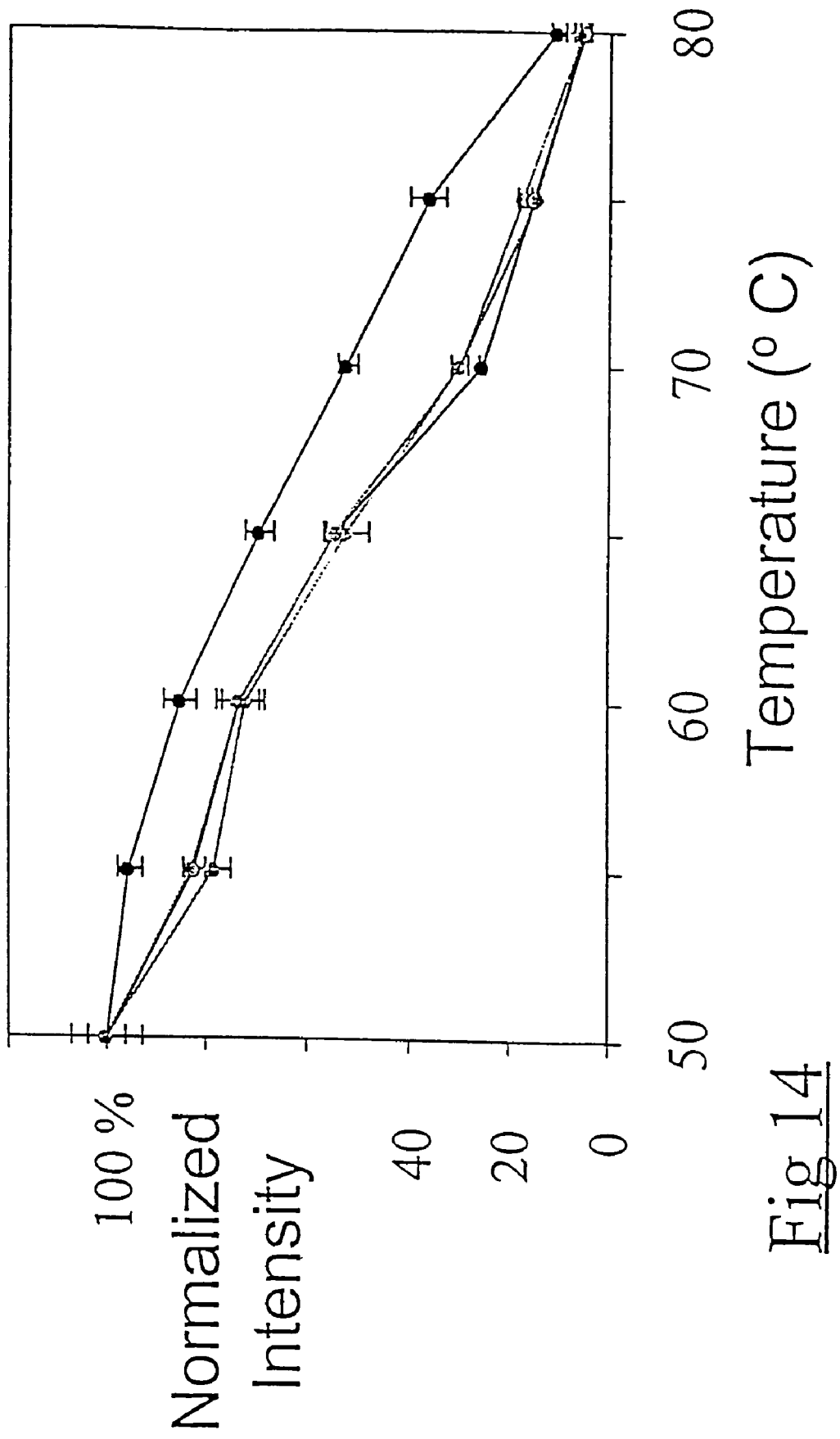
FIG. 14 illustrates melting temperature determinations for four oligonucleotide linker/anchor combinations.

Melting Temperature of Four Probes (see FIG. 14)

The amount of four different fluorescent labeled linker oligonucleotides specifically hybridized to anchor oligonucleotides by the MAPS assay is plotted as the temperature is raised. The four oligonucleotides were first allowed to hybridize at 50° C. for 1 hour at 300 nM. Then the wells were washed with SSC without probes, and the amount bound was measured as above by fluorescence (50° C. point). Then the surface was incubated at 55° C. for 30 minutes and the fluorescence bound measured, and so on for all temperatures presented.

Example 8

Detection Methods

Two detection methods can be compared directly. To a MAPS plate with four oligonucleotide anchors attached, each at four spots per well, are added two oligonucleotides to each well, with both including a covalently attached cy5 moiety or both containing a biotin group. The epi-fluorescence measurement is performed as described for viewing and measurement of the fluorescent linker. The chemiluminescence measurements are performed as described for the MAPS assay using subsequent addition of HRP:SA and a chemiluminescence substrate. The signals generated are roughly of the same magnitude. However, for the geometry of the microplates, which contain walls separating each well, and occasional bubbles of liquid or a miniscus of fluid, reflections in the epi-fluorescence images can cause interference in data interpretation.

Example 9

Chemiluminescence Products

Two products available as chemiluminescence substrates for horse radish peroxidase can be compared as detection procedures for the MAPS assay. A MAPS plate is prepared as for Example 8, and incubated with biotinylated linker oligonucleotides. Then either alkaline phosphatase coupled to streptavidin (AlkPhos:SA) or HRP:SA is added, followed by washing and addition of either CDP-Star (Tropix) to the wells with AlkPhos:SA or ECL-Plus to the wells with HRP:SA. Labeling with SA derivatized enzymes and substrates is as suggested by the manufacturers for use in labeling of western blots. These two (as well as other available substrates) can both be used to assess oligonucleotide hybridization to MAPS plates.

Example 10

Resolution at 0.6 mm

The resolution of the current system for MAPS assay is tested by preparing a MAPS plate with four different oligonucleotide anchors per well each spotted four times per well, with a pitch (center-to-center spacing) of 0.6 mm. Then either cy5-derivatized linkers or biotinylated linkers are hybridized and detected and scanned as above. For the epi-fluorescence measurement the resolution is higher (and pitch could likely be reduced). For the chemiluminescence detection procedure neighboring spots are not completely separated, yet at this spacing individual peaks may be resolved unambiguously by computer deconvolution.

Example 11

Test Nuclease Protection Protocol

In an assay to test for the optimal conditions for hybridization and nuclease treatment for the nuclease protection protocol, the Nuclease Protection Assay kit from Ambion (Austin, Tex.) is used to provide conditions, buffers and enzymes. Eight samples are prepared in one of three buffers. Hyb Buff 1 is 100% Hybridization Buffer (Ambion); Hyb Buff 2 is 75% Hybridization Buffer and 25% Hybridization Dilution Buffer (Ambion); and Hyb Buff 3 is 50% of each. A 70-mer oligonucleotide that contains 60 residues complementary to a test mRNA is synthesized (Biosource International, Camarillo, Calif.) and labeled with Psoralen-fluorescein (Schleicher and Schuell, Keene, N.H.) following the protocol as suggested for labeling of Psoralen-biotin by Ambion. Briefly, protection fragment is diluted to 50 ug/ml in 20 μls of TE buffer(10 mM Tris, 1 mM EDTA, pH 8) boiled for 10 minutes, and rapidly cooled in ice water. Four μls of 130 ug/ml Psoralen-fluorescein in DMF is added, and the sample is illuminated for 45 minutes at 40° C. with a hand-held long wavelength UV source. Free Psoralen-fluorescein is removed by extraction with saturated butanol. The mRNA used is GAPDH antisense mRNA, prepared from antisense plasmid (pTRI-GAPDH-Mouse antisense Control Template from Ambion) using T7 promoter and the MaxiScript kit (Ambion). The short protection fragment is the 60-mer complementary portion synthesized separately and similarly labeled. The sequences of the protection fragments are as follows:

```
Full length protection fragment:
CGAGAAATATGACAACTCACTCAAGATTGTCAGCAATGCATCCTGCACCACCAACTGCTTGCT    SEQ ID:23

TGTCTAA

Short protection fragment:
CGAGAAATATGACAACTCACTCAAGATTGTCAGCAATGCATCCTGCACCACCAACTGCTT      SEQ ID:24
```

Hybridizations are done by mixing protection fragments at 20 nM and GAPDH mRNA at 60 nM in 10 μls final volume for two hours at 22° C. or 37° C. Following hybridization, 200 μls of a mixture of nucleases is added according to instructions from the manufacturer (Ambion Nuclease Protection Kit, 1:200 dilution of nuclease mixture) and incubated again at the same temperatures for 30 minutes. Hydrolysis is stopped with Hybridization Inhibition Buffer (Ambion), and oligonucleotides are pelleted and washed with Ethanol. 10 μls of 1× Gel Loading Buffer (Ambion) is added and oligonucleotides are separated on a 15% TBE-urea gel. The gel is swirled in running buffer for 30 minutes, put on a plastic plate and imaged with the Tundra using fluorescein filters for selecting excitation and emission wavelengths. The image is accumulated on the CCD array for 2 minutes. Best conditions are those for samples incubated in Hyb Buff 2 at 37° C. or in Hyb Buff 3 at 22° C. In these samples no detectable full-length protection fragment remains, and significant amounts of a portion of the full-length protection fragment at a size apparently the same as the short protection fragment are seen.

alone would be detected by MAPS. In the lower portion of the figure, the intensity scan (as analyzed by the imager) for the top row of wells is presented. The amount of GAPDH mRNA present in the sample (that is, the amount in each duplicate well after aliquoting to the MAPS plate) is listed in the figure.

The Oligonucleotides Used for the MAPS Plates Were as Follows:

```
Anchor*:
CGCCGGTCGAGCGTTGTGGGAGCGC                                           SEQ ID:25

Linker**
CTTGAGTGAGTTGTCATATTTCTCGGATACTGAGTGCGCTCCCACAACGCTCGACCGG  SEQ ID:26
CG Protection fragment (complementary to mouse antisense mRNA for GAPDH)
CGAGAAATATGACAACTCACTCAAGATTGTCAGCAATGCATCCTGCACCACCAACTG   SEQ ID:27
CTTGCTTGTCTAA Detector Oligonucleotide***-labeled at 5' end with biotin
AAGCAGTTGGTGGTGCAGGATGCAT                                           SEQ ID:28

*Anchors were synthesized with C12 spacer with amide at the 5' end
**Linkers were synthesized with Cy5 attached at the 5' end
***Detector Oligonucleotides were synthesized with biotin attached at
the 5' end
```

Example 12 mRNA Assay by NPA-MAPS. (see FIG. 15)

The full NPA-MAPS protocol was used, with conditions for hybridization and nuclease treatment similar to those described in Example 11. Ten samples were run for the assay. All contained the same amount of the 70-mer oligonucleotide protection fragment and different amounts of GAPDH mRNA. Hybridization samples in 10 μls in 50% Hybridization Buffer and 50% Dilution Buffer containing 0.08 mg/ml Yeast RNA (Ambion) were heated to 90° C. for 6 minutes, briefly centrifuged, heated to 70° C. for 5 minutes, and allowed to cool to 19° C. and incubated for 19 hours. 200 μls of nuclease mixture was then added to each sample for 30 minutes at 19° C. 60 μls was aliquoted from each sample for the MAPS assay. 2 μl of 10 N NaOH and 2 μl of 0.5 M EDTA was added, and the sample heated to 90° C. for 15 minutes, 37° C. for 15 minutes, and allowed to sit at room temperature for 20 minutes. Then samples were neutralized with 2 μl of 10 M HCl, and 12 μls of 20×SSC containing 2 M HEPES pH 7.5 and 200 nM biotinylated detector oligonucleotide specific for the protection fragment was added along with 1 μl of 10% SDS. Samples were mixed, heated to 80° C. for 5 minutes, and two 35 μl aliquots of each sample were pipetted to two wells of a MAPS plate (each sample was split in two and run in duplicate on the MAPS plate). The plate had been prepared as for standard MAPS protocol, with self-assembled CY5-derivatized linker specific for the protection fragment already attached. The MAPS plate was covered and incubated at 50° C. overnight, and detection and luminescence performed as described. In the last sample, no nucleases were added during the assay as a control to visualize how the protection fragment

Example 13

Figure 16:
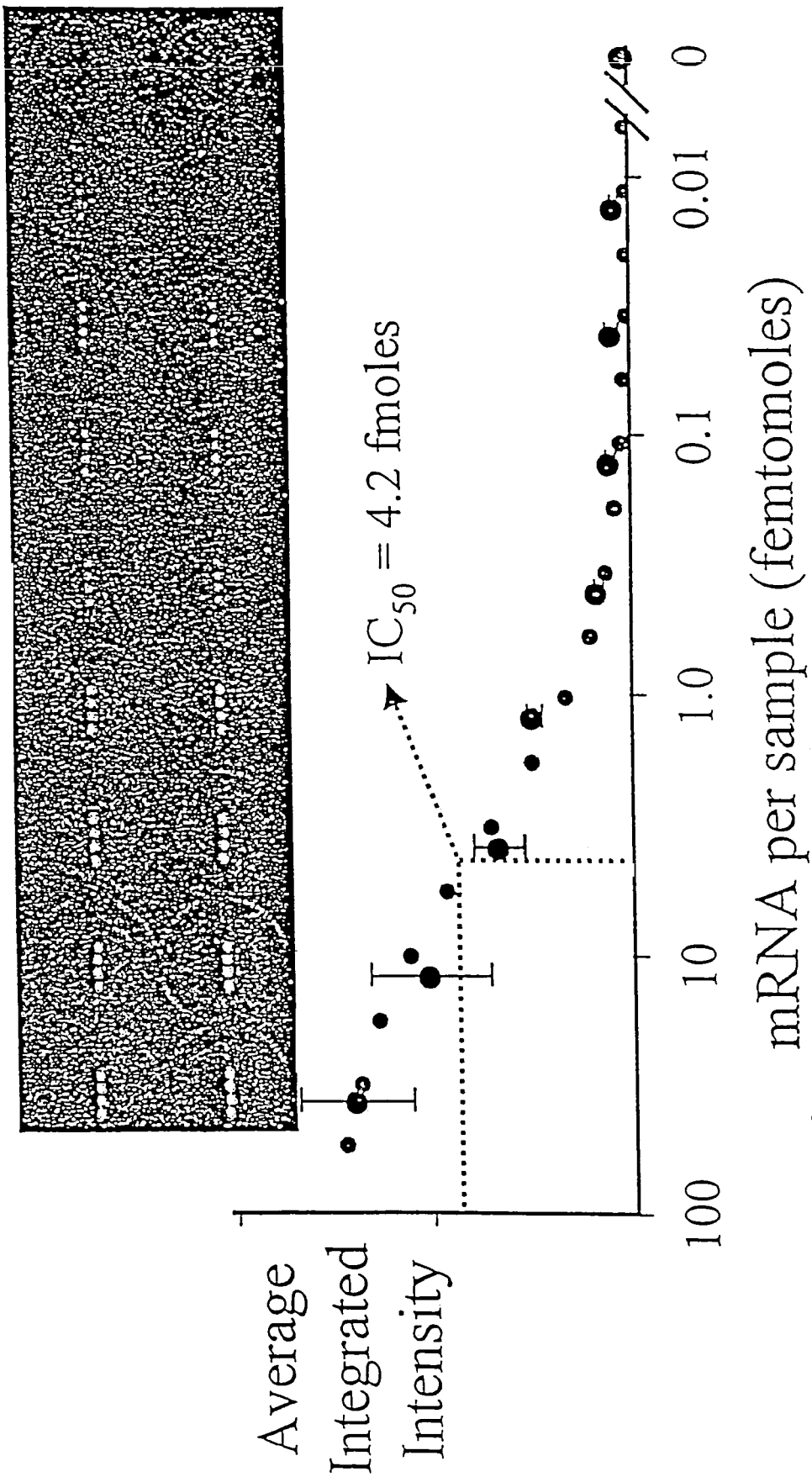
FIG. 16 illustrates a dilution curve with NPA-MAPS.

Dilution Curve, NPA-MAPS (see FIG. 16)

Figure 15:
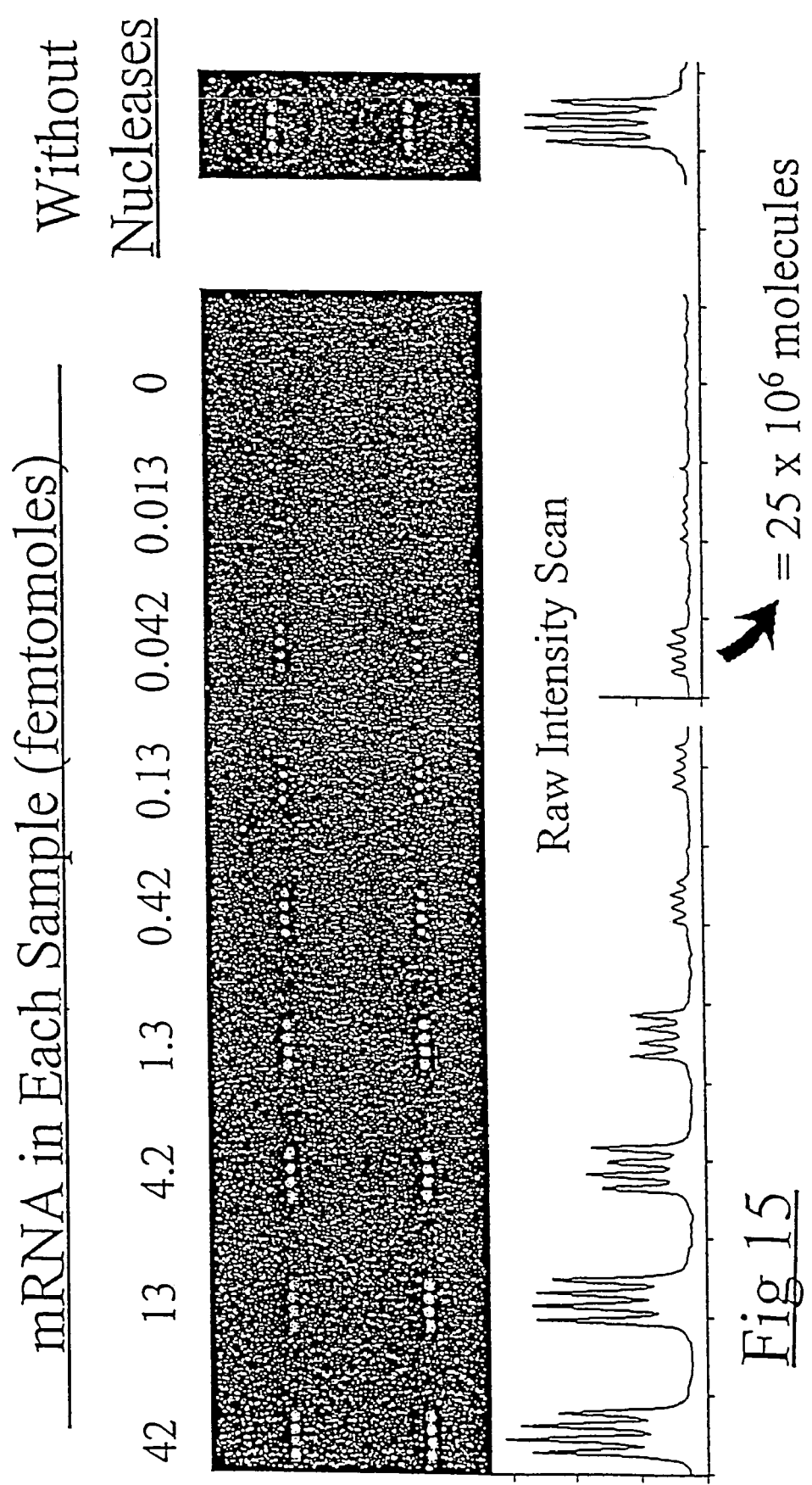
FIG. 15 illustrates an mRNA assay by NPA-MAPS.

The data discussed in Example 12 and shown in FIG. 15 were quantified and plotted as a dilution curve. The average and standard deviations for all eight spots of the two duplicate wells are plotted for each concentration of mRNA. A binding curve is superimposed, of the form:

$$\text{Fraction Bound} = \text{Max Bound} * 1/(1 + IC_{50}/L)$$

where Max Bound is the maximum bound at saturation, Fraction Bound is the amount bound at ligand concentration, L, and the $IC_{50}$ is the concentration of ligand at which the Fraction Bound is half of Max Bound. The curve is shown as red dots on the figure, drawn with a best fit value of $IC_{50}$=4.2 femtomoles as labeled in the figure.

Example 14

NPA-1-MAPS Assay of GAPDH mRNA in a Total Mouse Liver RNA Extract

A total mouse RNA extract is assayed for GAPDH mRNA with an NPA-MAPS assay and a dilution curve is made. Total RNA from mouse liver is prepared using a Qiagen kit. RNA is precipitated in 70% EtOH with 0.5 M Mg-Acetate, and resuspended in 10 μls of 5×SSC with 0.05% SDS with 1.8 nM protection fragment. The protection fragment added is an oligonucleotide 70 bases long, 60 bases of which are complementary to mouse GAPDH. Either a fragment complementary to mouse GAPDH mRNA is used ("protection fragment"), or the complement of the sequence is used as a negative control ("antisense fragment").

RNA samples with protection fragments are heated to 90° C. for 5 minutes, and hybridizations are done by bringing samples to 70° C. and allowing them to cool slowly to room temperature over night. S1 nuclease (Promega) at 1:10 dilution is added in 30 μls of 1×S1 Nuclease Buffer (Promega) for 30 minutes at 19° C., and stopped by 1.6 µls of 10 N NaOH and 2.7 µls of 0.5 M EDTA. Samples are heated to 90° C. for 15 minutes and then 37° C. for 15 minutes to denature and destroy RNA, neutralized with 1.6 µls of 10 M HCl, and incubated on MAPS plates overnight in 5×SSC with 0.05% SDS supplemented with 200 mM HEPES pH 7.5 to which 30 nM biotinylated detection oligonucleotide is added. Washing and visualization with SA-HRP is done as described. The amount of signal decreases in parallel with decreasing amounts of mouse RNA (samples include 500, 170, 50, 5, or 0.5 µg of total mouse RNA. Two control samples are included to which no S1 nuclease is added. Signal is seen only for the complementary protection fragment.

Oligonucleotides used:

For Antisense Control (same oligonucleotides as for example 12):

```
Anchor*:
CGCCGGTCGAGCGTTGTGGGAGCGC                                  SEQ ID:25

Linker**
CTTGAGTGAGTTGTCATATTTCTCGGATACTGAGTGCGCTCCCACAACGCTCGACCGG SEQ ID:26

CG

Protection fragment (complementary to mouse antisense mRNA for GAPDH)
CGAGAAATATGACAACTCACTCAAGATTGTCAGCAATGCATCCTGCACCACCAACTG  SEQ ID:27

CTTGCTTGTCTAA

Detector Oligonucleotide***
AAGCAGTTGGTGGTGCAGGATGCAT                                  SEQ ID:28

For Sense GAPDH mRNA samples:
Anchor*:
CGCCGGTCGAGCGTTGTGGGAGCGC                                  SEQ ID:25

Linker**
ATGCATCCTGCACCACCAACTGCTTGATACTGAGTGCGCTCCCACAACGCTCGACCG  SEQ ID:29

GCG

Protection fragment (complementary to mouse mRNA for GAPDH):
AAGCAGTTGGTGGTGCAGGATGCATTGCTGACAATCTTGAGTGAGTTGTCATATTTCT SEQ ID:30

CGGCTTGTCTAA

Detector Oligonucleotide***
CGAGAAATATGACAACTCACTCAAG                                  SEQ ID:31

*Anchors were synthesized with C12 spacer with amide at the 5' end
**Linkers were synthesized with Cy5 attached at the 5' end
***Probes were synthesized with biotin attached at the 5' end
```

Example 15

A Nuclease Protection MAPS Assay with Controls mRNA is extracted from mouse liver and nuclease protection is performed essentially as described in Example 14, except that the GADPH specific protection fragment comprises 60 nucleotides which are complementary to mouse GAPDH, followed by 15 "overhanging" nucleotides at the 3' end of the fragment which are not complementary to the target. After hybridization and nuclease digestion the remaining protection fragment is hybridized to a MAPS plate as indicated in Example 14, except that two different oligonucleotide detection fragments are used to detect the immobilized protection fragment. One detection fragment is complementary to the GAPDH-specific portion of the protection fragment, and the other, a control, is complementary to the 15 base overhang portion of the protection fragment. Each detection fragment is used on different replicate samples (i.e., in different wells), so that both detection fragments can be labeled with the same detection molecule. In the present example both fragments are labeled with HRP. Without the addition of nuclease, signals from both of the detection fragments are seen; whereas, when nuclease digestion is performed only the signal corresponding to the GAPDH sequences can be detected. The amount of GAPDH-specific signal is reduced relative to that observed in the absence of nuclease digestion, because the protection fragment is added at excess relative to the amount of GAPDH mRNA present. This allows the amount of GAPDH mRNA to be limiting to the protective hybridization, so that the amount of double-stranded hybrid formed (and therefore the amount of protection fragment that is protected from the nuclease) reflects the amount of mRNA. When no mRNA is included in the reaction mixture, neither signal can be detected when nucleases are added. The above findings demonstrate that the hybridization and digestion steps of the assay occurred as desired.

When protection fragments corresponding to a variety of targets are included in a given assay, each of the protection fragments can comprise the same 15 base overhang portion. This allows for one detection fragment to be used to test for remaining overhang for all samples.

Example 16

A Transcription Assay Screening for Compounds that May Alter the Expression of Genes that are Correlative with a Disease State.

A cell line derived from a human tumor is used. It is found to express 30 genes at higher levels than do normal cells.

(That is, these 30 genes are being used more than in normal cells, to make mRNA and then to make the protein for which the genes are the instructions. A transcription assay measures how much the genes are being used by measuring how much mRNA for each gene is present.) Using a nuclease protection assay on MAPS plates (NPA-MAPS), 8800 chemical compounds are tested to see if growing the cells in the presence of the compounds can reduce the expression of some of the 30 correlative genes without affecting the expression of six normal (constitutive, "housekeeping") genes. Any compounds having that effect might be useful in the future development of drugs for treating this kind of tumor.

About 10,000 to 100,000 cells are added to each well of 100 96-well polystyrene plates and the cells are grown for 2 days until they cover the surface of each well. For 8 wells of each plate, the cells are left to grow without additions. To the remaining 88 wells of each plate, a different chemical compound is added so that the effect of it alone can be tested. For the 100 plates used at one time, 8800 compounds can be tested or screened. The cells are grown for 24 hours in the presence of the compounds, and then the cells are harvested for assay. The cells in each plate are treated according to the instructions for preparing RNA in samples from 96-well plates (for example according to the Qiagen RNeasy 96 kit). After the RNA is prepared, the amount of each of 36 different mRNA species is quantified by the NPA-MAPS approach, including the 30 correlative genes and 6 normal "housekeeping" genes. 36 DNA oligonucleotide protection fragments, each corresponding to one of the genes of interest, are added to each well and allowed to hybridize under selected stringent conditions to their target mRNA sequences. Then S1 nuclease is added to destroy excess unhybridized DNA, and the samples are treated chemically to destroy the RNA as well. Left is the oligonucleotide protection fragment for each of the 36 genes in proportion to how much mRNA had been present in the treated cells for each sample.

One hundred 96-well plates, each of which comprises an array of a plurality of 36 different anchor oligonucleotides in each well, are prepared by adding to each well 36 different linker oligonucleotides. The linkers self-assemble on the surface of each well, converting the generic plates to MAPS plates comprising specific probes for each of the 36 oligonucleotide protection fragments. Each linker has a portion specific for one of the 36 anchors and a portion specific for a segment of one of the 36 protection oligonucleotides. The oligonucleotide sample from each well of the 100 sample plates is added to a corresponding well of the 100 MAPS plates. After hybridization under selected stringent conditions, a detection oligonucleotide for each target with a chemiluminescent enzyme attached is added, so that each specific spot of each well lights up in proportion to how much mRNA had been present in the sample. Any wells that show reduced amounts of correlative genes with no effect on the 6 house keeping genes are interesting. The compounds added to the cells for those samples are possible starting points to develop anti-tumor agents.

Example 17

Induced and Constitutive Gene Expression

RNA was prepared essentially as described in Example 14, from the livers of mice either not infected ("Control") or one hour after infection ("Infected") by adenovirus. 60 μgs of liver RNA was used for each sample, and samples were prepared in duplicate. Each assay well contained three sets of duplicate loci, corresponding to the three genes described above. Each locus contained an anchor, bound to a linker comprising a probe which was complementary to a protection fragment corresponding to one of the three genes. A nuclease protection MAPS assay was performed essentially as described in FIG. 12, and the images were collected and scanned as described. Shown are the raw image data collected and the intensity scans for duplicate wells for each of the three mRNA targets. The numbers over the scan lines are the integrated intensity values and standard deviations for each condition (n=4). The house-keeping gene, GAPDH, not expected to change, showed a modest increase of 1.3-fold in the infected sample that was not statistically significant. The transcription of MIP-2 and c-jun was increased 4 and 6-fold, respectively. These findings demonstrate that two genes, MIP-2 and c-jun, exhibit enhanced expression in response to adenovirus infection, compared to a control, constitutively expressed gene—GAPDH.

Example 18

An Enzyme Assay Screening for Compounds that Selectively Inhibit Tyrosine or Serine Kinases (see FIG. 17)

Kinases are enzymes that attach a phosphate to proteins. Many have been shown to stimulate normal and neoplastic cell growth. Hence, compounds that inhibit specific kinases (but not all kinases) can be used to test whether the kinases are involved in pathology and, if so, to serve as starting points for pharmaceutical development. For example, five tyrosine kinases that are involved in stimulating cell growth or in regulating the inflammatory response are src, lck, fyn, Zap70, and yes. Each kinase has substrates that are partially identified, as short peptides that contain a tyrosine. Some of the kinase specificities overlap so that different kinases may phosphorylate some peptides equally but others preferentially. For the five kinases, 36 peptide substrates are selected that show a spectrum of specific and overlapping specificities.

One hundred 96-well plates are used; each well comprises 36 generic oligonucleotide anchors. 36 linkers are prepared to convert the generic oligonucleotide array (with anchors only) to arrays comprising peptide substrates. The 36 peptide substrates are synthesized and each is attached covalently through an amide bond, for example, to an oligonucleotide containing a 5' amino group. The oligonucleotides contain sequences that hybridize specifically to the anchors. The peptide/oligo linkers are self assembled on the surface by adding them to all wells of the MAPS plates.

For screening, the five kinases at appropriate concentrations (so that the rates of phosphorylation of the substrates are balanced as much as possible) are added to each well along with one of 8800 different compounds to be tested. The compounds are tested for their ability to directly inhibit the isolated enzymes. The amount of phosphorylation of each arrayed peptide is detected by adding labeled antibodies that bind only to peptides that are phosphorylated on tyrosine. Any wells that show a reduction in some of the phosphotyrosine spots but not all of the spots are interesting. Compounds that had been added to those wells can be tested further as possible selective inhibitors of some of the kinases tested.

The scheme of the assay is shown in the top panel of FIG. 17. A chimeric linker molecule is prepared in which a 25 base pair oligonucleotide complementary to one of the anchors is crosslinked to a peptide substrate of a tyrosine phosphokinase enzyme. The chimeric oligo-peptide substrate self-assembles onto an array of oligonucleotide anchors, the kinase enzyme is used to phosphorylate the peptide portion of the chimera, and after the enzyme reaction is allowed to proceed, the amount of phosphorylation of the peptide is determined by anti-phoshotyrosine or anti-phosphoserine antibodies with an attached detection fluorophore or enzyme.

The results of the assay are shown in the lower panel. The homobifunctional crosslinker, DSS (Pierce), was used to attach the 5' amino group of an oligonucleotide linker to the N terminus of a peptide synthesized with a phosphorylated tyrosine. The sequence of the peptide in single-letter code was: TSEPQpYQPGENL (SEQ ID: 32), where pY represents phosphotyrosine. The chimera was either used directly or first brought to pH 14 for 60 minutes in order to partially hydrolyze the phosphate group from the tyrosine. The phosphorylated or partially dephosphorylated chimeric molecules were self-assembled onto complementary anchor molecules within a MAPS plate at the concentrations shown for one hour. After washing and blocking the wells with 0.3% BSA in SSPTP antiphosphotyrosine antibody crosslinked to HRP (antibody 4G10 from Upstate Biotechnology, Lake Placid, N.Y.) was added at a 1:3000 dilution in SSPTP for one hour, and the amount of antibody attached detected with chemiluminescence substrate, Super Signal Blaze. The image shown was accumulated on the CCD array for 1 minute. As expected a difference was seen in the amount of phosphate attached to the oligo-peptide. This difference is the basis for an assay measuring how active a series of kinases is when treated with different possible inhibitors.

Example 19

A Binding Assay for the Detection of Selective Inhibitors of the Interaction Between SH2 Domains and Phosphorylated Peptides SH2 domains serve as docking subunits of some growth regulatory proteins. The domains bind to phosphotyrosine containing proteins or peptides with imperfect specificity. That is, some phosphotyrosine peptides bind specifically to one or to few SH2 proteins while others bind widely to many SH2 proteins.

For this assay, the linkers are phosphorylated peptides covalently attached to oligonucleotides. The peptide moieties are selected for their ability to bind to a group of selected SH2 proteins. The linkers convert generic MAPS plates to plates with ligands specific for the group of SH2 proteins. 100 96-well MAPS plates bearing the ligands are generated. The proteins are isolated and labeled with, for example, a cy5 fluorescent molecule.

In order to screen for inhibitors of the SH2 domain/phosphopeptide interaction, the group of labeled SH2 proteins is added to each well of the 100 96-well MAPS plates, and in each well a different test compound is added. Hence the effect of each compound individually on the interaction of the SH2 proteins with their phosphopeptide ligands is tested. The assay is to measure the fluorescence of bound SH2 protein associated with each surface-bound peptide linker. For any well showing reduced fluorescence at some spots but not all spots, the compound added can be further tested as a putative selective inhibitor of SH2 docking.

Example 20

High Throughput Screening (see FIG. 22)

Shown is a high throughput MAPS plate demonstrating the detection of signal from 96 wells in a single experiment. Hybridization to the same oligonucleotide was measured with 16 replicates in 80 wells. As shown, the reproducibility of the 1280 hybridization assays was very high. The left-most and right-most columns served as controls to standardize the signal for different concentrations of the oligonucleotide.

In a similar fashion, 16 different oligonucleotides can be tested in each well, and the test repeated in the 80 different wells of the plate. Of course, an even greater number of different oligonucleotides or other probes, (e.g., 100 nucleotide probes) can be assayed in each well, and many plates can be tested simultaneously (e.g., 100 plates, such as 96-well microtiter plates). The large number of assays which can be performed on each sample (e.g., in the latter case, about 100 different assays) and the large number of samples which can be assayed simultaneously (e.g., in the latter case, about 96×100, or 9600 different samples) provides for very high throughput.

Example 21

Preparation of amplified target (see FIG. 23)

A PCR primer (Primer One) is attached to a solid support (e.g., a bead or a reaction vessel) via a chemical modification that has been introduced at the 5' terminus of the primer oligonucleotide. The primer comprises, 5' to 3', the chemical modification, a restriction enzyme site, and a sequence that is complementary to a target of interest (e.g., a cDNA copy of an mRNA of interest). The target is amplified by PCR, using as PCR primers the attached Primer One plus a Primer Two, which comprises, 5' to 3', a sequence that is specific for a detector oligonucleotide and a sequence that is complementary to a different portion of the target than that of Primer One. Following PCR amplification, the amplified target DNA is washed to remove excess reaction material and is released from the solid support by cleavage with a restriction enzyme specific for the restriction site on Primer One. The amplified primer is thus released into the liquid phase. Thermal and/or chemical procedures can be used to deactivate the restriction enzyme and to denature the double stranded DNA product. The released, single stranded DNA target molecules can then be contacted with a surface comprising anchors and/or linkers, and the target can be detected using detector oligonucleotides complementary to the detector-specific sequences of Primer Two.

Example 22

Preparation of Amplified Target

A PCR primer (Primer One) is attached to a solid support (e.g., a bead or a reaction vessel) via a chemical modification that has been introduced into the 5' terminus of the primer oligonucleotide. The primer comprises, 5' to 3', the chemical modification, a peptide sequence which can be cleaved by a protease, and a sequence which is complementary to a target of interest (e.g., a cDNA copy of an mRNA of interest). Instead of a peptide, any other element which can be cleaved specifically can also be used. Following PCR amplification as described, e.g., in Example 21, the PCR product, still attached to the solid support, is denatured and (optionally) washed, leaving behind a single stranded molecule attached to the support. The washed, attached, molecule can then be cleaved and released (e.g., by treatment with an appropriate protease), and contacted with a surface comprising anchors and/or linkers. Alternatively, the strand of the amplified target which is released following denaturation can be contacted with the surface comprising anchors and/or linkers. In either case, only one strand of the amplified target is contacted (e.g., hybridized) with a linker, so competition for hybridization from the opposite strand of the amplified target is eliminated and background is reduced. Linkers can be designed to be specific for either, or both, of the amplified target strands.

Example 23

Assay with Detection Linkers and Reporter Agents
(See FIG. 24)

A sample comprising an mRNA of interest is subjected to a nuclease protection procedure, using as a protection fragment an oligonucleotide which comprises a target specific moiety and a control overhang moiety, which is not complementary to the mRNA. Following nuclease digestion, the control overhang moiety can be cleaved off, as desired, as is illustrated in the left portion of the figure; or the overhang can fail to be digested, as is illustrated in the right portion of the figure. The resulting nuclease protection fragments are hybridized to a detection linker, which comprises a target-specific moiety and a control overhang-specific moiety. In the assay shown in the left part of the figure, the control overhang moiety of the detection linker remains unhybridized; by contrast, in the assay shown in the right part of the figure, the control overhang moiety of the detection linker hybridizes to the residual control overhang sequence of the protection fragment. In a subsequent step of the assay, a reporter reagent, which comprises a moiety that can interact with control overhang-specific moiety of the detection linker, is allowed to interact with the complexes. In the assay shown in the left part of the figure, the reporter reagent hybridizes to the control overhang-specific moiety of the detection linker, which remains available for hybridization, and the complex can be detected by virtue of the signaling entity on the reporter reagent. By contrast, in the assay shown in the right part of the figure, the reporter reagent is unable to bind to the complex because the complementary sequences are not available for hybridization, so no signal is associated with the complex.

In many of the assays of this invention, a reporter reagent can interact with any sequence present in a detection linker, not limited to a sequence specific for a control overhang.

Example 24

Multiple Fluors (See FIG. 25)

A region comprising five loci, A-E, is shown in FIG. 25. Each locus comprises a different group of substantially identical anchors, anchors A-E. To the anchors at locus A are hybridized four different types of linkers, each of which comprises a moiety specific for anchor A. However, each of the anchors comprises a different target-specific moiety: for targets 1, 2, 3 or 4. Therefore, after hybridization of targets to the anchor/linker complexes, targets 1, 2, 3, and 4 can all become localized at locus A. Similarly, four different types of linkers can hybridize to locus B. Each linker comprises a moiety specific for anchor B, but the target-specific moieties are specific for targets 5, 6, 7 or 8. In a similar fashion, targets 9-12 can become associated with locus C, targets 13-16 at locus D, and targets 17-20 at locus E. If each of these targets is labeled, either directly or indirectly, with a different, independently detectable fluor, such as, e.g., an upconvertable phosphore, one can independently detect all 20 targets at the five indicated loci.

Example 25

An Assay in High Throughput Format

In this example, a transcription assay of the invention is used to detect and quantify changes in a gene expression pattern, in a format ready for high throughput screening. All steps in the assay are performed robotically. Routine washing steps are not explicitly described. All reactions are carried out by conventional procedures, which are known in the art and/or described herein.

THP-1 human monocytes are grown in 96-well V-bottom microtiter plates, with 50,000 or 150,000 cells/well. The cells are either untreated or are differentiated with phorbol 12-myristate 13-acetate (PMA) for 48 hours, followed by activation with lipopolysaccharide (LPS) for four hours. Following treatment, the cells are lysed in guanidinium isothyocyanate and frozen until needed. mRNA is obtained using streptavidin-paramagnetic particles to which is bound biotin-poly dT. Alternatively, total RNA is obtained by extraction with tri-reagent (Sigma Chemical Co., St. Louis, Mo.). Samples comprising either mRNA or total RNA are subjected to a nuclease protection procedure, using as DNA protection fragments a mixture of thirteen 60-mer single strand oligonucleotides, each of which comprises, 5' to 3', a 25-mer specific for one of the thirteen targets of interest (GAPDH, IL-1, TNF-α, cathepsin G, cox-2, cyclin-2, vimentin, LD78-β, HMG-17, osteopontin, β-thromboglobin, angiotensin or actin); a 10-mer spacer; a 25-mer specific for a common oligonucleotide detector probe; and a 15-mer common control overhang sequence. mRNA is thereby converted into a stochiometric amount of "corresponding DNA protection fragment," which is detected in the assay. Control experiments in which these corresponding. DNA protection fragments are incubated with a probe specific for the control overhang sequence show that substantially only sequences specific for the mRNA targets of interest are present in the corresponding protection fragments, as expected if nuclease digestion has occurred as desired.

Surfaces are prepared according to the methods of the invention. In each well of a 96-well DNA Bind Plate is placed an array of sixteen different 25-mer oligonucleotide anchors. Fourteen different anchor species are used. One anchor species is used at three of the four corners of the array, and 13 different anchor species are used, one each at the remaining locations in the array. The anchors are then hybridized, in a defined orthogonal pattern, to 60-mer oligonucleotide linkers, each of which comprises, 5' to 3', a 25-mer corresponding to one of the thirteen targets of interest, a 10-mer spacer, and a 25-mer specific for one of the anchors. Thus, in each of the multiply repeated 16-spot arrays, each of the thirteen target-specific linkers is localized at a defined position (locus) in the array. See FIG. 18 for an illustration of such an orthogonal array. Linkers corresponding to GAPDH, a constitutively expressed housekeeping gene which serves as an internal normalization control, are represented at three loci within each array. Control experiments indicate that the linkers, as well as the protection fragments and detector oligonucleotides used in the experiment, exhibit the desired specificity.

Samples comprising the mixtures of corresponding protection fragments prepared as described above are hybridized to the anchor/linker arrays. Samples derived from either untreated or induced cultures are used. The presence and amount of hybridized protection fragments at each locus is then detected by hybridization to labeled detector oligonucleotides. In order to normalize the amount of signal at each locus, the detector oligonucleotides are diluted with appropriate amounts of blocked oligomers, as described herein. The amount of signal at each locus is processed and normalized to the control GAPDH signals. The data obtained are reproducible in eight replicate samples, as well as in samples prepared from three independent experiments, performed on different days. A summary of the relative abundance of the thirteen transcripts in one experiment is shown in the Table below.

| | Relative Intensity ($10^5$ Cells/Well) | | | | |
|---|---|---|---|---|---|
| | Control | | Induced | | |
| Gene | Average | CV (n = 16) | Average | CV (n = 16) | Ratio |
| GAPDH | 10110 | 7% | 9833 | 9% | 0.97 |
| IL-1 | 527 | 36% | 8124 | 38% | 15.40 |
| TNF | 229 | 35% | 2249 | 36% | 9.80 |
| GAPDH | 9591 | 11% | 10031 | 17% | 1.05 |
| Cathepsin G | 10394 | 31% | 19648 | 46% | 1.89 |
| COX-2 | 415 | 39% | 3557 | 25% | 8.58 |
| Cyclin-2 | 1728 | 23% | 2960 | 25% | 1.71 |
| Vimentin | 25641 | 25% | 71074 | 20% | 2.77 |
| LD78 | 1298 | 39% | 13437 | 20% | 10.35 |
| HMG-17 | 8286 | 19% | 2405 | 20% | 0.29 |
| Osteopontin | 5604 | 42% | 19053 | 46% | 3.40 |
| Thrombo-globulin | −53 | — | 31761 | 23% | >100 |
| GAPDH | 10299 | 13% | 10136 | 12% | 0.98 |
| Angiotensin | 3575 | 28% | 6561 | 31% | 1.84 |
| Actin | 12741 | 27% | 21802 | 23% | 1.71 |
| (blank) | 108 | — | 234 | — | |

Example 26

Computer Algorithm for Quantification of Multiple Array Plate Data

A preferred algorithm finds the position of all spots for a MAPS plate and automatically calculates a best-fit estimate of the amplitude of the signal for each data point.

Preferably, the algorithm is implemented by a computer program.

1—Select a small part of the image data, a 40×40 box, containing the intensity value of each pixel (picture element) of the image that includes the first well to be examined.
2—Define a function that calculates the intensity expected at each pixel position, using 16 unknowns. The unknowns are:

The amplitudes of each of 13 different microarray spots (that is, how bright are the real signals at each position of the DNA array). There are 13 of these for the 4×4 (=16) spots within each well because some of the 16 spots are duplicates of the same target.

The x offset and the y offset defining the exact position of the 4×4 array of spots within this particular well The background intensity of the picture within the well.

The function for each pixel position calculates the distance between the pixel and each spot, and adds up the contribution that each spot makes to the intensity observed at that pixel, by multiplying the spot amplitude by the impulse response function for the given distance. For the images used the impulse response function is defined by the sum of a Gaussian and a Lorentzian of appropriate (constant) radii.

3—Start the fitting for the current well by guessing the values of the parameters quickly. To do this, calculate the average image intensity for 16 regions of the picture where the spots are expected to be. Subtract an offset from these 16 averages, and scale the difference by a constant factor. The offset and scaling constant are defined empirically. Rearrange the results to match up the 16 spots with the 13 amplitudes. For the background and offets use any small numbers.
4—Optimize the fitted values (for the 16 unknowns) by curve fitting. In particular use a non-linear least squares algorithm with Marquadt procedure for linearizing the fitting function, fitting 16 unknowns to 40×40=1600 equations (although of course not all equations are linearly independent).
5—Use the x, y offset as fitted for the current well to estimate with improved precision where the grid will be for the next well of the microplate. It is expected to be 9 millimeters offset relative to the next neighbor well (converted to distance in the number of pixels by the magnification factor of the imaging system). Since the distance between wells is small relative to the size of the plate, using local estimates of position is most accurate.
6—With the improved estimate of position, define a smaller box of image for the next well, moving to a 30×30 box of pixels. This makes the fitting proceed more quickly.

Go back to step 2 and repeat for each well.

Example 27

High Throughput Screening (See FIGS. 26 and 27)

FIG. 26 illustrates raw image data for an assay using detection linkers and a single reporter reagent. The assay tests the expression of 13 native mRNA species from 96 different cell samples. Each well of a 96-well plate contains $10^5$ THP-1 cells untreated (left half of the figure), or induced to monocytes with PMA and LPS (right half).

The pattern of expression changes consistently. IL-1, TNF, COX-2, Vimentin, LD78, Osteopontin, and beta-Thromboglobulin are induced. Cathepsin-G, Cyclin-b, HMG-17 and Angiotensin are turned off. GAPDH and Actin are unchanged.

FIG. 27 presents the spatial arrangement of genes for the THP-1 cells, along with two sample wells of data (selected from FIG. 26).

The oligos used in this experiments are listed below. For some targets, the intensity of signal is reduced by diluting the detection linker with an incomplete detection linker oligonucleotide, containing the 25 bases complementary to the protection fragment but not containing the sequence complementary to the reporter reagent. These incomplete oligos are referred to as "attenuation factors."

Table 1 presents quantification of the raw data presented above. This screening assay is done in high throughput fashion. Cells are grown and treated in 96-well plates at an average of $10^5$ cells/well, the number of cells that can be conveniently handled in microplates. An expression pattern for 13 genes is measured in high throughput format, from small cell samples. The results obtained using assay corroborate and extend the literature, as summarized in Table 1. The assay can detect less than one copy per cell. The literature references reflect observations accumulated from a variety of related cell types, such as U-937 cells. The large differences seen between the Control and Induced conditions result from the very low background signals for our measurements. The use of detection linkers, allowing for only one species of reporter reagent helps to reduce the background for the assay. This is because the total concentration of HRP—containing reporter reagent is much reduced.

TABLE 1

Relative Abundance (RNA Molecules per cell[+])
MAPS 96-16 Format, $10^5$ Cells/Well

| Gene | Control | Induced | Literature |
|---|---|---|---|
| GAPDH | 30 ± *7% | 30 ± 14% | No Change |
| IL1-beta | **nd | 684 ± 14% | Increase |
| TNF | 3.0 ± 40% | 214 ± 23% | Increase |
| Cathepsin-G | 53 ± 8% | nd | Decrease |
| COX-2 | nd | 8.3 ± 23% | Increase |
| Cyclin-2 | 2.8 ± 11% | 0.5 ± 46% | No Change |

TABLE 1-continued

Relative Abundance (RNA Molecules per cell[+])
MAPS 96-16 Format, $10^5$ Cells/Well

| Gene | Control | Induced | Literature |
|---|---|---|---|
| Vimentin | nd | 37 ± 33% | Increase |
| LD78-b | nd | 3360 ± 28% | Increase |
| HMG-17 | 336 ± 5% | 33 ± 23% | Decrease |
| Osteopontin | nd | 18 ± 23% | Not Reported |
| Thromboglobulin | nd | 66 ± 15% | Increase |
| Angiotensin | 0.5 ± 18% | 0.1 ± 66% | Not Reported |
| Actin | 79 ± 7% | 43 ± 21% | No Change |

[+]Estimated values, assuming GAPDH was at 30/cell
*% CV (Std Dev/Mean as a %) (n = 48)
**nd = not detectable The oligos used in Example 27 with detection linkers and a single probe are:

```
Fixed Probe:
CACCTCCAAACAGTGAAGGAGAGCA (conjugated to HRP)          (SEQ ID:33)

Target#1; ID: MI7851GAPDH (572-513)
Anchor: - length = 25

CGCCGGTCGAGCGTTGTGGGAGCGC                              (SEQ ID:34)

Target: - length = 60
TGAGAAGTATGACAACAGCCTCAAGATCATCAGCAATGCCTCCTGCACCACC  (SEQ ID:35)

AACTGCTT

Linker: - length = 60
ATGCCTCCTGCACCACCAACTGCTTGATACTGAGTGCGCTCCCACAACGCTCG (SEQ ID:36)

ACCGGCG

Protection Fragment: - length = 75
AAGCAGTTGGTGGTGCAGGAGGCATTGCTGATGATCTTGAGGCTGTTGTCAT  (SEQ ID:37)

ACTTCTCAGCTTGTCTAAGTCTG

Detection-Linker: - length = 60
TGCTCTCCTTCACTGTTTGGAGGTGGATACTGAGTTGAGAAGTATGACAACAG (SEQ ID:38)

CCTCAAG

Attenuation Factor: - length = 25
TGAGAAGTATGACAACAGCCTCAAG                              (SEQ ID:39)

Target#2; ID: M 15840 ILI-beta (4392-4333)
Anchor: - length = 25
TCCACGTGAGGACCGGACGGCGTCC                              (SEQ ID:40)

Target: - length = 60
CGACACATGGGATAACGAGGCTTATGTGCACGATGCACCTGTACGATCACTG  (SEQ ID:41)

AACTGCAC

Linker: - length = 60
CACCTGTACGATCACTGAACTGCACGATACTGAGTGGACGCCGTCCGGTCCT  (SEQ ID:42)

CACGTGGA

Protection Fragment: - length = 75
GTGCAGTTCAGTGATCGTACAGGTGCATCGTGCACATAAGCCTCGTTATCCCA (SEQ ID:43)

TGTGTCGGCTTGTCTAAGTCTG

Detection-Linker: - length = 60
TGCTCTCCTTCACTGTTTGGAGGTGGATACTGAGTCGACACATGGGATAACGA (SEQ ID:44)

GGCTTAT

Attenuation Factor: - length = 25
CGACACATGGGATAACGAGGCTTAT                              (SEQ ID:45)
```

```
Target#3; ID: M1O988TNF (780-721)
Anchor: - length = 25
CACTACGGCTGAGCACGTGCGCTGC                                   (SEQ ID:46)

Target: - length = 60
CGGAACCCAAGCTTAGAACTTTAAGCAACAAGACCACCACTTCGAAACCTGG         (SEQ ID:47)

GATTCAGG

Linker: - length = 60
ACCACTTCGAAACCTGGGATTCAGGGATACTGAGTGCAGCGCACGTGCTCAG         (SEQ ID:48)

CCGTAGTG

Protection Fragment: - length = 75
CCTGAATCCCAGGTTTCGAAGTGGTGGTCTTGTTGCTTAAAGTTCTAAGCTTG        (SEQ ID:49)

GGTTCCGGCTTGTCTAAGTCTG

Detection-Linker: - length = 60
TGCTCTCCTTCACTGTTTGGAGGTGGATACTGAGTCGGAACCCAAGCTTAGAA        (SEQ ID:50)

CTTTAAG

Attenuation Factor: - length = 25
CGGAACCCAAGCTTAGAACTTTAAG                                    (SEQ ID:51)

Target#4; ID: MI7851GAPDH (572-513)
(same as for Target #1)

Target#5; ID: MI6117Cathepsin-G (373-314)
Anchor: - length = 25
GAACCGCTCGCGTGTTCTACAGCCA                                    (SEQ ID:52)

Target: - length = 60
GCGGACCATCCAGAATGACATCATGTTATTGCAGCTGAGCAGAAGAGTCAGA         (SEQ ID:53)

CGGAATCG

Linker: - length = 60
TGAGCAGAAGAGTCAGACGGAATCGGATACTGAGTTGGCTGTAGAACACGC          (SEQ ID:54)

GAGCGGTTC

Protection Fragment: - length = 75
CGATTCCGTCTGACTCTTCTGCTCAGCTGCAATAACATGATGTCATTCTGGAT        (SEQ ID:55)

GGTCCGCGCTTGTCTAAGTCTG

Detection-Linker: - length = 60
TGCTCTCCTTCACTGTTTGGAGGTGGATACTGAGTGCGGACCATCCAGAATGA        (SEQ ID:56)

CATCATG

Attenuation Factor length = 25
GCGGACCATCCAGAATGACATCATG                                    (SEQ ID:57)

Target#6; ID: M90100COX-2 (240-181)
Anchor: - length = 25
CTCGTTCCGCGTCCGTGGCTGCCAG                                    (SEQ ID:58)

Target: - length = 60
CCGAGGTGTATGTATGAGTGTGGGATTTGACCAGTATAAGTGCGATTGTACC         (SEQ ID:59)

CGGACAGG

Linker: - length = 60
ATAAGTGCGATTGTACCCGGACAGGGATACTGAGTCTGGCAGCCACGGACGC         (SEQ ID:60)

GGAACGAG

Protection Fragment: - length = 75
CCTGTCCGGGTACAATCGCACTTATACTGGTCAAATCCCACACTCATACATAC        (SEQ ID:61)

ACCTCGGGCTTGTCTAAGTCTG

Detection-Linker: - length = 60
TGCTCTCCTTCACTGTTTGGAGGTGGATACTGAGTCCGAGGTGTATGTATGAG        (SEQ ID:62)

TGTGGGA
```

-continued

Attenuation Factor: - length = 25
CCGAGGTGTATGTATGAGTGTGGGA (SEQ ID:63)

Target #7; ID: M74091 cyclin (932-873)
Anchor: - length = 25
CGGTCGGCATGGTACCACAGTCCGC (SEQ ID:64)

Target: - length = 60
CACCTCCAAACAGTGAAGGAGAGCAGGGTCCAAATGGAAGTCAGAACTCTA (SEQ ID:65)
GCTACAGCC Linker: - length = 60
GGAAGTCAGAACTCTAGCTACAGCCGATACTGAGTGCGGACTGTGGTACCAT (SEQ ID:66)
GCCGACCG Protection Fragment: - length = 75
GGCTGTAGCTAGAGTTCTGACTTCCATTTGGACCCTGCTCTCCTTCACTGTTTG (SEQ ID:67)
GAGGTGGCTTGTCTAAGTCTG Detection-Linker: - length = 60
TGCTCTCCTTCACTGTTTGGAGGTGGATACTGAGTCACCTCCAAACAGTGAAG (SEQ ID:68)
GAGAGCA Attenuation Factor: - length = 25
CACCTCCAAACAGTGAAGGAGAGCA (SEQ ID:69)

Target#8; ID: MI4144vimentin (1338-1279)
Anchor: - length = 25
GCGCGCCGCGTTATGCATCTCTTCG (SEQ ID:70)

Target: - length = 60
GTGGATGCCCTTAAAGGAACCAATGAGTCCCTGGAACGCCAGATGCGTGAAA (SEQ ID:71)
TGGAAGAG Linker: - length = 60
ACGCCAGATGCGTGAAATGGAAGAGGATACTGAGTCGAAGAGATGCATAAC (SEQ ID:72)
GCGGCGCGC Protection Fragment: - length = 75
CTCTTCCATTTCACGCATCTGGCGTTCCAGGGACTCATTGGTTCCTTTAAGGG (SEQ ID:73)
CATCCACGCTTGTCTAAGTCTG Detection-Linker: - length = 60
TGCTCTCCTTCACTGTTTGGAGGTGGATACTGAGTGTGGATGCCCTTAAAGGA (SEQ ID:74)
ACCAATG Attenuation Factor: - length = 25
GTGGATGCCCTTAAAGGAACCAATG (SEQ ID:75)

Target #9; ID: D90145 LD78-b (2049-1990)
Anchor: - length = 25
GTTAGCATACGTGTCACCACACCGG (SEQ ID:76)

Target: - length = 60
CACCTCCCGACAGATTCCACAGAATTTCATAGCTGACTACTTTGAGACGAGC (SEQ ID:77)
AGCCAGTG Linker: - length = 60
ACTACTTTGAGACGAGCAGCCAGTGGATACTGAGTCCGGTGTGGTGACACGT (SEQ ID:78)
ATGCTAAC Protection Fragment: - length = 75
CACTGGCTGCTCGTCTCAAAGTAGTCAGCTATGAAATTCTGTGGAATCTGTCG (SEQ ID:79)
GGAGGTGGCTTGTCTAAGTCTG Detection-Linker: - length = 60
TGCTCTCCTTCACTGTTTGGAGGTGGATACTGAGTCACCTCCCGACAGATTCC (SEQ ID:80)
ACAGAAT

```
Attenuation Factor: - length = 25
CACCTCCCGACAGATTCCACAGAAT                                    (SEQ ID:81)

Target #10; ID: X13546 HMG-17 M12623-mRNA (191-132)
Anchor: - length = 25
CGTCAGTCCGTCGGCCAGCTCTTCC                                    (SEQ ID:82)

Target: - length = 60
CAAAGGTGAAGGACGAACCACAGAGAAGATCCGCGAGGTTGTCTGCTAAAC          (SEQ ID:83)

CTGCTCCTC

Linker: - length = 60
AGGTTGTCTGCTAAACCTGCTCCTCGATACTGAGTGGAAGAGCTGGCCGACG         (SEQ ID:84)

GACTGACG

Protection Fragment: - length = 75
GAGGAGCAGGTTTAGCAGACAACCTCGCGGATCTTCTCTGTGGTTCGTCCTTC        (SEQ ID:85)

ACCTTTGGCTTGTCTAAGTCTG

Detection-Linker: - length = 60
TGCTCTCCTTCACTGTTTGGAGGTGGATACTGAGTCAAAGGTGAAGGACGAA         (SEQ ID:86)

CCACAGAG

Attenuation Factor: - length = 25
CAAAGGTGAAGGACGAACCACAGAG                                    (SEQ ID:87)

Target #11; ID: X13694 Osteopontin (783-724)
Anchor: - length = 25
ATCCAGTTAACCACATGCTAGTACC                                    (SEQ ID:88)

Target: - length = 60
CCGTGGGAAGGACAGTTATGAAACGAGTCAGCTGGATGACCAGAGTGCTGA          (SEQ ID:89)

AACCCACAG

Linker: - length = 60
ATGACCAGAGTGCTGAAACCCACAGGATACTGAGTGGTACTAGCATGTGGTT         (SEQ ID:90)

AACTGGAT

Protection Fragment: - length = 75
CTGTGGGTTTCAGCACTCTGGTCATCCAGCTGACTCGTTTCATAACTGTCCTTC       (SEQ ID:91)

CCACGGGCTTGTCTAAGTCTG

Detection-Linker: - length = 60
TGCTCTCCTTCACTGTTTGGAGGTGGATACTGAGTCCGTGGGAAGGACAGTTA        (SEQ ID:92)

TGAAACG

Attenuation Factor: - length = 25
CCGTGGGAAGGACAGTTATGAAACG                                    (SEQ ID:93)

Target#12; ID: MI7017b-thromboglobulin(142-83)
Anchor: - length = 25
TTAGCGTTGGCCGAGGTTCATAGCC                                    (SEQ ID:94)

Target: - length = 60
GTGTAAACATGACTTCCAAGCTGGCCGTGGCTCTCTTGGCAGCCTTCCTGATT        (SEQ ID:95)

TCTGCAG

Linker: - length = 60
TTGGCAGCCTTCCTGATTTCTGCAGGATACTGAGTGGCTATGAACCTCGGCCA        (SEQ ID:96)

ACGCTAA

Protection Fragment: - length = 75
CTGCAGAAATCAGGAAGGCTGCCAAGAGAGCCACGGCCAGCTTGGAAGTCA          (SEQ ID:97)

TGTTTACACGCTTGTCTAAGTCTG

Detection-Linker: - length = 60
TGCTCTCCTTCACTGTTTGGAGGTGGATACTGAGTGTGTAAACATGACTTCCA        (SEQ ID:98)

AGCTGGC
```

-continued

```
Attenuation Factor: - length = 25
GTGTAAACATGACTTCCAAGCTGGC                                    (SEQ ID:99)

Target#13; ID: MI7851GAPDH(572-513)
(same as for Target #1)

Target #14; ID: K02215 angiotensin (805-746)
Anchor: - length = 25
CATTACGAGTGCATTCGCATCAAGG                                    (SEQ ID:100)

Target: - length = 60
CACGCTCTCTGGACTTCACAGAACTGGATGTTGCTGCTGAGAAGATTGACAG         (SEQ ID:101)

GTTCATGC

Linker: - length = 60
GCTGAGAAGATTGACAGGTTCATGCGATACTGAGTCCTTGATGCGAATGCAC         (SEQ ID:102)

TCGTAATG

Protection Fragment: - length = 75
GCATGAACCTGTCAATCTTCTCAGCAGCAACATCCAGTTCTGTGAAGTCCAGA        (SEQ ID:103)

GAGCGTGGCTTGTCTAAGTCTG

Detection-Linker: - length = 60
TGCTCTCCTTCACTGTTTGGAGGTGGATACTGAGTCACGCTCTCTGGACTTCA        (SEQ ID:104)

CAGAACT

Attenuation Factor: - length = 25
CACGCTCTCTGGACTTCACAGAACT                                    (SEQ ID:105)

Target#15; ID: MI0277Actin (2627-2568)
Anchor: - length = 25
ATCATGTAAGTCTTCGGTCGGTGGC                                    (SEQ ID:106)

Target: - length = 60
GAGTCCTGTGGCATCCACGAAACTACCTTCAACTCCATCATGAAGTGTGACGT        (SEQ ID:107)

GGACATC

Linker: - length = 60
CATCATGAAGTGTGACGTGGACATCGATACTGAGTGCCACCGACCGAAGACT         (SEQ ID:108)

TACATGAT

Protection Fragment: - length = 75
GATGTCCACGTCACACTTCATGATGGAOTTGAAGGTAGTTTCGTGGATGCCAC        (SEQ ID:109)

AGGACTCGCTTGTCTAAGTCTG

Detection-Linker: - length = 60
TGCTCTCCTTCACTGTTTGGAGGTGGATACTGAGTGAGTCCTGTGGCATCCAC        (SEQ ID:110)

GAAACTA

Attenuation Factor: - length = 25
GAGTCCTGTGGCATCCACGAAACTA                                    (SEQ ID:111)

Target #16; (this spot is not used)
```

Example 28

Simultaneous Detection of DNA and RNA (See FIG. 29)

THP-1 human monocytes are grown in 96-well V-bottom microtiter plates, with 30,000 to 150,000 cells/well. Control cells which have not been differentiated with PMA or activated with LPS are used, because the RNAs for certain genes (e.g., IL-2, Cox-2, LD78, Osteopontin and Thromboglobulin) are not present in those cells and therefore only DNA is measured in the assay; whereas both DNA and RNA for GAPDH are present and measured. The cells are heated to 105° C. in an aqueous medium (lysis buffer), and nuclease protection fragments specific for the targets of interest are added to the lysates. Lysis at elevated temperature releases DNA in a measurable form, as well as RNA. For the measurement of DNA, the nuclease protection fragments added are those for IL-1, Cox-2, LD78, Osteopontin and Thromboglobulin. For the measurement of both DNA and RNA, the preceding nuclease protection fragments, as well as one specific for GAPDH, are added. Nuclease protection reactions are performed in the wells as described elsewhere herein.

The arrays are formed and the hybridization of protection fragments is performed essentially as described in Example 27. Detection of DNA vs DNA+RNA is done by serial hybridization of detection linkers. Serial hybridization is performed here in order to balance the signals from RNA and DNA targets (as discussed below); serial hybridization is, of course, not a requirement for assays in which DNA and RNA targets are detected together. In the first round, detection linkers for IL-2, Cox-2, LD78, Osteopontin and Thromboglobulin are added. In the second round, the detection linker for GAPDH is added. Serial hybridization is performed in order to image the DNA signal, which is relatively much weaker than the RNA signal due to much lower copy number per sample, for a longer period of time in order to accumulate a higher signal intensity.

The results are presented in FIG. 29. The left panel illustrates that when genomic DNA alone is examined, the genomic sequences tested—IL-1, Cox-2, LD78, Osteopontin and Thromboglobulin—can all be detected at the appropriate loci, and are present in approximately the same amounts. That genomic DNA is being measured is indicated by Table 1, which shows that in such control cells, RNA for these genes is not detectable. The right panel, in which both the DNA and RNA are measured, but a much shorter image exposure time is collected such that the DNA signal is much weaker than in the left panel, shows that when DNA and RNA are examined together, the control genomic sequences can be detected as before, as internal normalization standards, and the expressed gene—GAPDH—is present at a much higher level than the controls. By quantitating the relative amounts of signal in the controls and the expressed GAPDH mRNA, one can calculate the amount of mRNA expressed per cell.

Example 29

Detection of Expressed SNPs (See FIGS. 30 and 31)

FIG. 30 schematically illustrates one type of assay for expressed SNPs. Here, a nuclease protection fragment is designed to hybridize to the region of an RNA containing a SNP, in such a manner that when an appropriate enzyme (e.g., RNAse H) is added, if the nuclease protection fragment has hybridized to RNA for which there is a mismatched base (here, the SNP), the enzyme will cleave the nuclease protection fragment. In this example, the resulting cleaved fragment cannot hybridize to the array (e.g., due to the hybridization conditions such as temperature used). In other embodiments, hybridization to the array can occur, but a detection linker cannot bind to the cleaved protection fragment (e.g., due to the hybridization conditions such as temperature used); or the cleavage occurs in such a way that the cleaved protection fragment cannot hybridize simultaneously to the array and to a detection linker.

FIG. 31 illustrates the results of such an assay, performed by conventional methods as described herein. Wild type actin is used as an internal control, and a protection fragment corresponding to GAPDH containing an engineered SNP is differentiated from a protection fragment corresponding to wild type GAPDH. FIG. 31 depicts the measurement of multiple samples containing either wild type GAPDH and wild type actin (left column and left panel of blow-up) or containing SNP GAPDH and wild type actin (right column and right panel of blow-up). The center panel of the blow-up depicts the array layout.

Example 30

High Throughput Screening (See FIGS. 32-35)

Figure 32:
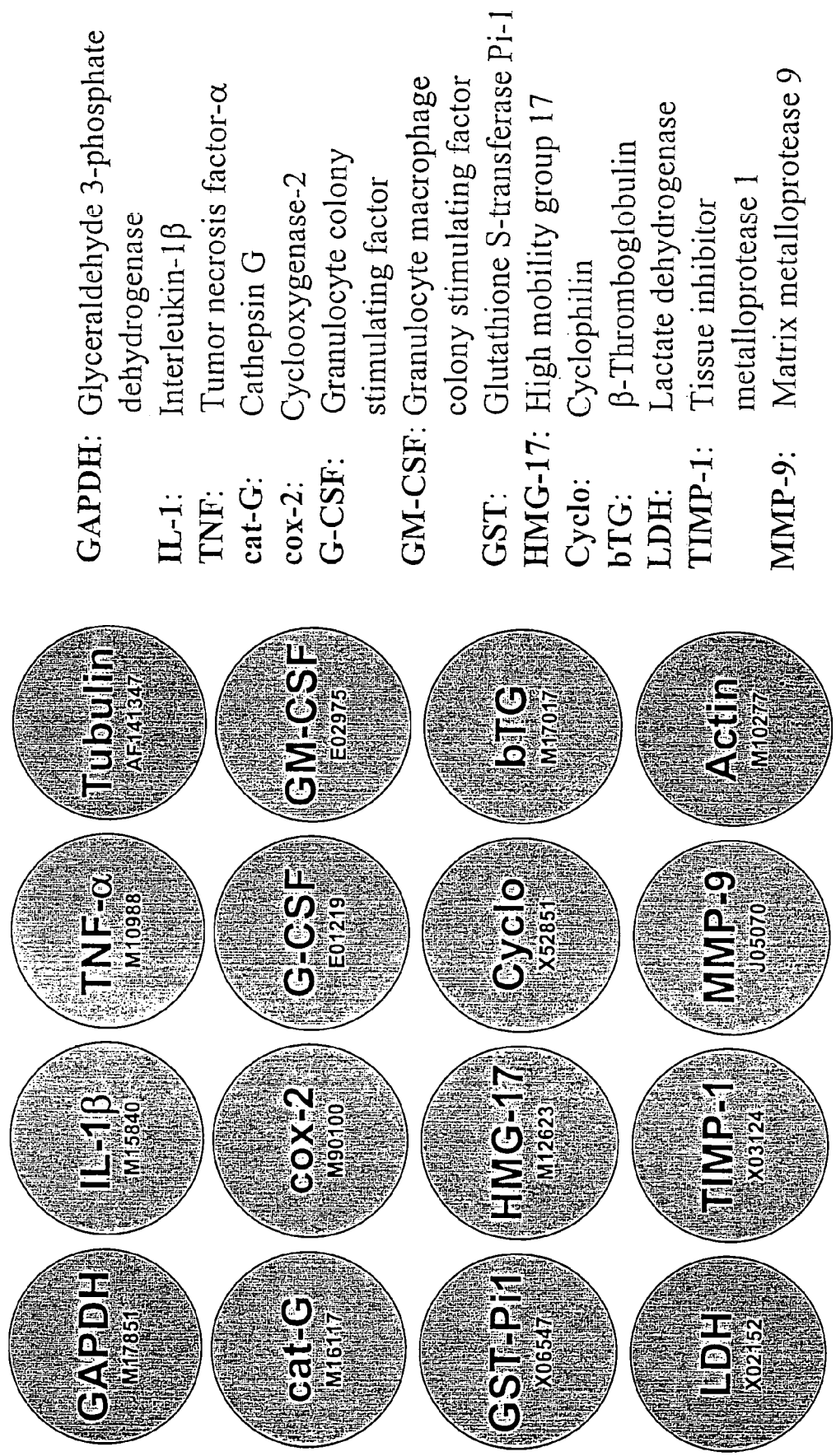

Transcription assays are performed essentially as described in Example 28, except, e.g., the anchors are placed on irradiated plates rather than DNA Bind plates. The same anchors described in Example 27 are used, but certain targets in the array are changed, namely, only one anchor is used to measure GAPDH, and Tubulin, actin, and LDH are added. The other targets measured are IL-1, TNF-a, Cathepsin G, Cox-2, G-CSF, GM-CSF, GST-Pi1, HMG-17, Cyclophilin, b-Thromboglobulin, TIMP-1, MMP-9. The array is depicted in FIG. 32 and the linker and nuclease protection fragment sequences are given below. Approximately 30,000 cells are used per well (not adjusted for continued proliferation of control cells during the course of PMA and LDH treatment of the treated cells).

Sequences:

```
Target #1 GAPDH (same as Target #1 example 27)

Target #2 IL-1b (same as Target #2 Example 27)

Target #3 TNF-a (same as Target #3 Example 27)

Target #4 Tubulin (AF141347)
Anchor: - length = 25
TAAGCGTCTCTAGGAAGGGACGTGG                                    (SEQ ID:112)

Target: - length = 60
GACGTGGTTCCCAAAGATGTCAATGCTGCCATTGCCACCATCAAGACCAAGC         (SEQ ID:113)

GTACCATC

Linker: - length = 60
CACCATCAAGACCAAGCGTACCATCGATACTGAGTCCACGTCCCTTCCTAGA         (SEQ ID:114)

GACGCTTA

Protection Fragment: - length = 75
GATGGTACGCTTGGTCTTGATGGTGGCAATGGCAGCATTGACATCTTTGGGA         (SEQ ID:115)

ACCACGTCGCTTGTCTAAGTCTG

Detection-Linker: - length = 60
TGCTCTCCTTCACTGTTTGGAGGTGGATACTGAGTGACGTGGTTCCCAAAGAT        (SEQ ID:116)

GTCAATG
```

-continued

```
Attenuation Factor: - length = 25
GACGTGGTTCCCAAAGATGTCAATG                                   (SEQ ID:117)

Target #5 Cathepsin-G (same as Target #5 Example 27)

Target #6 Cox-2 (same as Target #6 Example 27)

Target #7 G-CSF (E01219)
Anchor: - length = 25
CGGTCGGCATGGTACCACAGTCCGC                                   (SEQ ID:118)

Target: - length = 60
GAGGGAGCAGACAGGAGGAATCATGTCAGGCCTGTGTGTGAAAGGAAGCTC         (SEQ ID:119)

CACTGTCAC

Linker: - length = 60
GTGTGAAAGGAAGCTCCACTGTCACGATACTGAGTGCGGACTGTGGTACCAT        (SEQ ID:120)

GCCGACCG

Protection Fragment: - length = 75
GTGACAGTGGAGCTTCCTTTCACACACAGGCCTGACATGATTCCTCCTGTCTG       (SEQ ID:121)

CTCCCTCGCTTGTCTAAGTCTG

Detection-Linker: - Length = 60
TGCTCTCCTTCACTGTTTGGAGGTGGATACTGAGTGAGGGAGCAGACAGGAG        (SEQ ID:122)

GAATCATG

Attenuation Factor: - length = 25
GAGGGAGCAGACAGGAGGAATCATG                                   (SEQ ID:123)

Target #8 GM-CSF (E02975)
Anchor: - length = 25
GCGCGCCGCGTTATGCATCTCTTCG                                   (SEQ ID:124)

Target: - length = 60
CACTACAAGCAGCACTGCCCTCCAACCCCGGAAACTTCCTGTGCAACCCAGA        (SEQ ID:125)

TTATCACC

Linker: - length = 60
TTCCTGTGCAACCCAGATTATCACCGATACTGAGTCGAAGAGATGCATAACG        (SEQ ID:126)

CGGCGCGC

Protection Fragment: - length = 75
GGTGATAATCTGGGTTGCACAGGAAGTTTCCGGGGTTGGAGGGCAGTGCTGC        (SEQ ID:127)

TTGTAGTGGCTTGTCTAAGTCTG

Detection-Linker: - length = 60
TGCTCTCCTTCACTGTTTGGAGGTGGATACTGAGTCACTACAAGCAGCACTGC       (SEQ ID:128)

CCTCCAA

Attenuation Factor: - length = 25
CACTACAAGCAGCACTGCCCTCCAA                                   (SEQ ID:129)

Target #9 GST-PI1 X06547
Anchor: - length = 25
GTTAGCATACGTGTCACCACACCGG                                   (SEQ ID:130)

Target - length = 60
CAGGGAGGCAAGACCTTCATTGTGGGAGACCAGATCTCCTTCGCTGACTACA        (SEQ ID:131)

ACCTGCTG

Linker: - length = 60
CTCCTTCGCTGACTACAACCTGCTGGATACTGAGTCCGGTGTGGTGACACGTA       (SEQ ID:132)

TGCTAAC

Protection Fragment: - length = 75
CAGCAGGTTGTAGTCAGCGAAGGAGATCTGGTCTCCCACAATGAAGGTCTTG        (SEQ ID:133)

CCTCCCTGGCTTGTCTAAGTCTG
```

-continued

Detection-Linker: - length = 60
TGCTCTCCTTCACTGTTTGGAGGTGGATACTGAGTCAGGGAGGCAAGACCTTC    (SEQ ID:134)

ATTGTGG

Attenuation Factor: - length = 25
CAGGGAGGCAAGACCTTCATTGTGG    (SEQ ID:135)

Target #10 HMG-17 (same as Target #10 Example 27)

Target #11 Cyclophilin X52851

Anchor: - length = 25
ATCCAGTTAACCACATGCTAGTACC    (SEQ ID:136)

Target: - length = 60
GGGTTTATGTGTCAGGGTGGTGACTTCACACGCCATAATGGCACTGGTGGCA    (SEQ ID:137)

AGTCCATC

Linker: - length = 60
TAATGGCACTGGTGGCAAGTCCATCGATACTGAGTGGTACTAGCATGTGGTT    (SEQ ID:138)

AACTGGAT

Protection Fragment: - length = 75
GATGGACTTGCCACCAGTGCCATTATGGCGTGTGAAGTCACCACCCTGACAC    (SEQ ID:139)

ATAAACCCGCTTGTCTAAGTCTG

Detection-Linker: - length = 60
TGCTCTCCTTCACTGTTTGGAGGTGGATACTGAGTGGGTTTATGTGTCAGGGT    (SEQ ID:140)

GGTGACT

Attenuation Factor: - length = 25
GGGTTTATGTGTCAGGGTGGTGACT    (SEQ ID:141)

Target #12 b-Thromboglobulin
(same as Target #12 Example 27)

Target #13 LDH X02152
Anchor: - length = 25
TCTCGGTCTGGAACGCCCGGCAACT    (SEQ ID:142)

Target: - length = 60
GGTGGTTGAGAGTGCTTATGAGGTGATCAAACTCAAAGGCTACACATCCTGG    (SEQ ID:143)

GCTATTGG

Linker: - length = 60
AAGGCTACACATCCTGGGCTATTGGGATACTGAGTAGTTGCCGGGCGTTCCA    (SEQ ID:144)

GACCGAGA

Protection Fragment: - length = 75
CCAATAGCCCAGGATGTGTAGCCTTTGAGTTTGATCACCTCATAAGCACTCTC    (SEQ ID:145)

AACCACCGCTTGTCTAAGTCTG

Detection-Linker: - length = 60
TGCTCTCCTTCACTGTTTGGAGGTGGATACTGAGTGGTGGTTGAGAGTGCTTA    (SEQ ID:146)

TGAGGTG

Attenuation Factor: - length = 25
GGTGGTTGAGAGTGCTTATGAGGTG    (SEQ ID:147)

Target #14 TIMP-1 X03124
Anchor: - length = 25
CATTACGAGTGCATTCGCATCAAGG    (SEQ ID:148)

-continued

Target: - length = 60
CACCAAGACCTACACTGTTGGCTGTGAGGAATGCACAGTGTTTCCCTGTTTAT (SEQ ID:149)

CCATCCC

Linker: - length = 60
CAGTGTTTCCCTGTTTATCCATCCCGATACTGAGTCCTTGATGCGAATGCACT (SEQ ID:150)

CGTAATG

Protection Fragment: - length = 75
GGGATGGATAAACAGGGAAACACTGTGCATTCCTCACAGCCAACAGTGTAGG (SEQ ID:151)

TCTTGGTGGCTTGTCTAAGTCTG

Detection-Linker: - length = 60
TGCTCTCCTTCACTGTTTGGAGGTGGATACTGAGTCACCAAGACCTACACTGT (SEQ ID:152)

TGGCTGT

Attenuation Factor: - length = 25
CACCAAGACCTACACTGTTGGCTGT (SEQ ID:153)

Target #15 MMP-9 J05070
Anchor: - length = 25
ATCATGTAAGTCTTCGGTCGGTGGC (SEQ ID:154)

Target: - length = 60
GCAACGTGAACATCTTCGACGCCATCGCGGAGATTGGGAACCAGCTGTATTT (SEQ ID:155)

GTTCAAGG

Linker: - length = 60
GGGAACCAGCTGTATTTGTTCAAGGGATACTGAGTGCCACCGACCGAAGACT (SEQ ID:156)

TACATGAT

Protection Fragment: - length = 75
CCTTGAACAAATACAGCTGGTTCCCAATCTCCGCGATGGCGTCGAAGATGTTC (SEQ ID:157)

ACGTTGCGCTTGTCTAAGTCTG

Detection-Linker: - length = 60
TGCTCTCCTTCACTGTTTGGAGGTGGATACTGAGTGCAACGTGAACATCTTCG (SEQ ID:158)

ACGCCAT

Attenuation Factor: - length = 25
GCAACGTGAACATCTTCGACGCCAT (SEQ ID:159)

Target #16 Actin M10277
Anchor: - length = 25
CTGAGTCCTCCGGTGCCTACGTGGC (SEQ ID:160)

Target: - length = 60
GAGTCCTGTGGCATCCACGAAACTACCTTCAACTCCATCATGAAGTGTGACGT (SEQ ID:161)

GGACATC

Linker: - length = 60
CATCATGAAGTGTGACGTGGACATCGATACTGAGTGCCACGTAGGCACCGGA (SEQ ID:162)

GGACTCAG

Protection Fragment: - length = 75
GATGTCCACGTCACACTTCATGATGGAGTTGAAGGTAGTTTCGTGGATGCCAC (SEQ ID:163)

AGGACTCGCTTGTCTAAGTCTG

Detection-Linker: - length = 60
TGCTCTCCTTCACTGTTTGGAGGTGGATACTGAGTGAGTCCTGTGGCATCCAC (SEQ ID:164)

GAAACTA

Attenuation Factor: - length = 25
GAGTCCTGTGGCATCCACGAAACTA (SEQ ID:165)

Figure 33:
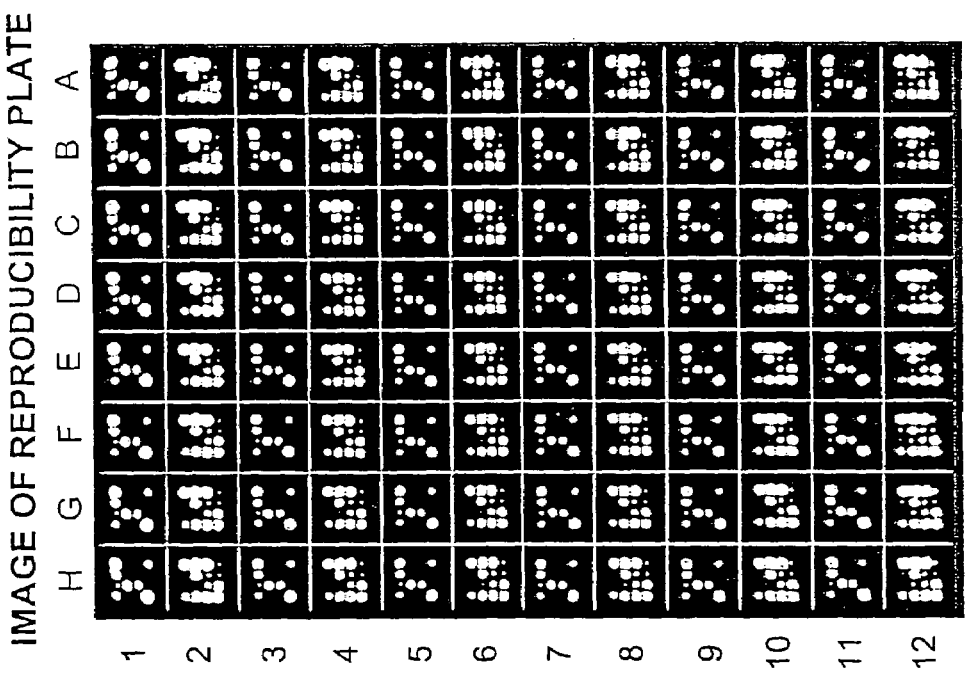

FIG. 33 shows that the reproducibility of the assay is high, providing a % CV range of about 3% to 13% when 30,000 cells are analyzed.

Figure 34:
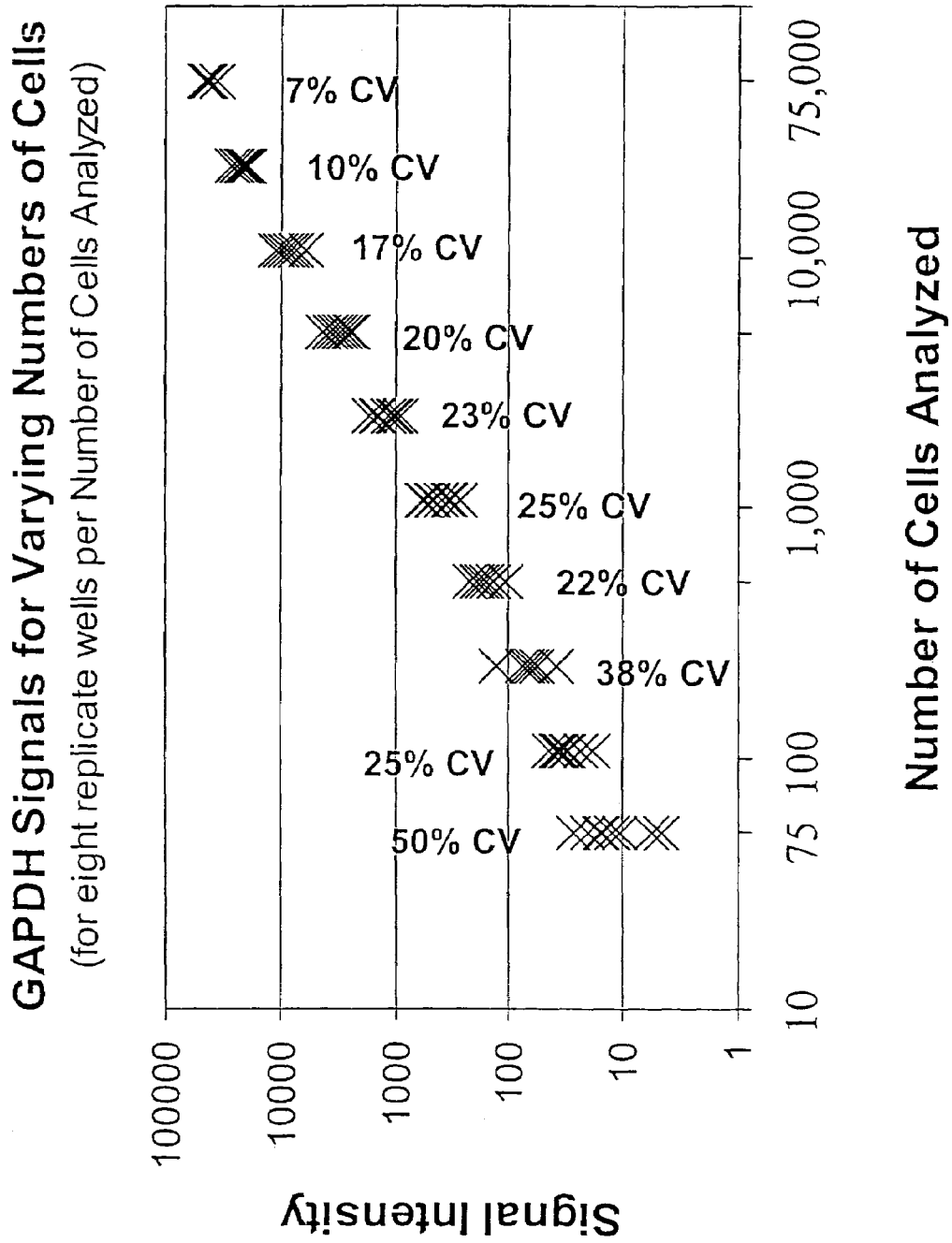

FIG. 34 shows that the sensitivity of the assay is high, e.g., the target mRNAs for GAPDH can be detected when RNA from a sample of as few as, or fewer than, 1,000 cells is assayed.

Figure 35:
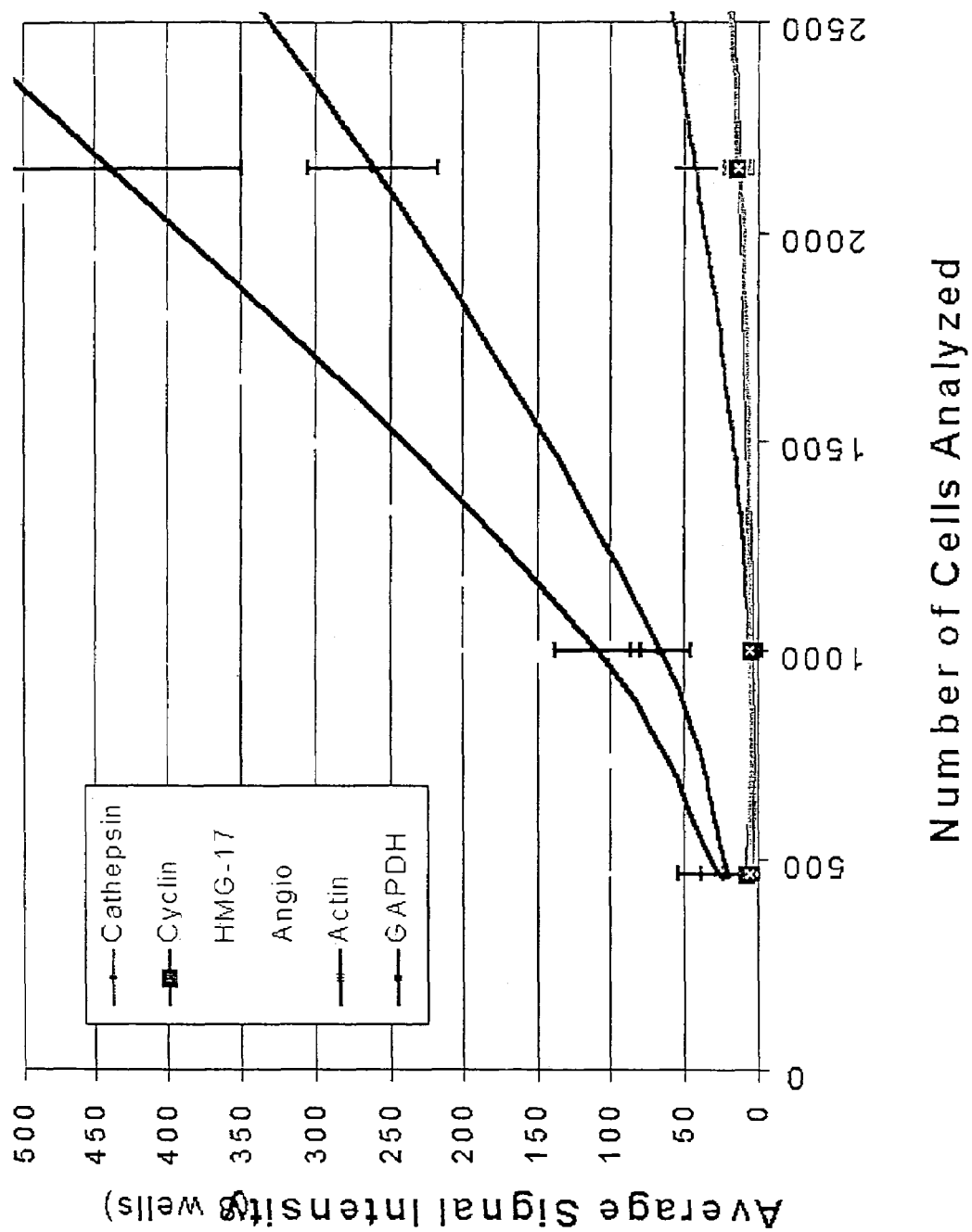

FIG. 35, performed using essentially the protocol of Example 25 and the array and targets of Example 27, shows that many of the target mRNAs tested can be detected even when RNA from a sample of as few as, or fewer than, 1000 cells is assayed, and all of the targets, even those expressed at low abundance, can be detected when the RNA is from as few as, or fewer than, 10,000 cells.

Example 31

Oligonucleotide Reagent Options (See FIG. 36)

FIG. 36 schematically shows several types of oligonucleotide reagents which can be used in the methods of the invention. The figure depicts assay schemes in which oligonucleotide anchors are attached to a surface via either their 5' or their 3' ("Inverted") termini, and in which oligonucleotides have two recognition moieties that are either adjacent to each other ("Shortened") or are separated by nucleic acid spacers. Each box represents 5 nucleotides.

Example 32

Nuclease Protection Fragment Amplification Methods (See FIGS. 37-39 and 42)

FIG. 37 illustrates nuclease protection fragment amplification by PCR.

FIG. 38 illustrates nuclease protection fragment amplification by ligase. By selecting a' as a 12 base sequence, out of the 25 bases which in ligated a' a binds to the array, hybridization conditions can be selected which only allow the ligated, 25 base sequence of the a'a molecules to bind. Discrimination can be improved by using a modified nucleotide(s) in each portion of the linker binding region of a' and a. If the cycles of heat dissociation destroy the ligase, it can be re-added for each cycle.

FIG. 39 illustrates nuclease protection fragment amplification by nuclease protection. (DNA a) strand complementary to the (Nuclease Protection Fragment b) can contain modified bases which hybridize at lower temperature than the (RNA a), or the (RNA a) can be destroyed before (DNA a) is added. Likewise, the (Linker a) for (DNA a) can contain modified nucleotides which allow hybridization at lower temperature than (Nuclease Protection Fragment b), even if the (Linker a)/(DNA a) hybrid is 25 bases and the (DNA a)/(Nuclease Protection Fragment b) is a 50 base hybridization, especially when taken into account experimentally is that the DNA strands in solution are dilute, and passing thorough a highly concentrated, essentially infinitely high concentration of (Linker A). The flow through apparatus can be replaced with a plate comprising an array for capture. The linear array can be replaced with a 2-D or 3-D array.

FIG. 42 illustrates nuclease protection fragment amplification by polymerase. After the nuclease protection reaction is complete and the nuclease protection fragment is dissociated from the RNA, a primer (a') is added which contains a double stranded promoter for an RNA polymerase (e.g., T7 polymerase) and a primer for extension along the nuclease protection fragment template (e.g., extension by reverse transcriptase (RT) for the replication of the RNA or DNA, or Taq polymerase for the replication of DNA), such that after binding to the nuclease protection fragment (e.g., RT or Taq polymerase) will use this as a template to form a double stranded DNA complex, with the double stranded promoter region apposed to the end of the nuclease protection fragment sequence. Addition of ligase will ligate the second strand of the promoter to the nuclease protection fragment strand, unless the first base was a mismatched SNP, and therefore during the nuclease protection reaction S1 clipped off the unprotected base. Ligase will not ligate the promoter to the nuclease protection fragment because of the skipped base. In the case of ligation, the b strand is converted to an extended b" strand incorporating the polymerase promoter and amplification can proceed using polymerase, and continue as after the addition of RT primer b'. The promoter/extended end of the nuclease protection fragment is used to bind to the array or to a detection linker or detection probe. For detection of SNP, this hybridization is arranged so that the SNP site is approximately in the middle of the sequence used for hybridization to the array (detection linker, or detection probe, etc.). The array (detection linker, or detection probe) hybridization region of the extended nuclease protection probe does not have to include all the bases at the end (some of the bases at the end of the extended nuclease protection probe can overhang without having a complementary hybridization sequence in the linker, etc.). In variations not depicted, it is not necessary to ligate before use of (e.g. T7) polymerase, and therefore the SNP detection is performed by selecting a sequence positioning the SNP in the middle of the sequence hybridizing to a', and using an SNP detection protocol as described elsewhere herein. It is not necessary to extend the a' strand, but instead RNA polymerase can use the promoter hybridized to the single stranded nuclease protection fragment (omitting the indicated RT extension, or alternative Taq polymerase extension step depicted) to produce RNA.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and in the figures are hereby incorporated by reference.

What is claimed is:

1. A method of detecting at least one nucleic acid target, comprising contacting a cell sample which may comprise said target(s) with a nuclease protection fragment(s) specific for and which binds to said target(s), exposing the sample to a nuclease effective to digest single stranded nucleic acid, and contacting the resultant sample with a combination which comprises, before the addition of said sample, i) a surface comprising multiple spatially discrete regions, at least two of which are substantially identical, each region comprising ii) at least two different loci of oligonucleotide anchors, each anchor in association with iii) a bifunctional linker which has a first portion that is specific for the oligonucleotide anchor, and a second portion that comprises a probe which is specific for said nuclease protection fragment(s), under conditions effective for said nuclease protection fragment(s) to bind to said combination, wherein said nucleic acid target is lysed from said cells by exposure of said cells in said sample to a lysis solution comprising amounts effective for lysis of about 8 to about 60% v/v of formamide, about 0.01 to about 0.5% w/v of SDS and 0.5-6X SSC buffer.

2. The method of claim 1 wherein the buffer is about 3X SSC buffer.

3. A method according to claim 1 wherein the resultant solution is employed without further purification from other cellular components.

4. A method according to claim 1 wherein the resultant solution is employed without further purification.

5. A method of detecting at least one nucleic acid target, comprising contacting a cell sample which may comprise said target(s) with a nuclease protection fragment(s) specific for and which binds to said target(s), exposing the sample to a nuclease effective to digest single stranded nucleic acid, and contacting the resultant sample with a surface comprising a probe which is specific for said nuclease protection fragment(s), under conditions effective for said nuclease protection fragment(s) to bind to said surface, wherein said nucleic acid target is released from said cells by exposure of said cells in said sample an aqueous medium comprising about 8 to about 60% v/v of formamide, about 0.01 to about 0.5% w/v of SDS and 0.5-6X SSC buffer.

6. The method of claim 5, wherein the buffer is about 3 X SSC buffer.

7. A method according to claim 5 wherein the resultant medium is employed without further purification from other cellular components.

8. A method according to claim 5 wherein the resultant medium is employed without further purification.

9. A method of detecting at least one nucleic acid target, comprising contacting a cell sample which may comprise said target(s) with a nuclease protection fragment(s) specific for and which binds to said target(s), exposing the sample to a nuclease effective to digest single stranded nucleic acid, and contacting the resultant sample with a surface comprising a probe which is specific for said nuclease protection fragment(s), under conditions effective for said nuclease protection fragment(s) to bind to said surface, wherein said nucleic acid target is lysed from said cells by exposure of said cells in said sample to a lysis solution comprising amounts effective for lysis of about 8 to about 60% v/v of formamide, about 0.01 to about 0.5% w/v of SDS 0.5-6X SSC buffer.

10. A method of claim 9 wherein said surface is a bead.

11. A method according to claim 10 wherein the resultant solution is employed without further purification from other cellular components.

12. A method according to claim 10 wherein the resultant solution is employed without further purification.

13. A method of claim 9 wherein said surface is flat or curved.

14. A method of claim 9 comprising contacting the sample with 100 or more nuclease protection fragments of different specificities.

15. A method according to claim 9 wherein the resultant solution is employed without further purification from other cellular components.

16. A method according to claim 9 wherein the resultant solution is employed without further purification.

17. A method of detecting at least one nucleic acid target, comprising contacting a cell sample which may comprise said target(s) with a nuclease protection fragment(s) specific for and which binds to said target(s), exposing the sample to a nuclease effective to digest single stranded nucleic acid, and contacting the resultant sample with a combination which comprises, before the addition of said sample, i) a surface comprising multiple spatially discrete regions, at least two of which are substantially identical, each region comprising ii) at least two different loci of oligonucleotide anchors, each anchor in association with iii) a bifunctional linker which has a first portion that is specific for the oligonucleotide anchor, and a second portion that comprises a probe which is specific for said nuclease protection fragment(s), under conditions effective for said nuclease protection fragment(s) to bind to said combination, wherein said sample is exposed to a lysis solution at a temperature of about 90°C-100°C at which temperature substantially only mRNA and no DNA is released in a form in which it binds to said protection fragment(s), and/or is exposed to a lysis solution at an elevated temperature of about 105°C -115°C, at which temperature both mRNA and DNA are released in a form in which each binds to said protection fragment(s) wherein said lysis solution comprises amounts effective for lysis of about 8 to about 60% v/v of formamide, about 0.01 to about 0.5% w/v of SDS and 0.5-6X SSC buffer.

18. A method of claim 17 wherein anchors located in at least one locus are in association with about 2 to about 4 different bifunctional linkers, having different nuclease protection fragment, and thus different targets, specificities.

19. A method of claim 17 wherein anchors located in at least one locus are in association with about 2 to about 4 different bifunctional linkers, having different nuclease protection fragment, and thus different target, specificities.

20. A method of claim 17 wherein said sample is exposed to a lysis solution at a temperature of about 90° C.-100° C. at which temperature substantially only mRNA and no DNA is released in a form in which it binds to said protection fragment(s), and then is exposed to a lysis solution at an elevated temperature of about 105° C.-115° C., at which temperature both mRNA and DNA are released in a form in which each binds to said protection fragment(s).

21. A method according to claim 17 wherein the resultant solution is employed without further purification from other cellular components.

22. A method according to claim 17 wherein the resultant solution is employed without further purification.

23. A method of detecting at least one nucleic acid target, comprising
    contacting a cell sample which may comprise said target(s) with a nuclease protection fragment(s) specific for and which binds to said target(s),
    exposing the sample to a nuclease effective to digest single stranded nucleic acid, and
    contacting the resultant sample with a surface comprising a probe which is specific for said nuclease protection fragment(s), under conditions effective for said nuclease protection fragment(s) to bind to said surface,
    wherein said sample is exposed to a lysis solution at a temperature of about 900C-1000C at which temperature substantially only mRNA and no DNA is released in a form in which it binds to said protection fragment(s), and/or is exposed to alysis solution at a temperature of about 1050C - 1150C, at which temperature both mRNA and DNA are released in a form in which each binds to said protection fragment(s) wherein said lysis solution comprises amounts effective for lysis of about 8 to about 60% v/v of formamide, about 0.01 to about 0.5% w/v of SDS and 0.5-6X SSC buffer.

24. A method of claim 23 wherein said sample solution containing said lysis solution is diluted such that said solution does not inhibit the functioning of said nuclease to digest single stranded nucleic acid.

25. A method of claim 23 wherein said sample is exposed to a lysis solution at a temperature of about 90° C.-100° C. at which temperature substantially only mRNA and no DNA is released in a form in which it binds to said protection fragment(s), and then is exposed to a lysis solution at an elevated temperature of about 105° C.-115° C., at which temperature both mRNA and DNA are released in a form in which each binds to said protection fragment(s).

26. A method according to claim 23 wherein the resultant solution is employed without further purification from other cellular components.

27. A method according to claim 23 wherein the resultant solution is employed without further purification.

28. A method of detecting at least one nucleic acid target, comprising
    contacting a cell sample which may comprise said target(s) with a nuclease protection fragment(s) specific for and which binds to said target(s),
    exposing the sample to a nuclease effective to digest single stranded nucleic acid, and
    contacting the resultant sample with a comprising a probe which is specific for said nuclease protection fragment(s), under conditions effective for said nuclease proctection fragment(s) to bind to said surface,
        i) a surface comprising multiple spatially discrete regions, at least two of which are substantially identical, each region comprising
        ii) at least two different loci of oligonucleotide anchors, each anchor in association with
        iii) a bifunctional linker which has a first portion that is specific for the oligonucleotide anchor, and a second portion that comprises a probe which is specific for said nuclease protection fragment(s),
    under conditions effective for said nuclease protection fragment(s) to bind to said combination,
    wherein said sample is exposed to an aqueous solution at a temperature of about 90°C-100°C at which temperature substantially only mRNA and no DNA is made available in a form in which it binds to said protection fragment(s), and/or is exposed to said aqueous solution at an elevated temperature of about 105°C- 115°C, at which temperature both mRNA and DNA are made available in a form in which each binds to said protection fragment(s), wherein said aqueous solution comprises about 8 to about 60% v/v of formamide, about 0.01 to about 0.5% w/v of SDS and 0.5-6X SSC buffer.

29. A method of claim 28 wherein anchors located in at least one locus are in association with about 2 to about 4 different bifunctional linkers, having different nuclease protection fragment, and thus different target, specificities.

30. A method of claim 28 wherein said solution is diluted such that it does not inhibit the functioning of said nuclease to digest single stranded nucleic acid.

31. A method of claim 28 wherein said sample is exposed to said solution at a temperature of about 90°C-100°C at which temperature substantially only mRNA and no DNA is made available in a form in which it binds to said protection fragment(s), and then is exposed to saida permeabilization and/or lysis solution at an elevated temperature of about 105°C-115°C, at which temperature both mRNA and DNA are made available in a form in which each binds to said protection fragment(s).

32. A method according to claim 28 wherein the resultant solution is employed without further purification from other cellular components.

33. A method according to claim 28 wherein the resultant solution is employed without further purification.

34. A method of detecting at least one nucleic acid target, comprising
    contacting a cell sample which may comprise said target(s) with a nuclease protection fragment(s) specific for and which binds to said target(s), exposing the sample to a nuclease effective to digest single stranded nucleic acid, and contacting the resultant sample with a surface comprising a probe which is specific for said nuclease protection fragment(s), under conditions effective for said nuclease protection fragment(s) to bind to said surface, wherein said sample is exposed to an aqueous solution at a temperature of about 90°C-100°C at which temperature substantially only mRNA and no DNA is made available in a form in which it binds to said protection fragment(s), and/or is exposed to said aqueous solution at a temperature of about 105°C - 115°C, at which temperature both mRNA and DNA are made available in a form in which each binds to said protection fragment(s) wherein said aqueous solution comprises about 8 to about 60% v/v of formamide, about 0.01 to about 0.5% w/v of SDS and 0.5-6X SSC buffer.

35. A method of claim 34 wherein said solution is diluted such that it does not inhibit the functioning of said nuclease to digest single stranded nucleic acid.

36. A method of claim 34 wherein said sample is exposed to said solution at a temperature of about 90°C-100°C at which temperature substantially only mRNA and no DNA is released in a form in which it binds to said protection fragment(s), and then is exposed to said solution at an elevated temperature of about 105°C - 115°C, at which temperature both mRNA and DNA are released in a form in which each binds to said protection fragment(s).

37. A method of claim 34 wherein said surface is a bead.

38. A method according to claim 37 wherein the resultant solution is employed without further purification from other cellular components.

39. A method according to claim 37 wherein the resultant solution is employed without further purification.

40. A method of claim 34 wherein said surface is flat or curved.

41. A method according to claim 40 wherein the resultant solution is employed without further purification.

42. A method of claim 34 comprising contacting the sample with 100 or more nuclease protection fragments of different specificities.

43. A method according to claim 33 wherein the resultant solution is employed without further purification from other cellular components.

44. A method according to claim 34 wherein the resultant solution is employed without further purification.

45. A method of releasing nucleic acids from cells without hybridization of said nucleic acids, comprising treating cells with an aqueous solution comprising about 8 to about 60% v/v of formamide, about 0.01 to about 0.5% w/v of SDS and 0.5-6X SSC buffer.

46. A method of claim 45 wherein in said solution the amount of formamide is about 10 to about 30% v/v.

47. A method of claim 45 wherein said cells are on a surface, in tissue or in a whole organism.

48. The method of claim 45 wherein in said solution the buffer is about 3X SSC buffer.

49. A method of claim 45 further comprising subsequently hybridizing to probes, nucleic acids released from said cells.

50. A method according to claim 45 wherein the resultant solution is employed without further purification from other cellular components.

51. A method according to claim 45 wherein the resultant solution is employed without further purification.

52. A method of detecting at least one nucleic acid target present in a cell sample which may comprise said target(s), comprising prior to a step of hybridization of nucleic acid for detecting said target(s), exposing said sample to an aqueous solution comprising of about 8 to about 60% v/v of formamide, about 0.01 to about 0.5% w/v of SDS and 0.5-6X SSC buffer, contacting the sample with a nuclease protection fragment(s) specific for and which binds to said target(s) which has been made accessible by exposure to said solution, exposing the sample to a nuclease effective to digest single stranded nucleic acid, and contacting the resultant sample with a combination which comprises, before the addition of said sample,
  i) a surface comprising multiple spatially discrete regions, at least two of which are substantially identical, each region comprising
  ii) at least two different loci of oligonucleotide anchors, each anchor in association with
  iii) a bifunctional linker which has a first portion that is specific for the oligonucleotide anchor, and a second portion that comprises a probe which is specific for said nuclease protection fragment(s),
under conditions effective for said nuclease protection fragment(s) to bind to said combination, and
wherein anchors located in at least one locus are in association with about 2 to about 4 different bifunctional linkers, having different nuclease protection fragment, and thus different target, specificities.

53. A method of claim 52 wherein in said solution the amount of formamide is about 10 to about 30% v/v.

54. The method of claim 52 wherein in said solution the buffer is about 3 X SSC buffer.

55. A method of claim 52 wherein said cells are on a surface, in tissue or in a whole organism.

56. A method according to claim 52 wherein the resultant solution is employed without further purification from other cellular components.

57. A method according to claim 52 wherein the resultant solution is employed without further purification.

58. A method of detecting at least one nucleic acid target present in a cell sample which may comprise said target(s), comprising prior to a step of hybridization of nucleic acid for detecting said target(s), exposing said sample to an aqueous solution comprising about 8 to about 60% v/v of formamide, about 0.01 to about 0.5% w/v of SDS and 0.5-6X SSC buffer, contacting the sample with a nuclease protection fragment(s) specific for and which binds to said target(s) which has been made accessible by exposure to said solution, exposing the sample to a nuclease effective to digest single stranded nucleic acid, and contacting the resultant sample with a combination which comprises, before the addition of said sample,
  i) a surface comprising multiple spatially discrete regions, at least two of which are substantially identical, each region comprising
  ii) at least two different loci of oligonucleotide anchors, each anchor in association with
  iii) a bifunctional linker which has a first portion that is specific for the oligonucleotide anchor, and a second portion that comprises a probe which is specific for said nuclease protection fragment(s),
under conditions effective for said nuclease protection fragment(s) to bind to said combination.

59. A method of claim 58 wherein in said solution the amount of formamide is about 10 to about 30% v/v.

60. A method of claim 58 wherein said cells are on a surface, in tissue or in a whole organism.

61. The method of claim 58 wherein in said solution the buffer is about 3 X SSC buffer.

62. A method according to claim 58 wherein the resultant solution is employed without further purification from other cellular components.

63. A method of lysing cells which have not been already lysed, comprising treating cells with an aqueous solution comprising about 8 to about 60% v/v of formamide, about 0.01 to about 0.5% w/v of SDS and 0.5-6X SSC buffer.

64. A method according to claim 63 wherein the resultant solution is employed without further purification from other cellular components.

65. A method according to claim 63 wherein the resultant solution is employed without further purification.

66. A method of detecting at least one nucleic acid target present in a cell sample which may comprise said target(s), comprising
    prior to a step of hybridization of nucleic acid for detecting said target(s), exposing said sample to an aqueous solution comprising about 8 to about 60% v/v of formamide, about 0.01 to about 0.5% w/v of SDS and 0.5-6X SSC buffer,
    contacting the sample with a nuclease protection fragment(s) specific for and which binds to said target(s) which has been made accessible by exposure to said solution,
    exposing the sample to a nuclease effective to digest single stranded nucleic acid,
    and contacting the resultant sample with a surface comprising a probe which is specific for said nuclease protection fragment(s), under conditions effective for said nuclease protection fragment(s) to bind to said surface.

67. A method of claim 66 wherein in said solution the amount of formamide is about 10 to about 30% v/v.

68. A method of claim 66 wherein said cells are on a surface.

69. A method of claim 66 wherein said surface is a bead.

70. A method of claim 66 wherein said surface is flat or curved.

71. A method of claim 66 comprising contacting the sample with 100 or more nuclease protection fragments of different specificities.

72. A method according to claim 66 wherein the resultant solution is employed without further purification from other cellular components.

73. A method according to claim 66 wherein the resultant solution is employed without further purification.

74. A method of detecting at least one nucleic acid target, comprising
    contacting a cell sample which may comprise said target(s) with a nuclease protection fragment(s) specific for and which binds to said target(s),
    exposing the sample to a nuclease effective to digest single stranded nucleic acid, and contacting the resultant sample with a combination which comprises, before the addition of said sample,
    i) a surface comprising multiple spatially discrete regions, at least two of which are substantially identical, each region comprising
    ii) at least two different loci of oligonucleotide anchors, each anchor in association with
    iii) a bifunctional linker which has a first portion that is specific for the oligonucleotide anchor, and a second portion that comprises a probe which is specific for said nuclease protection fragment(s),
    under conditions effective for said nuclease protection fragment(s) to bind to said combination, wherein said nucleic acid target is released from said cells by exposure of said cells in said sample to a solution comprising of about 8 to about 60% v/v of formamide, about 0.01 to about 0.5% w/v of SDS and 0.5-6X SSC buffer.

75. A method of claim 70 wherein said surface is a bead.

76. A method according to claim 75 wherein the resultant solution is employed without further purification from other cellular components.

77. A method according to claim 75 wherein the resultant solution is employed without further purification.

78. A method of claim 70 wherein said surface is flat or curved.

79. A method of claim 70 comprising contacting the sample with 100 or more nuclease protection fragments of different specificities.

80. A method according to claim 74 wherein the resultant solution is employed without further purification from other cellular components.

81. A method according to claim 74 wherein the resultant solution is employed without further purification.

* * * * *

UNITED STATES PATENT AND TRADEMARK OFFICE
CERTIFICATE OF CORRECTION

| | | |
|---|---|---|
| PATENT NO. | : 7,659,063 B2 | Page 1 of 1 |
| APPLICATION NO. | : 10/865853 | |
| DATED | : February 9, 2010 | |
| INVENTOR(S) | : Kris et al. | |

It is certified that error appears in the above-identified patent and that said Letters Patent is hereby corrected as shown below:

Column 141, line 52 reads "about 1050C - 1150C, at which temperature both mRNA"
should read --about 105°C - 115°C, at which temperature both mRNA--.
Column 142, line 15 reads "contacting the resultant sample with a comprising a probe"
should read --contacting the resultant sample with a surface comprising a probe--.
Column 142, line 52 reads "made available in a form in which it binds to said protection"
should read --released in a form in which it binds to said protection--.
Column 142, line 53 reads "fragment(s), and then is exposed to saida permeabilization"
should read --fragment(s), then is exposed to a--.
Column 142, line 54 reads "and/or lysis, solution at an elevated temperature of about"
should read --lysis solution at an elevated temperature of about--.
Column 142, line 56 reads "are made available in a form in which each binds to said"
should read --are released in a form in which each binds to said--.
Column 146, line 28 reads "of about 8 to about 60% v/v of formamide, about 0.01 to"
should read --about 8 to about 60% v/v formamide, about 0.01 to--.

Signed and Sealed this
Thirteenth Day of March, 2012

David J. Kappos
*Director of the United States Patent and Trademark Office*